US011530432B2

(12) United States Patent
Jewett et al.

(10) Patent No.: US 11,530,432 B2
(45) Date of Patent: Dec. 20, 2022

(54) COMPOSITIONS AND METHODS FOR RAPID IN VITRO SYNTHESIS OF BIOCONJUGATE VACCINES IN VITRO VIA PRODUCTION AND N-GLYCOSYLATION OF PROTEIN CARRIERS IN DETOXIFIED PROKARYOTIC CELL LYSATES

(71) Applicants: Northwestern University, Evanston, IL (US); Cornell University, Ithaca, NY (US)

(72) Inventors: Michael Christopher Jewett, Evanston, IL (US); Jessica Carol Stark, Evanston, IL (US); Matthew P. DeLisa, Ithaca, NY (US); Thapakorn Jaroentomeechai, Ithaca, NY (US)

(73) Assignees: Northwestern University, Evanston, IL (US); Cornell University, Ithaca, NY (US)

( * ) Notice: Subject to any disclaimer, the term of this patent is extended or adjusted under 35 U.S.C. 154(b) by 671 days.

(21) Appl. No.: 16/357,820

(22) Filed: Mar. 19, 2019

(65) Prior Publication Data
US 2019/0284600 A1 Sep. 19, 2019

Related U.S. Application Data

(60) Provisional application No. 62/644,811, filed on Mar. 19, 2018, provisional application No. 62/791,425, filed on Jan. 11, 2019.

(51) Int. Cl.
*C12P 21/00* (2006.01)
*A61K 39/02* (2006.01)
*C12N 9/10* (2006.01)
*A61K 39/108* (2006.01)
*A61K 39/00* (2006.01)

(52) U.S. Cl.
CPC ........ *C12P 21/005* (2013.01); *A61K 39/0258* (2013.01); *C12N 9/1081* (2013.01); *A61K 2039/6087* (2013.01); *C12Y 204/99* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,496,538 A | 1/1985 | Gordon |
| 4,683,195 A | 7/1987 | Mullis et al. |
| 4,683,202 A | 7/1987 | Mullis |
| 4,727,136 A | 2/1988 | Jennings |
| 5,478,730 A | 12/1995 | Alakhov et al. |
| 5,494,810 A | 2/1996 | Barany et al. |
| 5,556,769 A | 9/1996 | Wu et al. |
| 5,623,057 A | 4/1997 | Kniskern |
| 5,665,563 A | 9/1997 | Beckler |
| 5,679,352 A | 10/1997 | Chong |
| 6,168,931 B1 | 1/2001 | Swartz et al. |
| 6,248,334 B1 | 6/2001 | Lees |
| 6,518,058 B1 | 2/2003 | Biryukov et al. |
| 6,531,131 B1 | 3/2003 | Gu |
| 6,783,957 B1 | 8/2004 | Biryukov et al. |
| 6,869,774 B2 | 3/2005 | Endo et al. |
| 6,994,986 B2 | 2/2006 | Swartz et al. |
| 7,118,883 B2 | 10/2006 | Inoue et al. |
| 7,189,528 B2 | 3/2007 | Higashide et al. |
| 7,338,789 B2 | 3/2008 | Swartz et al. |
| 7,387,884 B2 | 6/2008 | Suzuki et al. |
| 7,396,664 B2 | 7/2008 | Daly |
| 7,399,610 B2 | 7/2008 | Shikata et al. |
| 8,703,471 B2 | 4/2014 | Aebi |
| 8,999,668 B2 | 4/2015 | Delisa |
| 9,951,392 B2 | 4/2018 | Jewett |
| 2004/0209321 A1 | 10/2004 | Swartz et al. |
| 2005/0054044 A1 | 3/2005 | Swartz et al. |
| 2005/0170452 A1 | 8/2005 | Wildt |
| 2006/0211085 A1 | 9/2006 | Bobrowicz |
| 2006/0234345 A1 | 10/2006 | Schwartz |
| 2006/0252672 A1 | 11/2006 | Betenbaugh |

(Continued)

FOREIGN PATENT DOCUMENTS

| | | |
|---|---|---|
| WO | 2003056914 A1 | 7/2003 |
| WO | 2004013151 A2 | 2/2004 |

(Continued)

OTHER PUBLICATIONS

Failmezger et al. Sci Rep 7, 16524 (2017).*

(Continued)

*Primary Examiner* — Oluwatosin A Ogunbiyi

(74) *Attorney, Agent, or Firm* — Quarles & Brady LLP

(57) ABSTRACT

Disclosed are methods, systems, components, and compositions for cell-free synthesis of glycosylated carrier proteins. The glycosylated carrier proteins may be utilized in vaccines, including anti-bacterial vaccines. The glycosylated carrier proteins may include a bacterial polysaccharide conjugated to a carrier, which may be utilized to generate an immune response in an immunized host against the polysaccharide conjugated to the carrier. The glycosylated carrier proteins may be synthesized in cell-free glycoprotein synthesis (CFGpS) systems using prokaryote cell lysates that are enriched in components for glycoprotein synthesis such as oligosaccharyltransferases (OSTs) and lipid-linked oligosaccharides (LLOs) including OSTs and LLOs associated with synthesis of bacterial O antigens.

15 Claims, 21 Drawing Sheets

Specification includes a Sequence Listing.

(56) References Cited

U.S. PATENT DOCUMENTS

| | | | |
|---|---|---|---|
| 2006/0257399 | A1 | 11/2006 | Gerngross |
| 2006/0286637 | A1 | 12/2006 | Hamilton |
| 2007/0026485 | A1 | 2/2007 | Defrees |
| 2007/0154983 | A1 | 7/2007 | Calhoun et al. |
| 2007/0178551 | A1 | 8/2007 | Gerngross |
| 2008/0138857 | A1 | 6/2008 | Swartz et al. |
| 2012/0171720 | A1 | 7/2012 | Church et al. |
| 2014/0045267 | A1 | 2/2014 | Lajoie |
| 2014/0255987 | A1 | 9/2014 | Delisa |
| 2014/0295492 | A1 | 10/2014 | Jewett et al. |
| 2015/0259757 | A1 | 9/2015 | Jewett |
| 2016/0060301 | A1 | 3/2016 | Jewett |
| 2016/0362708 | A1 | 12/2016 | Jewett |
| 2017/0349928 | A1 | 12/2017 | Jewett |
| 2018/0016612 | A1 | 1/2018 | Jewett |
| 2018/0016614 | A1 | 1/2018 | Jewett |
| 2018/0044905 | A1 | 2/2018 | Potts |
| 2018/0298416 | A1 | 10/2018 | Jewett |

FOREIGN PATENT DOCUMENTS

| | | | |
|---|---|---|---|
| WO | 2004035605 | A2 | 4/2004 |
| WO | 2006102652 | A2 | 9/2006 |
| WO | 2006119987 | A2 | 11/2006 |
| WO | 2007120932 | A2 | 10/2007 |
| WO | 2017117539 | A1 | 7/2017 |

OTHER PUBLICATIONS

Mamat et al. Microbial Cell Factories (2015) 14:57.*
Ihssen et al. Open Biol. 5: 140227. http://dx.doi.org/10.1098/rsob.140227 2015.*
Schwarz et al. Glycobiology vol. 21, No. 1, pp. 45-54, 2011.*
Adiga, R., et al., Point-of-care production of therapeutic proteins of good-manufacturing-practice quality. Nat. Biomed. Eng., 2018.
Ashok, A., et al., Improving cold chain systems: Challenges and solutions. Vaccine, 2017. 35(17): p. 2217-2223.
Astronomo, R.D. et al, Carbohydrate vaccines: Developing sweet solutions to sticky situations? Nat. Rev. Drug Discov., 2010. 9(4): p. 308-24.
Avci, F.Y. et al, How bacterial carbohydrates influence the adaptive immune system. Annu. Rev. Immunol., 2010. 28: p. 107-30.
Brito, L.A. et al, Acceptable levels of endotoxin in vaccine formulations during preclinical research. J. Pharm. Sci., 2011. 100(1): p. 34-7.
Carlson, E.D., et al., Cell-free protein synthesis: Applications come of age. Biotechnol. Adv., 2012. 30(5): p. 1185-94.
Casella, C.R. et al, Putting endotoxin to work for us: monophosphoryl lipid A as a safe and effective vaccine adjuvant. Cell. Mol. Life Sci., 2008. 65(20): p. 3231-40.
Celik, E., et al., Glycoarrays with engineered phages displaying structurally diverse oligosaccharides enable high-throughput detection of glycan-protein interactions. Biotechnol. J., 2015. 10(1): p. 199-209.
Chen, L., et al., Outer membrane vesicles displaying engineered glycotopes elicit protective antibodies. Proc. Natl. Acad. Sci. U. S. A., 2016.
Chen, M.M., et al, From peptide to protein: comparative analysis of the substrate specificity of N-linked glycosylation in C. jejuni. Biochemistry, 2007. 46(18): p. 5579-85.
Crowell, L.E., et al., On-demand manufacturing of clinical-quality biopharmaceuticals. Nat Biotechnol, 2018.
Cuccui, J., et al., Exploitation of bacterial N-linked glycosylation to develop a novel recombinant glycoconjugate vaccine against Francisella tularensis. Open Biol., 2013. 3(5): p. 130002.
Cywes-Bentley, C., et al., Antibody to a conserved antigenic target is protective against diverse prokaryotic and eukaryotic pathogens. Proc. Natl. Acad. Sci. U. S. A., 2013. 110(24): p. E2209-18.
Feldman, M.F., et al., Engineering N-linked protein glycosylation with diverse O antigen lipopolysaccharide structures in *Escherichia coli*. Proc. Natl. Acad. Sci. U. S. A., 2005. 102(8): p. 3016-21.

Frasch, C.E., Preparation of bacterial polysaccharide-protein conjugates: analytical and manufacturing challenges. Vaccine, 2009. 27(46): p. 6468-70.
Fulop, M., et al., Role of antibody to lipopolysaccharide in protection against low- and high-virulence strains of Francisella tularensis. Vaccine, 2001. 19(31): p. 4465-72.
Garcia-Quintanilla, F., et al., Production of a recombinant vaccine candidate against Burkholderia pseudomallei exploiting the bacterial N-glycosylation machinery. Front. Microbiol., 2014. 5: p. 381.
Guarino, C., et al. (2012). A prokaryote-based cell-free translation system that efficiently synthesizes glycoproteins. Glycobiology, 22(5), 596-601.
Haghi, F., et al., Cloning, expression and purification of outer membrane protein PorA of Neisseria meningitidis serogroup B. J Infect Dev Ctries, 2011. 5(12): p. 856-62.
Hatz, C.F., et al., Safety and immunogenicity of a candidate bioconjugate vaccine against Shigella dysenteriae type 1 administered to healthy adults: A single blind, partially randomized Phase I study. Vaccine, 2015. 33(36): p. 4594-601.
Hong, S.H., et al., Cell-free protein synthesis from a release factor 1 deficient *Escherichia coli* activates efficient and multiple site-specific nonstandard amino acid incorporation. ACS Synth. Biol., 2014. 3(6): p. 398-409.
Huttner, A., et al., Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet. Infect. Dis., 2017.
Jaroentomeechai, T., et al. "A pipeline for studying and engineering single-subunit oligosaccharyltransferases." Methods in enzymology. vol. 597. Academic Press, 2017. 55-81.
Jaroentomeechai, T., et al., Single-pot glycoprotein biosynthesis using a cell-free transcription-translation system enriched with glycosylation machinery. Nat. Commun., 2018. 9(1): p. 2686.
Jewett, M.C. et al., Mimicking the *Escherichia coli* cytoplasmic environment activates long-lived and efficient cell-free protein synthesis. Biotechnol. Bioeng., 2004. 86(1): p. 19-26.
Jones, C., Vaccines based on the cell surface carbohydrates of pathogenic bacteria. An. Acad. Bras. Cienc., 2005. 77(2): p. 293-324.
Kim, D.M. et al, Regeneration of adenosine triphosphate from glycolytic intermediates for cell-free protein synthesis. Biotechnol. Bioeng., 2001. 74(4): p. 309-16.
Knapp, K.G., et al, Cell-free synthesis of proteins that require disulfide bonds using glucose as an energy source. Biotechnol. Bioeng., 2007. 97(4): p. 901-8.
Kowarik, M., et al., Definition of the bacterial N-glycosylation site consensus sequence. EMBO J., 2006. 25(9): p. 1957-66.
Kumru, O.S., et al., Vaccine instability in the cold chain: mechanisms, analysis and formulation strategies. Biologicals, 2014. 42(5): p. 237-59.
Lockhart, S., Conjugate vaccines. Expert Rev. Vaccines, 2003. 2(5): p. 633-48.
Lu, Z., et al., Protective B-cell epitopes of Francisella tularensis O-polysaccharide in a mouse model of respiratory tularaemia. Immunology, 2012. 136(3): p. 352-60.
Ma, Z., et al., Glycoconjugate vaccine containing *Escherichia coli* O157:H7 O-antigen linked with maltose-binding protein elicits humoral and cellular responses. PLoS One, 2014. 9(8): p. e105215.
Marshall, L.E., et al., An O-antigen glycoconjugate vaccine produced using protein glycan coupling technology is protective in an inhalational rat model of tularemia. J. Immunol. Res., 2018. 2018: p. 8087916.
Matthias, D.M., et al., Freezing temperatures in the vaccine cold chain: a systematic literature review. Vaccine, 2007. 25(20): p. 3980-6.
Needham, B.D., et al., Modulating the innate immune response by combinatorial engineering of endotoxin. Proc. Natl. Acad. Sci. U. S. A., 2013. 110(4): p. 1464-9.
Ollis, A.A., et al., Engineered oligosaccharyltransferases with greatly relaxed acceptor-site specificity. Nat. Chem. Biol., 2014. 10(10): p. 816-22.

(56) References Cited

OTHER PUBLICATIONS

Ollis, A.A., et al., Substitute sweeteners: Diverse bacterial oligosaccharyltransferases with unique N-glycosylation site preferences. Sci. Rep., 2015. 5: p. 15237.

Pardee, K., et al., Paper-based synthetic gene networks. Cell, 2014. 159(4): p. 940-54.

Pardee, K., et al., Portable, on-demand biomolecular manufacturing. Cell, 2016. 167(1): p. 248-259.e12.

Pardee, K., et al., Rapid, low-cost detection of Zika virus using programmable biomolecular components. Cell, 2016. 165(5): p. 1255-66.

Perez, J.G., et al., Cell-free synthetic biology: Engineering beyond the cell. Cold Spring Harb. Perspect. Biol., 2016.

Perez-Pinera, P., et al., Synthetic biology and microbioreactor platforms for programmable production of biologies at the point-of-care. Nat Commun, 2016. 7: p. 12211.

Rappuoli, R., Glycoconjugate vaccines: Principles and mechanisms. Sci Transl Med, 2018. 10(456).

Riddle, M.S., et al., Safety and immunogenicity of a candidate bioconjugate vaccine against Shigella flexneri 2a administered to healthy adults: a single blind, randomized phase I study. Clin. Vaccine Immunol., 2016.

Salehi, A.S., et al., Cell-free protein synthesis of a cytotoxic cancer therapeutic: Onconase production and a just-add-water cell-free system. Biotechnol. J., 2016. 11(2): p. 274-81.

Schoborg, J.A., et al., A cell-free platform for rapid synthesis and testing of active oligosaccharyltransferases. Biotechnol. Bioeng., 2017.

Sebastian, S., et al., A defined O-antigen polysaccharide mutant of Francisella tularensis live vaccine strain has attenuated virulence while retaining its protective capacity. Infect. Immun., 2007. 75(5): p. 2591-602.

Stefan, A., et al., Overexpression and purification of the recombinant diphtheria toxin variant CRM197 in *Escherichia coli*. J Biotechnol, 2011. 156(4): p. 245-52.

Trotter, C.L., et al., Optimising the use of conjugate vaccines to prevent disease caused by Haemophilus influenzae type b, Neisseria meningitidis and *Streptococcus pneumoniae*. Vaccine, 2008. 26(35): p. 4434-45.

Guarino, C. "Investigating Oligosaccharyltransferases Of N-Linked Glycosylation Using *Escherichia coli*." PhD Dissertation; Cornell University. 2013.

Valvano, M.A. et al, Molecular cloning and expression in *Escherichia coli* K-12 of chromosomal genes determining the O7 lipopolysaccharide antigen of a human invasive strain of *E. coli* O7:K1. Infect. Immun., 1989. 57(3): p. 937-43.

Wacker et al., "N-linked glycosylation in Campylobacter jejuni and its functional transfer into *E. coli*," Science, Nov. 29, 2002; 298(5599):1790-3.

Wacker, M., et al., Prevention of *Staphylococcus aureus* infections by glycoprotein vaccines synthesized in *Escherichia coli*. J. Infect. Dis., 2014. 209(10): p. 1551-61.

Weintraub, A., Immunology of bacterial polysaccharide antigens. Carbohydr. Res., 2003. 338(23): p. 2539-2547.

Wetter, M., et al., Engineering, conjugation, and immunogenicity assessment of *Escherichia coli* O121 O antigen for its potential use as a typhoid vaccine component. Glycoconj. J., 2013. 30(5): p. 511-22.

U.S. Appl. No. 61/792,290.

\* cited by examiner

SEQUENCE LISTING

<160> NUMBER OF SEQ ID NOS: 12

<210> SEQ ID NO 1
<211> LENGTH: 1122
<212> TYPE: DNA
<213> ORGANISM: Escherichia coli

<400> SEQUENCE: 1

```
atgtcaaaag tcgctctcat caccggtgta accggacaag acggttctta cctggcagag      60
tttctgctgg aaaaaggtta cgaggtgcat ggtattaagc gtcgcgcatc gtcattcaac     120
accgagcgcg tggatcacat ttatcaggat ccgcacacct gcaacccgaa attccatctg     180
cattatggcg acctgagtga tacctctaac ctgacgcgca ttttgcgtga agtacagccg     240
gatgaagtgt acaacctggg cgcaatgagc cacgttgcgg tctcttttga gtcaccagaa     300
tataccgctg acgtcgacgc gatgggtacg ctgcgcctgc tggaggcgat ccgcttcctc     360
ggtctggaaa agaaaactcg tttctatcag gcttccacct ctgaactgta tggtctggtg     420
caggaaattc cgcagaaaga gaccacgccg ttctaccgc gatctccgta tgcggtcgcc      480
aaactgtacg cctactggat caccgttaac taccgtgaat cctacggcat gtacgcctgt     540
```

-continued

```
aacggaattc tcttcaacca tgaatccccg cgccgcggcg aaaccttcgt tacccgcaaa    600
atcacccgcg caatcgccaa catcgcccag gggctggagt cgtgcctgta cctcggcaat    660
atggattccc tgcgtgactg gggccacgcc aaagactacg taaaaatgca gtggatgatg    720
ctgcagcagg aacagccgga agatttcgtt atcgcgaccg gcgttcagta ctccgtgcgt    780
cagttcgtgg aaatggcggc agcacagctg gcatcaaac tgcgctttga aggcacgggc    840
gttgaagaga agggcattgt ggtttccgtc accgggcatg acgcgccggg cgttaaaccg    900
ggtgatgtga ttatcgctgt tgacccgcgt tacttccgtc cggctgaagt tgaaacgctg    960
ctcggcgacc cgaccaaagc gcacgaaaaa ctgggctgga accggaaat caccctcaga   1020 gagatggtgt ctgaaatggt ggctaatgac ctcgaagcgg cgaaaaaaca ctctctgctg   1080
aaatctcacg gctacgacgt ggcgatcgcg ctggagtcat aa                      1122
```

<210> SEQ ID NO 2
<211> LENGTH: 373
<212> TYPE: PRT
<213> ORGANISM: Escherichia coli

<400> SEQUENCE: 2

```
Met Ser Lys Val Ala Leu Ile Thr Gly Val Thr Gly Gln Asp Gly Ser
1               5                   10                  15

Tyr Leu Ala Glu Phe Leu Leu Glu Lys Gly Tyr Glu Val His Gly Ile
                20                  25                  30

Lys Arg Arg Ala Ser Ser Phe Asn Thr Glu Arg Val Asp His Ile Tyr
            35                  40                  45

Gln Asp Pro His Thr Cys Asn Pro Lys Phe His Leu His Tyr Gly Asp
        50                  55                  60

Leu Ser Asp Thr Ser Asn Leu Thr Arg Ile Leu Arg Glu Val Gln Pro
65                  70                  75                  80

Asp Glu Val Tyr Asn Leu Gly Ala Met Ser His Val Ala Val Ser Phe
                85                  90                  95

Glu Ser Pro Glu Tyr Thr Ala Asp Val Asp Ala Met Gly Thr Leu Arg
            100                 105                 110

Leu Leu Glu Ala Ile Arg Phe Leu Gly Leu Glu Lys Lys Thr Arg Phe
        115                 120                 125

Tyr Gln Ala Ser Thr Ser Glu Leu Tyr Gly Leu Val Gln Glu Ile Pro
    130                 135                 140

Gln Lys Glu Thr Thr Pro Phe Tyr Pro Arg Ser Pro Tyr Ala Val Ala
145                 150                 155                 160

Lys Leu Tyr Ala Tyr Trp Ile Thr Val Asn Tyr Arg Glu Ser Tyr Gly
                165                 170                 175

Met Tyr Ala Cys Asn Gly Ile Leu Phe Asn His Glu Ser Pro Arg Arg
            180                 185                 190

Gly Glu Thr Phe Val Thr Arg Lys Ile Thr Arg Ala Ile Ala Asn Ile
        195                 200                 205

Ala Gln Gly Leu Glu Ser Cys Leu Tyr Leu Gly Asn Met Asp Ser Leu
    210                 215                 220

Arg Asp Trp Gly His Ala Lys Asp Tyr Val Lys Met Gln Trp Met Met
225                 230                 235                 240

Leu Gln Gln Glu Gln Pro Glu Asp Phe Val Ile Ala Thr Gly Val Gln
                245                 250                 255

Tyr Ser Val Arg Gln Phe Val Glu Met Ala Ala Gln Leu Gly Ile
            260                 265                 270
```

```
Lys Leu Arg Phe Glu Gly Thr Gly Val Glu Glu Lys Gly Ile Val Val
            275                 280                 285

Ser Val Thr Gly His Asp Ala Pro Gly Val Lys Pro Gly Asp Val Ile
        290                 295                 300

Ile Ala Val Asp Pro Arg Tyr Phe Arg Pro Ala Glu Val Glu Thr Leu
305                 310                 315                 320

Leu Gly Asp Pro Thr Lys Ala His Glu Lys Leu Gly Trp Lys Pro Glu
                325                 330                 335

Ile Thr Leu Arg Glu Met Val Ser Glu Met Val Ala Asn Asp Leu Glu
            340                 345                 350

Ala Ala Lys Lys His Ser Leu Leu Lys Ser His Gly Tyr Asp Val Ala
        355                 360                 365

Ile Ala Leu Glu Ser
    370
```

<210> SEQ ID NO 3
<211> LENGTH: 1260
<212> TYPE: DNA
<213> ORGANISM: Escherichia coli

<400> SEQUENCE: 3

```
atgctaacat cctttaaact tcattcattg aaaccttaca ctctgaaatc atcaatgatt    60
ttagagataa taactatat attatgtttt ttttcaatga taattgcatt cgtcgataat   120
actttcagca taaaaatata taatatcact gctatagttt gcttattgtc actaatttta   180
cgtggcagac aagaaaatta taatataaaa aaccttattc ttcccctttc tatatttta   240
ataggcttgc ttgatttaat ttggtattct gcgtttaaag tagataattc gccatttcgt   300
gctacttacc atagttattt aaatactgcc aaaatattta tatttggttc ttttattgtt   360
ttcttgacac taactagcca gctaaaatca aaaaagaga gtgtattata cactttgtat   420
tctctgtcat ttctaattgc tggatatgca atgtatatta atagcattca tgaaaatgac   480
cgcatttctt ttggtgtagg aacggcaaca ggagcagcat attcaacaat gctaataggg   540
atagttagtg gcgttgcgat tctttatact aagaaaaatc atcctttttt attttatta   600
aatagttgcg cggtacttta tgttctggcg ctaacacaaa ccagagcaac cctactcctg   660
ttccctataa tttgtgttgc tgcattaata gcttattata taaatcacc caagaaattc   720
acttcctcta ttgttctact aattgctata ttagctagca ttgttattat atttaataaa   780
ccaatacaga atcgctataa tgaagcatta aatgacttaa acagttatac caatgctaat   840
agtgttactt ccctaggtgc aagactggca atgtacgaaa ttggtttaaa tatattcata   900
aagtcacctt tttcatttag atcagcagag tcacgcgctg aaagtatgaa tttgttagtt   960
gcagaacaca ataggctaag aggggcattg gagtttctca cgtacatcta acataatgag  1020
ataattgaag cagggtcact gaaaggtctg atgggaattt ttccacact tttcctctat  1080
tttcactat tttatatagc atataaaaaa cgagctttgg gtttgttgat attaacgctt  1140
ggcattgtgg ggattggact cagtgatgtg atcatatggg cacgcagcat tccaattatc  1200
attatatccg ctatagtcct cttactcgtc attaataatc gtaacaatac aattaattaa  1260
```

<210> SEQ ID NO 4
<211> LENGTH: 419
<212> TYPE: PRT
<213> ORGANISM: Escherichia coli

<400> SEQUENCE: 4

-continued

```
Met Leu Thr Ser Phe Lys Leu His Ser Leu Lys Pro Tyr Thr Leu Lys
1               5                   10                  15

Ser Ser Met Ile Leu Glu Ile Ile Thr Tyr Ile Leu Cys Phe Phe Ser
            20                  25                  30

Met Ile Ile Ala Phe Val Asp Asn Thr Phe Ser Ile Lys Ile Tyr Asn
            35                  40                  45

Ile Thr Ala Ile Val Cys Leu Leu Ser Leu Ile Leu Arg Gly Arg Gln
        50                  55                  60

Glu Asn Tyr Asn Ile Lys Asn Leu Ile Leu Pro Leu Ser Ile Phe Leu
65                  70                  75                  80

Ile Gly Leu Leu Asp Leu Ile Trp Tyr Ser Ala Phe Lys Val Asp Asn
                85                  90                  95

Ser Pro Phe Arg Ala Thr Tyr His Ser Tyr Leu Asn Thr Ala Lys Ile
            100                 105                 110

Phe Ile Phe Gly Ser Phe Ile Val Phe Leu Thr Leu Thr Ser Gln Leu
            115                 120                 125

Lys Ser Lys Lys Glu Ser Val Leu Tyr Thr Leu Tyr Ser Leu Ser Phe
130                 135                 140

Leu Ile Ala Gly Tyr Ala Met Tyr Ile Asn Ser Ile His Glu Asn Asp
145                 150                 155                 160

Arg Ile Ser Phe Gly Val Gly Thr Ala Thr Gly Ala Ala Tyr Ser Thr
                165                 170                 175

Met Leu Ile Gly Ile Val Ser Gly Val Ala Ile Leu Tyr Thr Lys Lys
            180                 185                 190

Asn His Pro Phe Leu Phe Leu Leu Asn Ser Cys Ala Val Leu Tyr Val
            195                 200                 205

Leu Ala Leu Thr Gln Thr Arg Ala Thr Leu Leu Phe Pro Ile Ile
210                 215                 220

Cys Val Ala Ala Leu Ile Ala Tyr Tyr Asn Lys Ser Pro Lys Lys Phe
225                 230                 235                 240

Thr Ser Ser Ile Val Leu Leu Ile Ala Ile Leu Ala Ser Ile Val Ile
            245                 250                 255

Ile Phe Asn Lys Pro Ile Gln Asn Arg Tyr Asn Glu Ala Leu Asn Asp
            260                 265                 270

Leu Asn Ser Tyr Thr Asn Ala Asn Ser Val Thr Ser Leu Gly Ala Arg
            275                 280                 285

Leu Ala Met Tyr Glu Ile Gly Leu Asn Ile Phe Ile Lys Ser Pro Phe
            290                 295                 300

Ser Phe Arg Ser Ala Glu Ser Arg Ala Glu Ser Met Asn Leu Leu Val
305                 310                 315                 320

Ala Glu His Asn Arg Leu Arg Gly Ala Leu Glu Phe Ser Asn Val His
                325                 330                 335

Leu His Asn Glu Ile Ile Glu Ala Gly Ser Leu Lys Gly Leu Met Gly
            340                 345                 350

Ile Phe Ser Thr Leu Phe Leu Tyr Phe Ser Leu Phe Tyr Ile Ala Tyr
            355                 360                 365

Lys Lys Arg Ala Leu Gly Leu Leu Ile Leu Thr Leu Gly Ile Val Gly
370                 375                 380

Ile Gly Leu Ser Asp Val Ile Ile Trp Ala Arg Ser Ile Pro Ile Ile
385                 390                 395                 400

Ile Ile Ser Ala Ile Val Leu Leu Val Ile Asn Asn Arg Asn
            405                 410                 415

Thr Ile Asn
```

<210> SEQ ID NO 5
<211> LENGTH: 2142
<212> TYPE: DNA
<213> ORGANISM: Campylobacter jejuni

<400> SEQUENCE: 5

| | | | | | |
|---|---|---|---|---|---|
| atgttgaaaa | aagagtattt | aaaaaaccct | tatttagttt | tgtttgcgat | gattgtatta | 60 |
| gcttatgttt | ttagtgtatt | ttgcaggttt | tattgggttt | ggtgggcaag | tgagtttaac | 120 |
| gagtatttt | tcaataatca | attaatgatc | atttcaaacg | atggctatgc | ttttgctgag | 180 |
| ggcgcaagag | atatgatagc | aggttttcat | cagcctaatg | atttgagtta | ttatggatct | 240 |
| tctttatcta | cgcttactta | tggctttat | aaaatcacac | cttttctctt | tgaaagtatc | 300 |
| attttatata | tgagtacttt | tttatcttct | ttggtggtga | ttcctattat | tttactagct | 360 |
| aatgaataca | aacgccctt | aatgggcttt | gtagctgctc | ttttagcaag | tgtagcaaac | 420 |
| agttattata | atcgcactat | gagtgggtat | tatgatacgg | atatgctggt | aattgtttta | 480 |
| cctatgttta | ttttattttt | tatggtaaga | atgattttaa | aaaagacttt | ttttcattg | 540 |
| attgccttgc | cattatttat | aggaatttat | ctttggtggt | atccttcaag | ttatacttta | 600 |
| aatgtagctt | taattggact | tttttaatt | tatacactta | tttttcatag | aaaagaaaag | 660 |
| atttttata | tagctgtgat | tttgtcttct | cttactcttt | caaatatagc | atggttttat | 720 |
| caaagtgcca | ttatagtaat | acttttttgct | ttatttgctt | tagagcaaaa | acgcttaaat | 780 |
| tttatgatta | taggaatttt | aggtagtgca | actttgatat | ttttgatttt | aagtggtggg | 840 |
| gttgatccca | tactttatca | gcttaaattt | tatattttta | gaagcgatga | aagtgcgaat | 900 |
| ttaacacagg | gctttatgta | ttttaatgtt | aatcaaacca | tacaagaagt | tgaaaatgta | 960 |
| gattttagcg | aatttatgcg | aagaattagt | ggtagtgaaa | ttgttttctt | gttttctttg | 1020 |
| tttggttttg | tatggctttt | gagaaaacat | aaaagtatga | ttatggcttt | acctatattg | 1080 |
| gtgcttgggt | ttttagcctt | aaaaggagga | cttagattta | ccatttattc | tgtacctgta | 1140 |
| atggctttag | gatttggttt | tttattgagc | gagtttaagg | ctatattggt | taaaaaatat | 1200 |
| agccaattaa | cttcaaatgt | ttgtattgtt | tttgcaacta | ttttgacttt | ggctccagta | 1260 |
| tttatccata | tttacaacta | taaagcgcca | acagttttt | ctcaaaatga | agcatcatta | 1320 |
| ttaaatcaat | taaaaaatat | agccaataga | aagattatg | tggtaacttg | gtgggattat | 1380 |
| ggttatcctg | tgcgttatta | tagcgatgtg | aaaactttag | tagatggtgg | aaagcattta | 1440 |
| ggtaaggata | atttttcc | ttcttttct | ttaagtaaag | atgaacaagc | tgcagctaat | 1500 |
| atggcaagac | ttagtgtaga | atatacagaa | aaaagctttt | atgctccgca | aaatgatatt | 1560 |
| ttaaaatcag | acatttaca | agccatgatg | aaagattata | atcaaagcaa | tgtggattta | 1620 |
| tttctagctt | cattatcaaa | acctgatttt | aaaatcgata | caccaaaaac | tcgtgatatt | 1680 |
| tatctttata | tgcccgctag | aatgtctttg | attttttcta | cggtggctag | tttttctttt | 1740 |
| attaatttag | atacaggagt | tttggataaa | cctttaccct | ttagcacagc | ttatccactt | 1800 |
| gatgttaaaa | atggagaaat | ttatcttagc | aacggagtgg | ttttaagcga | tgatttaga | 1860 |
| agttttaaaa | taggtgataa | tgtggtttct | gtaaatagta | tcgtagagat | taattctatt | 1920 |
| aaacaaggtg | aatacaaaat | cactccaatc | gatgataagg | ctcagtttta | tatttttat | 1980 |
| ttaaaggata | gtgctattcc | ttacgcacaa | tttattttaa | tggataaaac | catgtttaat | 2040 |
| agtgcttatg | tgcaaatgtt | tttttggga | aattatgata | agaatttatt | tgacttggtg | 2100 |

-continued attaattcta gagatgctaa agtttttaaa cttaaaattt aa         2142

<210> SEQ ID NO 6
<211> LENGTH: 713
<212> TYPE: PRT
<213> ORGANISM: Campylobacter jejuni

<400> SEQUENCE: 6

```
Met Leu Lys Lys Glu Tyr Leu Lys Asn Pro Tyr Leu Val Leu Phe Ala
1               5                   10                  15

Met Ile Val Leu Ala Tyr Val Phe Ser Val Phe Cys Arg Phe Tyr Trp
            20                  25                  30

Val Trp Trp Ala Ser Glu Phe Asn Glu Tyr Phe Asn Asn Gln Leu
        35                  40                  45

Met Ile Ile Ser Asn Asp Gly Tyr Ala Phe Ala Glu Gly Ala Arg Asp
    50                  55                  60

Met Ile Ala Gly Phe His Gln Pro Asn Asp Leu Ser Tyr Tyr Gly Ser
65                  70                  75                  80

Ser Leu Ser Thr Leu Thr Tyr Trp Leu Tyr Lys Ile Thr Pro Phe Ser
                85                  90                  95

Phe Glu Ser Ile Ile Leu Tyr Met Ser Thr Phe Leu Ser Ser Leu Val
            100                 105                 110

Val Ile Pro Ile Ile Leu Leu Ala Asn Glu Tyr Lys Arg Pro Leu Met
        115                 120                 125

Gly Phe Val Ala Ala Leu Leu Ala Ser Val Ala Asn Ser Tyr Tyr Asn
130                 135                 140

Arg Thr Met Ser Gly Tyr Tyr Asp Thr Asp Met Leu Val Ile Val Leu
145                 150                 155                 160

Pro Met Phe Ile Leu Phe Phe Met Val Arg Met Ile Leu Lys Lys Asp
                165                 170                 175

Phe Phe Ser Leu Ile Ala Leu Pro Leu Phe Ile Gly Ile Tyr Leu Trp
            180                 185                 190

Trp Tyr Pro Ser Ser Tyr Thr Leu Asn Val Ala Leu Ile Gly Leu Phe
        195                 200                 205

Leu Ile Tyr Thr Leu Ile Phe His Arg Lys Glu Lys Ile Phe Tyr Ile
    210                 215                 220

Ala Val Ile Leu Ser Ser Leu Thr Leu Ser Asn Ile Ala Trp Phe Tyr
225                 230                 235                 240

Gln Ser Ala Ile Ile Val Ile Leu Phe Ala Leu Phe Ala Leu Glu Gln
                245                 250                 255

Lys Arg Leu Asn Phe Met Ile Ile Gly Ile Leu Gly Ser Ala Thr Leu
            260                 265                 270

Ile Phe Leu Ile Leu Ser Gly Gly Val Asp Pro Ile Leu Tyr Gln Leu
        275                 280                 285

Lys Phe Tyr Ile Phe Arg Ser Asp Glu Ser Ala Asn Leu Thr Gln Gly
    290                 295                 300

Phe Met Tyr Phe Asn Val Asn Gln Thr Ile Gln Glu Val Glu Asn Val
305                 310                 315                 320

Asp Phe Ser Glu Phe Met Arg Arg Ile Ser Gly Ser Glu Ile Val Phe
                325                 330                 335

Leu Phe Ser Leu Phe Gly Phe Val Trp Leu Leu Arg Lys His Lys Ser
            340                 345                 350

Met Ile Met Ala Leu Pro Ile Leu Val Leu Gly Phe Leu Ala Leu Lys
        355                 360                 365
```

```
Gly Gly Leu Arg Phe Thr Ile Tyr Ser Val Pro Val Met Ala Leu Gly
    370                 375                 380

Phe Gly Phe Leu Leu Ser Glu Phe Lys Ala Ile Leu Val Lys Lys Tyr
385                 390                 395                 400

Ser Gln Leu Thr Ser Asn Val Cys Ile Val Phe Ala Thr Ile Leu Thr
                405                 410                 415

Leu Ala Pro Val Phe Ile His Ile Tyr Asn Tyr Lys Ala Pro Thr Val
            420                 425                 430

Phe Ser Gln Asn Glu Ala Ser Leu Leu Asn Gln Leu Lys Asn Ile Ala
        435                 440                 445

Asn Arg Glu Asp Tyr Val Val Thr Trp Trp Asp Tyr Gly Tyr Pro Val
    450                 455                 460

Arg Tyr Tyr Ser Asp Val Lys Thr Leu Val Asp Gly Gly Lys His Leu
465                 470                 475                 480

Gly Lys Asp Asn Phe Phe Pro Ser Phe Ser Leu Ser Lys Asp Glu Gln
                485                 490                 495

Ala Ala Ala Asn Met Ala Arg Leu Ser Val Glu Tyr Thr Glu Lys Ser
            500                 505                 510

Phe Tyr Ala Pro Gln Asn Asp Ile Leu Lys Ser Asp Ile Leu Gln Ala
        515                 520                 525

Met Met Lys Asp Tyr Asn Gln Ser Asn Val Asp Leu Phe Leu Ala Ser
    530                 535                 540

Leu Ser Lys Pro Asp Phe Lys Ile Asp Thr Pro Lys Thr Arg Asp Ile
545                 550                 555                 560

Tyr Leu Tyr Met Pro Ala Arg Met Ser Leu Ile Phe Ser Thr Val Ala
                565                 570                 575

Ser Phe Ser Phe Ile Asn Leu Asp Thr Gly Val Leu Asp Lys Pro Phe
            580                 585                 590

Thr Phe Ser Thr Ala Tyr Pro Leu Asp Val Lys Asn Gly Glu Ile Tyr
        595                 600                 605

Leu Ser Asn Gly Val Val Leu Ser Asp Asp Phe Arg Ser Phe Lys Ile
    610                 615                 620

Gly Asp Asn Val Val Ser Val Asn Ser Ile Val Glu Ile Asn Ser Ile
625                 630                 635                 640

Lys Gln Gly Glu Tyr Lys Ile Thr Pro Ile Asp Asp Lys Ala Gln Phe
                645                 650                 655

Tyr Ile Phe Tyr Leu Lys Asp Ser Ala Ile Pro Tyr Ala Gln Phe Ile
            660                 665                 670

Leu Met Asp Lys Thr Met Phe Asn Ser Ala Tyr Val Gln Met Phe Phe
        675                 680                 685

Leu Gly Asn Tyr Asp Lys Asn Leu Phe Asp Leu Val Ile Asn Ser Arg
    690                 695                 700

Asp Ala Lys Val Phe Lys Leu Lys Ile
705                 710

<210> SEQ ID NO 7
<211> LENGTH: 364
<212> TYPE: PRT
<213> ORGANISM: Haemophilus influenzae

<400> SEQUENCE: 7

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30
```

Ser Asp Lys Ile Ile Ile Ala His Arg Gly Ala Ser Gly Tyr Leu Pro
        35                  40                  45

Glu His Thr Leu Glu Ser Lys Ala Leu Ala Phe Ala Gln Gln Ala Asp
 50                  55                  60

Tyr Leu Glu Gln Asp Leu Ala Met Thr Lys Asp Gly Arg Leu Val Val
 65                  70                  75                  80

Ile His Asp His Phe Leu Asp Gly Leu Thr Asp Val Ala Lys Lys Phe
                 85                  90                  95

Pro His Arg His Arg Lys Asp Gly Arg Tyr Tyr Val Ile Asp Phe Thr
            100                 105                 110

Leu Lys Glu Ile Gln Ser Leu Met Thr Glu Asn Phe Glu Thr Lys
        115                 120                 125

Asp Gly Lys Gln Ala Gln Val Tyr Pro Asn Arg Phe Pro Leu Trp Lys
        130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
        195                 200                 205

Val Tyr Leu Gln Thr Phe Asp Phe Asn Glu Leu Lys Arg Ile Lys Thr
    210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
        275                 280                 285

Val Asn Lys Glu Glu Ser Lys Pro Asp Asn Ile Val Tyr Thr Pro Leu
    290                 295                 300

Val Lys Glu Leu Ala Gln Tyr Asn Val Glu Val His Pro Tyr Thr Val
305                 310                 315                 320

Arg Lys Asp Ala Leu Pro Ala Phe Phe Thr Asp Val Asn Gln Met Tyr
                325                 330                 335

Asp Val Leu Leu Asn Lys Ser Gly Ala Thr Gly Val Phe Thr Asp Phe
            340                 345                 350

Pro Asp Thr Gly Val Glu Phe Leu Lys Gly Ile Lys
        355                 360

<210> SEQ ID NO 8
<211> LENGTH: 386
<212> TYPE: PRT
<213> ORGANISM: Neisseria meningitidis

<400> SEQUENCE: 8

Met Arg Lys Lys Leu Thr Ala Leu Val Leu Ser Ala Leu Pro Leu Ala
1               5                   10                  15

Ala Val Ala Asp Val Ser Leu Tyr Gly Glu Ile Lys Ala Gly Val Glu
            20                  25                  30

Gly Arg Asn Ile Gln Leu Gln Leu Thr Glu Gln Pro Ser Lys Ala Gln

```
                   35                  40                  45
Gly Gln Thr Asn Asn Gln Val Lys Val Thr Lys Ala Lys Ser Arg Ile
 50                  55                  60

Arg Thr Lys Ile Ser Asp Phe Gly Ser Phe Ile Gly Phe Lys Gly Ser
 65                  70                  75                  80

Glu Asp Leu Gly Glu Leu Lys Ala Val Trp Gln Leu Glu Gln Asp
                     85                  90                  95

Val Ser Val Ala Gly Gly Ala Thr Gln Trp Gly Asn Arg Glu Ser
                    100                 105                 110

Phe Ile Gly Leu Ala Gly Glu Phe Gly Thr Leu Arg Ala Gly Arg Val
                    115                 120                 125

Ala Asn Gln Phe Asp Asp Ala Ser Gln Ala Ile Asp Pro Trp Asp Ser
130                 135                 140

Asn Asn Asp Val Ala Ser Gln Leu Gly Ile Phe Lys Arg His Asp Asp
145                 150                 155                 160

Met Pro Val Ser Val Arg Tyr Asp Ser Pro Asp Phe Ser Gly Phe Ser
                    165                 170                 175

Gly Ser Val Gln Phe Val Pro Ala Gln Asn Ser Lys Ser Ala Tyr Thr
                    180                 185                 190

Pro Ala Tyr Val Asp Glu Lys Gln Val Ser His Ala Ala Val Val Gly
                    195                 200                 205

Lys Pro Gly Ser Asp Val Tyr Tyr Ala Gly Leu Asn Tyr Lys Asn Gly
210                 215                 220

Gly Phe Ala Gly Ser Tyr Ala Phe Lys Tyr Ala Lys His Ala Asn Glu
225                 230                 235                 240

Gly Arg Asp Ala Phe Phe Leu Phe Leu Leu Gly Ser Gly Ser Asp Glu
                    245                 250                 255

Ala Lys Gly Thr Asp Pro Leu Lys Asn His Gln Val His Arg Leu Thr
                    260                 265                 270

Gly Gly Tyr Glu Glu Gly Gly Leu Asn Leu Ala Leu Ala Ala Gln Leu
                    275                 280                 285

Asp Leu Ser Glu Asn Ala Asp Lys Thr Lys Asn Ser Thr Thr Glu Ile
290                 295                 300

Ala Ala Thr Ala Ser Tyr Arg Phe Gly Asn Ala Val Pro Arg Ile Ser
305                 310                 315                 320

Tyr Ala His Gly Phe Asp Phe Ile Glu Arg Gly Lys Lys Gly Glu Asn
                    325                 330                 335

Thr Ser Tyr Asp Gln Ile Ile Ala Gly Val Asp Tyr Asp Phe Ser Lys
                    340                 345                 350

Arg Thr Ser Ala Ile Val Ser Gly Ala Trp Leu Lys Arg Asn Thr Gly
                    355                 360                 365

Ile Gly Asn Tyr Thr Gln Ile Asn Ala Ala Ser Val Gly Leu Arg His
                    370                 375                 380

Lys Phe
385

<210> SEQ ID NO 9
<211> LENGTH: 560
<212> TYPE: PRT
<213> ORGANISM: Corynebacterium diphtheriae

<400> SEQUENCE: 9

Met Ser Arg Lys Leu Phe Ala Ser Ile Leu Ile Gly Ala Leu Leu Gly
  1

-continued

```
Ile Gly Ala Pro Pro Ser Ala His Ala Gly Ala Asp Asp Val Val Asp
            20              25              30

Ser Ser Lys Ser Phe Val Met Glu Asn Phe Ser Ser Tyr His Gly Thr
        35              40              45

Lys Pro Gly Tyr Val Asp Ser Ile Gln Lys Gly Ile Gln Lys Pro Lys
    50              55              60

Ser Gly Thr Gln Gly Asn Tyr Asp Asp Asp Trp Lys Gly Phe Tyr Ser
65              70              75              80

Thr Asp Asn Lys Tyr Asp Ala Ala Gly Tyr Ser Val Asp Asn Glu Asn
                85              90              95

Pro Leu Ser Gly Lys Ala Gly Val Val Lys Val Thr Tyr Pro Gly
            100             105             110

Leu Thr Lys Val Leu Ala Leu Lys Val Asp Asn Ala Glu Thr Ile Lys
        115             120             125

Lys Glu Leu Gly Leu Ser Leu Thr Glu Pro Leu Met Glu Gln Val Gly
    130             135             140

Thr Glu Glu Phe Ile Lys Arg Phe Gly Asp Gly Ala Ser Arg Val Val
145             150             155             160

Leu Ser Leu Pro Phe Ala Glu Gly Ser Ser Val Glu Tyr Ile Asn
                165             170             175

Asn Trp Glu Gln Ala Lys Ala Leu Ser Val Glu Leu Glu Ile Asn Phe
            180             185             190

Glu Thr Arg Gly Lys Arg Gly Gln Asp Ala Met Tyr Glu Tyr Met Ala
        195             200             205

Gln Ala Cys Ala Gly Asn Arg Val Arg Arg Ser Val Gly Ser Ser Leu
    210             215             220

Ser Cys Ile Asn Leu Asp Trp Asp Val Ile Arg Asp Lys Thr Lys Thr
225             230             235             240

Lys Ile Glu Ser Leu Lys Glu His Gly Pro Ile Lys Asn Lys Met Ser
                245             250             255

Glu Ser Pro Asn Lys Thr Val Ser Glu Glu Lys Ala Lys Gln Tyr Leu
            260             265             270

Glu Glu Phe His Gln Thr Ala Leu Glu His Pro Glu Leu Ser Glu Leu
        275             280             285

Lys Thr Val Thr Gly Thr Asn Pro Val Phe Ala Gly Ala Asn Tyr Ala
    290             295             300

Ala Trp Ala Val Asn Val Ala Gln Val Ile Asp Ser Glu Thr Ala Asp
305             310             315             320

Asn Leu Glu Lys Thr Thr Ala Ala Leu Ser Ile Leu Pro Gly Ile Gly
                325             330             335

Ser Val Met Gly Ile Ala Asp Gly Ala Val His His Asn Thr Glu Glu
            340             345             350

Ile Val Ala Gln Ser Ile Ala Leu Ser Ser Leu Met Val Ala Gln Ala
        355             360             365

Ile Pro Leu Val Gly Glu Leu Val Asp Ile Gly Phe Ala Ala Tyr Asn
    370             375             380

Phe Val Glu Ser Ile Ile Asn Leu Phe Gln Val Val His Asn Ser Tyr
385             390             395             400

Asn Arg Pro Ala Tyr Ser Pro Gly His Lys Thr Gln Pro Phe Leu His
                405             410             415

Asp Gly Tyr Ala Val Ser Trp Asn Thr Val Glu Asp Ser Ile Ile Arg
            420             425             430

Thr Gly Phe Gln Gly Glu Ser Gly His Asp Ile Lys Ile Thr Ala Glu
```

```
                435                 440                 445
Asn Thr Pro Leu Pro Ile Ala Gly Val Leu Pro Thr Ile Pro Gly
450                 455                 460

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
                485                 490                 495

Arg Pro Lys Ser Pro Val Tyr Val Gly Asn Gly Val His Ala Asn Leu
                500                 505                 510

His Val Ala Phe His Arg Ser Ser Glu Lys Ile His Ser Asn Glu
515                 520                 525

Ile Ser Ser Asp Ser Ile Gly Val Leu Gly Tyr Gln Lys Thr Val Asp
530                 535                 540

His Thr Lys Val Asn Ser Lys Leu Ser Leu Phe Phe Glu Ile Lys Ser
545                 550                 555                 560

<210> SEQ ID NO 10
<211> LENGTH: 451
<212> TYPE: PRT
<213> ORGANISM: Clostridium tetani

<400> SEQUENCE: 10

Lys Asn Leu Asp Cys Trp Val Asp Asn Glu Asp Ile Asp Val Ile
1               5                   10                  15

Leu Lys Lys Ser Thr Ile Leu Asn Leu Asp Ile Asn Asn Asp Ile Ile
                20                  25                  30

Ser Asp Ile Ser Gly Phe Asn Ser Ser Val Ile Thr Tyr Pro Asp Ala
            35                  40                  45

Gln Leu Val Pro Gly Ile Asn Gly Lys Ala Ile His Leu Val Asn Asn
50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255
```

```
Pro Leu Arg Tyr Asp Thr Glu Tyr Tyr Leu Ile Pro Val Ala Ser Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
        290                 295                 300

Leu Tyr Asn Gly Leu Lys Phe Ile Ile Lys Arg Tyr Thr Pro Asn Asn
305                 310                 315                 320

Glu Ile Asp Ser Phe Val Lys Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350

Ala Phe Asn Asn Leu Asp Arg Ile Leu Arg Val Gly Tyr Asn Ala Pro
            355                 360                 365

Gly Ile Pro Leu Tyr Lys Lys Met Glu Ala Val Lys Leu Arg Asp Leu
        370                 375                 380

Lys Thr Tyr Ser Val Gln Leu Lys Leu Tyr Asp Asp Lys Asn Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430

Lys Ile Leu Gly Cys Asp Trp Tyr Phe Val Pro Thr Asp Glu Gly Trp
            435                 440                 445

Thr Asn Asp
    450

<210> SEQ ID NO 11
<211> LENGTH: 5
<212> TYPE: PRT
<213> ORGANISM: Artificial Sequence
<220> FEATURE:
<223> OTHER INFORMATION: Synthetic- glycosylation tag

<400> SEQUENCE: 11

Asp Gln Asn Ala Thr
1               5

<210> SEQ ID NO 12
<211> LENGTH: 20
<212> TYPE: PRT
<213> ORGANISM: Artificial Sequence
<220> FEATURE:
<223> OTHER INFORMATION: Synthetic- 4x DQNAT glycosylation tag

<400> SEQUENCE: 12

Asp Gln Asn Ala Thr Asp Gln Asn Ala Thr Asp Gln Asn Ala Thr Asp
1               5                   10                  15

Gln Asn Ala Thr
            20
```

COMPOSITIONS AND METHODS FOR RAPID IN VITRO SYNTHESIS OF BIOCONJUGATE VACCINES IN VITRO VIA PRODUCTION AND N-GLYCOSYLATION OF PROTEIN CARRIERS IN DETOXIFIED PROKARYOTIC CELL LYSATES

CROSS-REFERENCE TO RELATED PATENT APPLICATIONS

The present application claims the benefit of priority under 35 U.S.C. § 119(e) to U.S. Provisional Application No. 62/791,425, filed on Jan. 11, 2019 and to U.S. Provisional Application No. 62/644,811, filed on Mar. 19, 2018, the contents of which are incorporated herein by reference in their entireties.

STATEMENT REGARDING FEDERALLY SPONSORED RESEARCH OR DEVELOPMENT

This invention was made with government support under MCB1413563 awarded by the National Science Foundation and HDTRA1-15-1-0052 awarded by the Department of Defense. The government has certain rights in the invention.

SEQUENCE LISTING

A Sequence Listing accompanies this application and is submitted as an ASCII text file of the sequence listing named "702581_00836_ST25.txt" which is 35,544 bytes in size and was created on Apr. 20, 2022. The sequence listing is electronically submitted via EFS-Web with the application and is incorporated herein by reference in its entirety.

BACKGROUND

The field of the invention relates to in vitro synthesis of N-glycosylated protein in prokaryotic cell lysates. In particular, the field of the invention relates to the use of N-glycosylated proteins synthesized in vitro in prokaryotic cell lysates as vaccine conjugates against pathogens such as bacteria.

Conjugate vaccines are among the safest and most effective methods for prevention of life-threatening bacterial infections. Bioconjugate vaccines are a type of conjugate vaccine produced via protein glycan coupling technology (PGCT), in which polysaccharide antigens are conjugated via N-glycosylation to recombinant carrier proteins using a bacterial oligosaccharyltransferase (OST) in living *Escherichia coli* cells. Bioconjugate vaccines have the potential to greatly reduce the time and cost required to produce antibacterial vaccines. However, PGCT is limited by: i) the length of in vivo process development timelines; and ii) the fact that FDA-approved carrier proteins, such as the toxins from *Clostridium tetani* and *Corynebacterium diptheriae*, have not yet been demonstrated to be compatible with N-linked glycosylation in living *E. coli*. Here, we have applied cell-free glycoprotein synthesis (CFGpS) technology to enable rapid in vitro production of bioconjugate vaccines against pathogenic strains of *Escherichia coli* and *Franscicella tularensis* in reactions lasting 20 hours. Due to the modular nature of the CFGpS system, this cell-free strategy could be easily applied to produce bioconjugates using FDA-approved carrier proteins or additional vaccines against pathogenic bacteria whose surface antigen gene clusters are known. We further show that this system can be lyophilized and retain bioconjugate synthesis capability, demonstrating the potential for on-demand vaccine production and development in resource-poor settings. This work represents the first demonstration of bioconjugate vaccine production in *E. coli* lysates and has promising applications as a portable prototyping or production platform for antibacterial vaccine candidates.

SUMMARY

Disclosed are methods, systems, components, and compositions for cell-free synthesis of glycosylated carrier proteins. The glycosylated carrier proteins may be utilized in vaccines, including anti-bacterial vaccines.

The glycosylated carrier proteins may include a bacterial polysaccharide conjugated to a carrier, which may be utilized to generate an immune response in an immunized host against the polysaccharide conjugated to the carrier. Suitable carriers may include but are not limited to *Haemophilus influenzae* protein D (PD), *Neisseria meningitidis* porin protein (PorA), *Corynebacterium diphtherias* toxin (CRM197), *Clostridium tetani* toxin (TT), and *Escherichia coli* maltose binding protein, or variants thereof.

The glycosylated carrier proteins may be synthesized in cell-free glycoprotein synthesis (CFGpS) systems using detoxified prokaryote cell lysates that are enriched in components for glycoprotein synthesis such as oligosaccharyltransferases (OSTs) and lipid-linked oligosaccharides (LLOs) including OSTs and. LLOs associated with synthesis of bacterial O-antigens. As such, the prokaryote cell lysates may be prepared from recombinant prokaryotes that have been engineered to express detoxified lipid A, and recombinant prokaryotes that have been engineered to express heterologous OSTs and/or that have been engineered to express heterologous glycan synthesis pathways for production of LLOs. The disclosed lysates may be described as modular and may be combined to prepare glycosylated proteins in the disclosed CFGpS systems.

DETAILED DESCRIPTION

Figure 1:
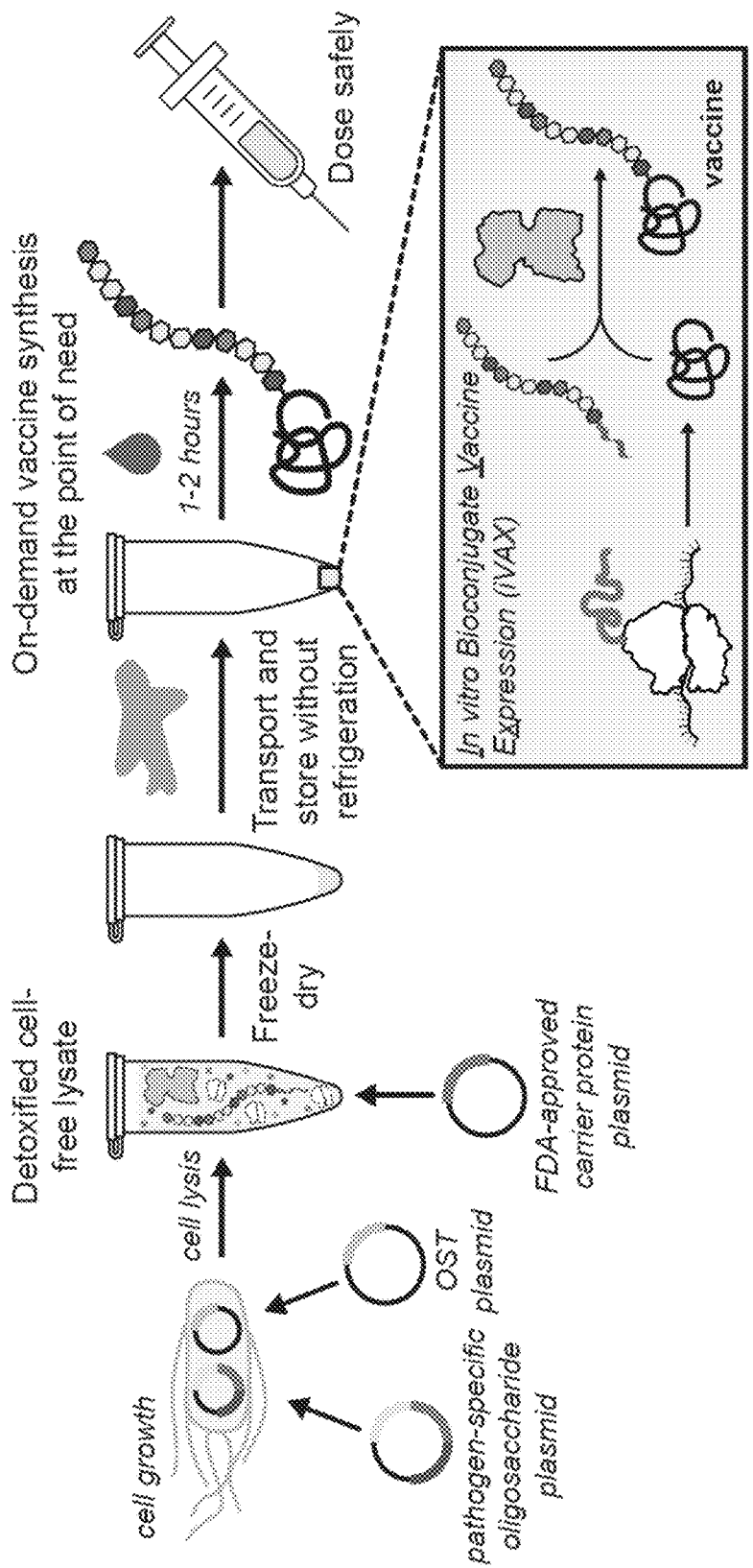
FIG. 1. WAX platform enables on-demand and portable production of antibacterial vaccines. The in vitro bioconjugate vaccine expression (iVAX) platform provides a rapid means to develop and distribute antibacterial vaccines in the event of a pathogen outbreak. Expression of pathogen-specific polysaccharides (e.g., CPS, LPS) and a bacterial oligosaccharyltransferases enzyme in engineered strains with detoxified lipid A yields low-endotoxin lysates containing all of the machinery required for synthesis of bioconjugate vaccines. Reactions catalyzed by iVAX lysates can be used to produce bioconjugates containing FDA-approved carrier proteins and can be freeze-dried without loss of activity for refrigeration-free transportation and storage. Freeze-dried reactions can be activated at the point of need via simple rehydration and reproducibly synthesize immunologically active bioconjugates in ~1 h.

The present invention is described herein using several definitions, as set forth below and throughout the application.

Definitions

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "a gene" or "an oligosaccharide" should be interpreted to mean "one or more genes" and "one or more oligosaccharides," respectively, unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into ranges and subranges. A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

As used herein, the terms "bind," "binding," "interact," "interacting," "occupy" and "occupying" refer to covalent interactions, noncovalent interactions and steric interactions. A covalent interaction is a chemical linkage between two atoms or radicals formed by the sharing of a pair of electrons (a single bond), two pairs of electrons (a double bond) or three pairs of electrons (a triple bond). Covalent interactions are also known in the art as electron pair interactions or electron pair bonds. Noncovalent interactions include, but are not limited to, van der Waals interactions, hydrogen bonds, weak chemical bonds (via short-range noncovalent forces), hydrophobic interactions, ionic bonds and the like. A review of noncovalent interactions can be found in Alberts et al., in Molecular Biology of the Cell, 3d edition, Garland Publishing, 1994. Steric interactions are generally understood to include those where the structure of the compound is such that it is capable of occupying a site by virtue of its three dimensional structure, as opposed to any attractive forces between the compound and the site.

Polynucleotides and Synthesis Methods

The terms "nucleic acid" and "oligonucleotide," as used herein, refer to polydeoxyribonucleotides (containing 2-deoxy-D-ribose), polyribonucleotides (containing D-ribose), and to any other type of polynucleotide that is an N glycoside of a purine or pyrimidine base. There is no intended distinction in length between the terms "nucleic acid", "oligonucleotide" and "polynucleotide", and these terms will be used interchangeably. These terms refer only to the primary structure of the molecule. Thus, these terms include double- and single-stranded DNA, as well as double- and single-stranded RNA. For use in the present methods, an oligonucleotide also can comprise nucleotide analogs in which the base, sugar, or phosphate backbone is modified as well as non-purine or non-pyrimidine nucleotide analogs.

Oligonucleotides can be prepared by any suitable method, including direct chemical synthesis by a method such as the phosphotriester method of Narang et al., 1979, *Meth. Enzymol.* 68:90-99; the phosphodiester method of Brown et al., 1979, *Meth. Enzymol.* 68:109-151; the diethylphosphoramidite method of Beaucage et al., 1981, *Tetrahedron Letters* 22:1859-1862; and the solid support method of U.S. Pat. No. 4,458,066, each incorporated herein by reference. A review of synthesis methods of conjugates of oligonucleotides and modified nucleotides is provided in Goodchild, 1990, *Bioconjugate Chemistry* 1(3): 165-187, incorporated herein by reference.

The term "amplification reaction" refers to any chemical reaction, including an enzymatic reaction, which results in increased copies of a template nucleic acid sequence or results in transcription of a template nucleic acid Amplification reactions include reverse transcription, the polymerase chain reaction (PCR), including Real Time PCR (see U.S. Pat. Nos. 4,683,195 and 4,683,202; PCR Protocols: A Guide to Methods and Applications (Innis et al., eds, 1990)), and the ligase chain reaction (LCR) (see Barany et al., U.S. Pat. No. 5,494,810). Exemplary "amplification reactions conditions" or "amplification conditions" typically comprise either two or three step cycles. Two-step cycles have a high temperature denaturation step followed by a hybridization/elongation (or ligation) step. Three step cycles comprise a denaturation step followed by a hybridization step followed by a separate elongation step.

The terms "target," "target sequence", "target region", and "target nucleic acid," as used herein, are synonymous and refer to a region or sequence of a nucleic acid which is to be amplified, sequenced, or detected.

The term "hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch. Conditions under which hybridization of fully complementary nucleic acid strands is strongly preferred are referred to as "stringent hybridization conditions" or "sequence-specific hybridization conditions". Stable duplexes of substantially complementary sequences can be achieved under less stringent hybridization conditions;

the degree of mismatch tolerated can be controlled by suitable adjustment of the hybridization conditions. Those skilled in the art of nucleic acid technology can determine duplex stability empirically considering a number of variables including, for example, the length and base pair composition of the oligonucleotides, ionic strength, and incidence of mismatched base pairs, following the guidance provided by the art (see, e.g., Sambrook et al., 1989, Molecular Cloning—A Laboratory Manual, Cold Spring Harbor Laboratory, Cold Spring Harbor, N.Y.; Wetmur, 1991, Critical Review in Biochem. and Mol. Biol. 26(3/4): 227-259; and Owczarzy et al., 2008, *Biochemistry*, 47: 5336-5353, which are incorporated herein by reference).

The term "primer," as used herein, refers to an oligonucleotide capable of acting as a point of initiation of DNA synthesis under suitable conditions. Such conditions include those in which synthesis of a primer extension product complementary to a nucleic acid strand is induced in the presence of four different nucleoside triphosphates and an agent for extension (for example, a DNA polymerase or reverse transcriptase) in an appropriate buffer and at a suitable temperature.

A primer is preferably a single-stranded DNA. The appropriate length of a primer depends on the intended use of the primer but typically ranges from about 6 to about 225 nucleotides, including intermediate ranges, such as from 15 to 35 nucleotides, from 18 to 75 nucleotides and from 25 to 150 nucleotides. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

Primers can incorporate additional features which allow for the detection or immobilization of the primer but do not alter the basic property of the primer, that of acting as a point of initiation of DNA synthesis. For example, primers may contain an additional nucleic acid sequence at the 5' end which does not hybridize to the target nucleic acid, but which facilitates cloning or detection of the amplified product, or which enables transcription of RNA (for example, by inclusion of a promoter) or translation of protein (for example, by inclusion of a 5'-UTR, such as an Internal Ribosome Entry Site (IRES) or a 3'-UTR element, such as a poly(A)$_n$ sequence, where $n$ is in the range from about 20 to about 200). The region of the primer that is sufficiently complementary to the template to hybridize is referred to herein as the hybridizing region.

As used herein, a primer is "specific," for a target sequence if, when used in an amplification reaction under sufficiently stringent conditions, the primer hybridizes primarily to the target nucleic acid. Typically, a primer is specific for a target sequence if the primer-target duplex stability is greater than the stability of a duplex formed between the primer and any other sequence found in the sample. One of skill in the art will recognize that various factors, such as salt conditions as well as base composition of the primer and the location of the mismatches, will affect the specificity of the primer, and that routine experimental confirmation of the primer specificity will be needed in many cases. Hybridization conditions can be chosen under which the primer can form stable duplexes only with a target sequence. Thus, the use of target-specific primers under suitably stringent amplification conditions enables the selective amplification of those target sequences that contain the target primer binding sites.

As used herein, a "polymerase" refers to an enzyme that catalyzes the polymerization of nucleotides. "DNA polymerase" catalyzes the polymerization of deoxyribonucleotides. Known DNA polymerases include, for example, *Pyrococcus furiosus* (Pfu) DNA polymerase, *E. coli* DNA polymerase I, T7 DNA polymerase and *Thermus aquaticus* (Taq) DNA polymerase, among others. "RNA polymerase" catalyzes the polymerization of ribonucleotides. The foregoing examples of DNA polymerases are also known as DNA-dependent DNA polymerases. RNA-dependent DNA polymerases also fall within the scope of DNA polymerases. Reverse transcriptase, which includes viral polymerases encoded by retroviruses, is an example of an RNA-dependent DNA polymerase. Known examples of RNA polymerase ("RNAP") include, for example, T3 RNA polymerase, T7 RNA polymerase, SP6 RNA polymerase and *E. coli* RNA polymerase, among others. The foregoing examples of RNA polymerases are also known as DNA-dependent RNA polymerase. The polymerase activity of any of the above enzymes can be determined by means well known in the art.

The term "promoter" refers to a cis-acting DNA sequence that directs RNA polymerase and other trans-acting transcription factors to initiate RNA transcription from the DNA template that includes the cis-acting DNA sequence.

As used herein, the term "sequence defined biopolymer" refers to a biopolymer having a specific primary sequence. A sequence defined biopolymer can be equivalent to a genetically-encoded defined biopolymer in cases where a gene encodes the biopolymer having a specific primary sequence.

As used herein, "expression template" and/or "transcription template" refers to a nucleic acid that serves as substrate for transcribing at least one RNA that can be translated into a sequence defined biopolymer (e.g., a polypeptide or protein). Expression templates include nucleic acids composed of DNA or RNA. Suitable sources of DNA for use a nucleic acid for an expression template include genomic DNA, cDNA and RNA that can be converted into cDNA. Genomic DNA, cDNA and RNA can be from any biological source, such as a tissue sample, a biopsy, a swab, sputum, a blood sample, a fecal sample, a urine sample, a scraping, among others. The genomic DNA, cDNA and RNA can be from host cell or virus origins and from any species, including extant and extinct organisms. As used herein, "expression template" and "transcription template" have the same meaning and are used interchangeably.

In certain exemplary embodiments, vectors such as, for example, expression vectors, containing a nucleic acid encoding one or more rRNAs or reporter polypeptides and/or proteins described herein are provided. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Such vectors are referred to herein as "expression vectors." In general, expression vectors of utility in recombinant DNA techniques are often in the form of plasmids. In the present specification, "plasmid" and "vector" can be used interchangeably. However, the disclosed methods and compositions are intended to include such other forms of expression vectors, such as viral vectors (e.g., replication defective retroviruses, adenoviruses and adeno-associated viruses), which serve equivalent functions.

In certain exemplary embodiments, the recombinant expression vectors comprise a nucleic acid sequence (e.g., a nucleic acid sequence encoding one or more rRNAs or reporter polypeptides and/or proteins described herein) in a form suitable for expression of the nucleic acid sequence in one or more of the methods described herein, which means that the recombinant expression vectors include one or more regulatory sequences which is operatively linked to the nucleic acid sequence to be expressed. Within a recombinant expression vector, "operably linked" is intended to mean that the nucleotide sequence encoding one or more rRNAs or reporter polypeptides and/or proteins described herein is linked to the regulatory sequence(s) in a manner which allows for expression of the nucleotide sequence (e.g., in an in vitro transcription and/or translation system). The term "regulatory sequence" is intended to include promoters, enhancers and other expression control elements (e.g., polyadenylation signals). Such regulatory sequences are described, for example, in Goeddel; Gene Expression Technology: Methods in Enzymology 185, Academic Press, San Diego, Calif. (1990).

Oligonucleotides and polynucleotides may optionally include one or more non-standard nucleotide(s), nucleotide analog(s) and/or modified nucleotides. Examples of modified nucleotides include, but are not limited to diaminopurine, $S^2T$, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, 2,6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

As utilized herein, a "deletion" means the removal of one or more nucleotides relative to the native polynucleotide sequence. The engineered strains that are disclosed herein may include a deletion in one or more genes (e.g., a deletion in gmd and/or a deletion in waaL). Preferably, a deletion results in a non-functional gene product. As utilized herein, an "insertion" means the addition of one or more nucleotides to the native polynucleotide sequence. The engineered strains that are disclosed herein may include an insertion in one or more genes (e.g., an insertion in gmd and/or an insertion in waaL). Preferably, a deletion results in a non-functional gene product. As utilized herein, a "substitution" means replacement of a nucleotide of a native polynucleotide sequence with a nucleotide that is not native to the polynucleotide sequence. The engineered strains that are disclosed herein may include a substitution in one or more genes (e.g., a substitution in gmd and/or a substitution in waaL). Preferably, a substitution results in a non-functional gene product, for example, where the substitution introduces a premature stop codon (e.g., TAA, TAG, or TGA) in the coding sequence of the gene product. In some embodiments, the engineered strains that are disclosed herein may include two or more substitutions where the substitutions introduce multiple premature stop codons (e.g., TAATAA, TAGTAG, or TGATGA).

In some embodiments, the engineered strains disclosed herein may be engineered to include and express one or heterologous genes. As would be understood in the art, a heterologous gene is a gene that is not naturally present in the engineered strain as the strain occurs in nature. A gene that is heterologous to *E. coli* is a gene that does not occur in *E. coli* and may be a gene that occurs naturally in another microorganism (e.g. a gene from *C. jejuni*) or a gene that does not occur naturally in any other known microorganism (i.e., an artificial gene).

Peptides, Polypeptides, Proteins, and Synthesis Methods

As used herein, the terms "peptide," "polypeptide," and "protein," refer to molecules comprising a chain a polymer of amino acid residues joined by amide linkages. The term "amino acid residue," includes but is not limited to amino acid residues contained in the group consisting of alanine (Ala or A), cysteine (Cys or C), aspartic acid (Asp or D), glutamic acid (Glu or E), phenylalanine (Phe or F), glycine (Gly or G), histidine (His or H), isoleucine (Ile or I), lysine (Lys or K), leucine (Leu or L), methionine (Met or M), asparagine (Asn or N), proline (Pro or P), glutamine (Gln or Q), arginine (Arg or R), serine (Ser or S), threonine (Thr or T), valine (Val or V), tryptophan (Trp or W), and tyrosine (Tyr or Y) residues. The term "amino acid residue" also may include nonstandard or unnatural amino acids. The term "amino acid residue" may include alpha-, beta-, gamma-, and delta-amino acids.

In some embodiments, the term "amino acid residue" may include nonstandard or unnatural amino acid residues contained in the group consisting of homocysteine, 2-Aminoadipic acid, N-Ethylasparagine, 3-Aminoadipic acid, Hydroxylysine, β-alanine, β-Amino-propionic acid, allo-Hydroxylysine acid, 2-Aminobutyric acid, 3-Hydroxyproline, 4-Aminobutyric acid, 4-Hydroxyproline, piperidinic acid, 6-Aminocaproic acid, Isodesmosine, 2-Aminoheptanoic acid, allo-Isoleucine, 2-Aminoisobutyric acid, N-Methylglycine, sarcosine, 3-Aminoisobutyric acid, N-Methylisoleucine, 2-Aminopimelic acid, 6-N-Methyllysine, 2,4-Diaminobutyric acid, N-Methylvaline, Desmosine, Norvaline, 2,2'-Diaminopimelic acid, Norleucine, 2,3-Diaminopropionic acid, Ornithine, and N-Ethylglycine. The term "amino acid residue" may include L isomers or D isomers of any of the aforementioned amino acids.

Other examples of nonstandard or unnatural amino acids include, but are not limited to, a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcpβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an unnatural analogue of a methionine amino acid; an unnatural analogue of a leucine amino acid; an unnatural analogue of a isoleucine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a γ-amino acid, a cyclic amino acid other than proline or histidine, and an aromatic amino acid other than phenylalanine, tyrosine or tryptophan.

As used herein, a "peptide" is defined as a short polymer of amino acids, of a length typically of 20 or less amino acids, and more typically of a length of 12 or less amino acids (Garrett & Grisham, Biochemistry, $2^{nd}$ edition, 1999, Brooks/Cole, 110). In some embodiments, a peptide as contemplated herein may include no more than about 2, 3, 4, 5, 6, 7, 8, 9, 10, 11, 12, 13, 14, 15, 16, 17, 18, 19, or 20 amino acids. A polypeptide, also referred to as a protein, is typically of length≥100 amino acids (Garrett & Grisham, Biochemistry, $2^{nd}$ edition, 1999, Brooks/Cole, 110). A polypeptide, as contemplated herein, may comprise, but is not limited to, 100, 101, 102, 103, 104, 105, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or more amino acid residues.

A peptide as contemplated herein may be further modified to include non-amino acid moieties. Modifications may include but are not limited to acylation (e.g., O-acylation (esters), N-acylation (amides), S-acylation (thioesters)), acetylation (e.g., the addition of an acetyl group, either at the N-terminus of the protein or at lysine residues), formylation lipoylation (e.g., attachment of a lipoate, a C8 functional group), myristoylation (e.g., attachment of myristate, a C14 saturated acid), palmitoylation (e.g., attachment of palmitate, a C16 saturated acid), alkylation (e.g., the addition of an alkyl group, such as an methyl at a lysine or arginine residue), isoprenylation or prenylation (e.g., the addition of an isoprenoid group such as farnesol or geranylgeraniol), amidation at C-terminus, glycosylation (e.g., the addition of a glycosyl group to either asparagine, hydroxylysine, serine, or threonine, resulting in a glycoprotein). Distinct from glycation, which is regarded as a nonenzymatic attachment of sugars, polysialylation (e.g., the addition of polysialic acid), glypiation (e.g., glycosylphosphatidylinositol (GPI) anchor formation, hydroxylation, iodination (e.g., of thyroid hormones), and phosphorylation (e.g., the addition of a phosphate group, usually to serine, tyrosine, threonine or histidine). Modifications may include the addition of a glycosylation tag (e.g., 4xDQNAT (SEQ ID NO: 12) optionally which may be added to the N-terminus, C-terminus, or both termini) and/or a histidine tag (e.g., 6xHis optionally which may be added to the N-terminus, C-terminus, or both termini).

Reference may be made herein to peptides, polypeptides, proteins and variants thereof. Reference amino acid sequences may include, but are not limited to, the amino acid sequence of any of SEQ ID NOs:1-10. Variants as contemplated herein may have an amino acid sequence that includes conservative amino acid substitutions relative to a reference amino acid sequence. For example, a variant peptide, polypeptide, or protein as contemplated herein may include conservative amino acid substitutions and/or non-conservative amino acid substitutions relative to a reference peptide, polypeptide, or protein. "Conservative amino acid substitutions" are those substitutions that are predicted to interfere least with the properties of the reference peptide, polypeptide, or protein, and "non-conservative amino acid substitution" are those substitution that are predicted to interfere most with the properties of the reference peptide, polypeptide, or protein. In other words, conservative amino acid substitutions substantially conserve the structure and the function of the reference peptide, polypeptide, or protein. The following table provides a list of exemplary conservative amino acid substitutions.

TABLE 1

| Original Residue | Conservative Substitution |
| --- | --- |
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |

TABLE 1-continued

| Original Residue | Conservative Substitution |
| --- | --- |
| Tyr | His, Phe, Trp |
| Val | Ile, Leu, Thr |

Conservative amino acid substitutions generally maintain: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain. Non-conservative amino acid substitutions generally disrupt: (a) the structure of the peptide, polypeptide, or protein backbone in the area of the substitution, for example, as a beta sheet or alpha helical conformation, (b) the charge or hydrophobicity of the molecule at the site of the substitution, and/or (c) the bulk of the side chain.

Variants comprising deletions relative to a reference amino acid sequence of peptide, polypeptide, or protein are contemplated herein. A "deletion" refers to a change in the amino acid or nucleotide sequence that results in the absence of one or more amino acid residues or nucleotides relative to a reference sequence. A deletion removes at least 1, 2, 3, 4, 5, 10, 20, 50, 100, or 200 amino acids residues or nucleotides. A deletion may include an internal deletion or a terminal deletion (e.g., an N-terminal truncation or a C-terminal truncation of a reference polypeptide or a 5'-terminal or 3'-terminal truncation of a reference polynucleotide).

Variants comprising fragment of a reference amino acid sequence of a peptide, polypeptide, or protein are contemplated herein. A "fragment" is a portion of an amino acid sequence which is identical in sequence to but shorter in length than a reference sequence. A fragment may comprise up to the entire length of the reference sequence, minus at least one amino acid residue. For example, a fragment may comprise from 5 to 1000 contiguous amino acid residues of a reference polypeptide, respectively. In some embodiments, a fragment may comprise at least 5, 10, 15, 20, 21, 22, 23, 24, 25, 26, 27, 28, 29, 30, 40, 50, 60, 70, 80, 90, 100, 150, 250, or 500 contiguous amino acid residues of a reference polypeptide. Fragments may be preferentially selected from certain regions of a molecule. The term "at least a fragment" encompasses the full length polypeptide.

Variants comprising insertions or additions relative to a reference amino acid sequence of a peptide, polypeptide, or protein are contemplated herein. The words "insertion" and "addition" refer to changes in an amino acid or sequence resulting in the addition of one or more amino acid residues. An insertion or addition may refer to 1, 2, 3, 4, 5, 10, 20, 30, 40, 50, 60, 70, 80, 90, 100, 150, or 200 amino acid residues.

Fusion proteins also are contemplated herein. A "fusion protein" refers to a protein formed by the fusion of at least one peptide, polypeptide, or protein or variant thereof as disclosed herein to at least one heterologous protein peptide, polypeptide, or protein (or fragment or variant thereof). The heterologous protein(s) may be fused at the N-terminus, the C-terminus, or both termini of the peptides or variants thereof.

"Homology" refers to sequence similarity or, interchangeably, sequence identity, between two or more polypeptide sequences. Homology, sequence similarity, and percentage sequence identity may be determined using methods in the art and described herein.

The phrases "percent identity" and "% identity," as applied to polypeptide sequences, refer to the percentage of residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. Percent identity for amino acid sequences may be determined as understood in the art. (See, e.g., U.S. Pat. No. 7,396,664, which is incorporated herein by reference in its entirety). A suite of commonly used and freely available sequence comparison algorithms is provided by the National Center for Biotechnology Information (NCBI) Basic Local Alignment Search Tool (BLAST) (Altschul, S. F. et al. (1990) J. Mol. Biol. 215:403 410), which is available from several sources, including the NCBI, Bethesda, Md., at its website. The BLAST software suite includes various sequence analysis programs including "blastp," that is used to align a known amino acid sequence with other amino acids sequences from a variety of databases.

Percent identity may be measured over the length of an entire defined polypeptide sequence, for example, as defined by a particular SEQ ID number (e.g., any of SEQ ID NOs:1-10), or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

A "variant" of a particular polypeptide sequence may be defined as a polypeptide sequence having at least 50% sequence identity to the particular polypeptide sequence over a certain length of one of the polypeptide sequences using blastp with the "BLAST 2 Sequences" tool available at the National Center for Biotechnology Information's website. (See Tatiana A. Tatusova, Thomas L. Madden (1999), "Blast 2 sequences—a new tool for comparing protein and nucleotide sequences", FEMS Microbiol Lett. 174:247-250). Such a pair of polypeptides may show, for example, at least 60%, at least 70%, at least 80%, at least 90%, at least 91%, at least 92%, at least 93%, at least 94%, at least 95%, at least 96%, at least 97%, at least 98%, or at least 99% or greater sequence identity over a certain defined length of one of the polypeptides. A "variant" may have substantially the same functional activity as a reference polypeptide (e.g., glycosylase activity or other activity). "Substantially isolated or purified" amino acid sequences are contemplated herein. The term "substantially isolated or purified" refers to amino acid sequences that are removed from their natural environment, and are at least 60% free, preferably at least 75% free, and more preferably at least 90% free, even more preferably at least 95% free from other components with which they are naturally associated. Variant polypeptides as contemplated herein may include variant polypeptides of any of SEQ ID NOs:1-10).

As used herein, "translation template" refers to an RNA product of transcription from an expression template that can be used by ribosomes to synthesize polypeptides or proteins.

The term "reaction mixture," as used herein, refers to a solution containing reagents necessary to carry out a given reaction. A reaction mixture is referred to as complete if it contains all reagents necessary to perform the reaction. Components for a reaction mixture may be stored separately in separate container, each containing one or more of the total components. Components may be packaged separately for commercialization and useful commercial kits may contain one or more of the reaction components for a reaction mixture.

The steps of the methods described herein can be performed in any suitable order unless otherwise indicated herein or otherwise clearly contradicted by context. The steps may be repeated or reiterated any number of times to achieve a desired goal unless otherwise indicated herein or otherwise clearly contradicted by context.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Cell-Free Protein Synthesis (CFPS)

The strains and systems disclosed herein may be applied to cell-free protein synthesis methods as known in the art. See, for example, U.S. Pat. Nos. 4,496,538; 4,727,136; 5,478,730; 5,556,769; 5,623,057; 5,665,563; 5,679,352; 6,168,931; 6,248,334; 6,531,131; 6,869,774; 6,994,986; 7,118,883; 7,189,528; 7,338,789; 7,387,884; 7,399,610; 8,703,471; and 8,999,668. See also U.S. Published Application Nos. 2015-0259757, 2014-0295492, 2014-0255987, 2014-0045267, 2012-0171720, 2008-0138857, 2007-0154983, 2005-0054044, and 2004-0209321. See also U.S. Published Application Nos. 2005-0170452; 2006-0211085; 2006-0234345; 2006-0252672; 2006-0257399; 2006-0286637; 2007-0026485; 2007-0178551. See also Published PCT International Application Nos. 2003/056914; 2004/013151; 2004/035605; 2006/102652; 2006/119987; and 2007/120932. See also Jewett, M. C., Hong, S. H., Kwon, Y. C., Martin, R. W., and Des Soye, B. J. 2014, "Methods for improved in vitro protein synthesis with proteins containing non standard amino acids," U.S. Patent Application Ser. No. 62/044,221; Jewett, M. C., Hodgman, C. E., and Gan, R. 2013, "Methods for yeast cell-free protein synthesis," U.S. Patent Application Ser. No. 61/792,290; Jewett, M. C., J. A. Schoborg, and C. E. Hodgman. 2014, "Substrate Replenishment and Byproduct Removal Improve Yeast Cell-Free Protein Synthesis," U.S. Patent Application Ser. No. 61/953,275; and Jewett, M. C., Anderson, M. J., Stark, J. C., Hodgman, C. E. 2015, "Methods for activating natural energy metabolism for improved yeast cell-free protein synthesis," U.S. Patent Application Ser. No. 62/098,578. See also Guarino, C., & DeLisa, M. P. (2012). A prokaryote-based cell-free translation system that efficiently synthesizes glycoproteins. Glycobiology, 22(5), 596-601. The contents of all of these references are incorporated in the present application by reference in their entireties.

In certain exemplary embodiments, one or more of the methods described herein are performed in a vessel, e.g., a single, vessel. The term "vessel," as used herein, refers to any container suitable for holding on or more of the reactants (e.g., for use in one or more transcription, translation, and/or glycosylation steps) described herein. Examples of vessels include, but are not limited to, a microtitre plate, a test tube, a microfuge tube, a beaker, a flask, a multi-well plate, a cuvette, a flow system, a microfiber, a microscope slide and the like.

In certain exemplary embodiments, physiologically compatible (but not necessarily natural) ions and buffers are utilized for transcription, translation, and/or glycosylation, e.g., potassium glutamate, ammonium chloride and the like. Physiological cytoplasmic salt conditions are well-known to those of skill in the art.

The strains and systems disclosed herein may be applied to cell-free protein methods in order to prepare glycosylated macromolecules (e.g., glycosylated peptides, glycosylated proteins, and glycosylated lipids). Glycosylated proteins that may be prepared using the disclosed strains and systems may include proteins having N-linked glycosylation (i.e., glycans attached to nitrogen of asparagine and/or arginine side-chains) and/or O-linked glycosylation (i.e., glycans attached to the hydroxyl oxygen of serine, threonine, tyrosine, hydroxylysine, and/or hydroxyproline). Glycosylated lipids may include O-linked glycans via an oxygen atom, such as ceramide.

The glycosylated macromolecules disclosed herein may include unbranched and/or branched sugar chains composed of monomers as known in the art such as, but not limited to, glucose (e.g., β-D-glucose), galactose (e.g., β-D-galactose), mannose (e.g., β-D-mannose), fucose (e.g., α-L-fucose), N-acetyl-glucosamine (GlcNAc), N-acetyl-galactosamine (GalNAc), neuraminic acid, N-acetylneuraminic acid (i.e., sialic acid), and xylose, which may be attached to the glycosylated macromolecule, growing glycan chain, or donor molecule (e.g., a donor lipid and/or a donor nucleotide) via respective glycosyltransferases (e.g., oligosaccharyltransferases, GlcNAc transferases, GalNAc transferases, galactosyltransferases, and sialyltransferases). The glycosylated macromolecules disclosed herein may include glycans as known in the art.

The disclosed cell-free protein synthesis systems may utilize components that are crude and/or that are at least partially isolated and/or purified. As used herein, the term "crude" may mean components obtained by disrupting and lysing cells and, at best, minimally purifying the crude components from the disrupted and lysed cells, for example by centrifuging the disrupted and lysed cells and collecting the crude components from the supernatant and/or pellet after centrifugation. The term "isolated or purified" refers to components that are removed from their natural environment, and are at least 60% free, preferably at least 75% free, and more preferably at least 90% free, even more preferably at least 95% free from other components with which they are naturally associated.

Genetically Modified Organisms

In some embodiments of the disclosed methods, a genetically modified organism is utilized. In some embodiments, the genetically modified prokaryote is a genetically modified strain of *Escherichia coli* or any other prokaryote suitable for preparing a lysate for CFGpS. Optionally, the modified strain of *Escherichia coli* is derived from rEc.C321. Preferably, the modified strain includes genomic modifications (e.g., deletions of genes rendering the genes inoperable) that preferably result in lysates capable of high-yielding cell-free protein synthesis. Also, preferably, the modified strain includes genomic modification (e.g., deletions of genes rendering the genes inoperable) that preferably result in lysates comprising sugar precursors for glycosylation at relatively high concentrations (e.g., in comparison to a strain not having the genomic modification). In some embodiments, a lysate prepared from the modified strain comprises sugar precursors at a concentration that is at least 20%, 30%, 40%, 50%, 60%, 70%, 80%, 90%, 100%, 150%, 200%, or higher than a lysate prepared from a strain that is not modified.

In some embodiments, the modified strain includes a modification that results in an increase in the concentration of a monosaccharide utilized in glycosylation (e.g., glucose, mannose, N-acetyl-glucosamine (GlcNAc), N-acetyl-galactosamine (GalNAc), galactose, sialic acid, neuraminic acid, fucose). As such, the modification may inactivate an enzyme that metabolizes a monosaccharide or polysaccharide utilized in glycosylation. In some embodiments, the modification inactivates a dehydratase or carbon-oxygen lyase enzyme (EC 4.2) (e.g., via a deletion of at least a portion of the gene encoding the enzyme). In particular, the modification may inactivate a GDP-mannose 4,6-dehydratase (EC 4.2.1.47). When the modified strain is *E. coli*, the modification may include an inactivating modification in the gmd gene (e.g., via a deletion of at least a portion of the gmd gene). The sequence of the *E. coli* gmd gene is provided herein as SEQ ID NO:1 and the amino acid sequence of *E. coli* GDP-mannose 4,6-dehydratase is provided as SEQ ID NO:2.

In some embodiments, the modified strain includes a modification that inactivates an enzyme that is utilized in the glycosyltransferase pathway. In some embodiments, the modification inactivates an oligosaccharide ligase enzyme (e.g., via a deletion of at least a portion of the gene encoding the enzyme). In particular, the modification may inactivate an O-antigen ligase that optionally conjugates an O-antigen to a lipid A core oligosaccharide. The modification may include an inactivating modification in the waaL gene (e.g., via a deletion of at least a portion of the waaL gene). The sequence of the *E. coli* waaL gene is provided herein as SEQ ID NO:3 and the amino acid sequence of *E. coli* O-antigen ligase is provided as SEQ ID NO:4.

In some embodiments, the modified strain includes a modification that inactivates a dehydratase or carbon-oxygen lyase enzyme (e.g., via a deletion of at least a portion of the gene encoding the enzyme) and also the modified strain includes a modification that inactivates an oligosaccharide ligase enzyme (e.g., via a deletion of at least a portion of the gene encoding the enzyme). The modified strain may include an inactivation or deletion of both gmd and waaL.

In some embodiments, the modified strain may be modified to express one or more orthogonal or heterologous genes. In particular, the modified strain may be genetically modified to express an orthogonal or heterologous gene that is associated with glycoprotein synthesis such as a glycosyltransferase (GT) which is involved in the lipid-linked oligosaccharide (LLO) pathway. In some embodiments, the modified strain may be modified to express an orthogonal or heterologous oligosaccharyltransferase (EC 2.4.1.119) (OST). Oligosaccharyltransferases or OSTs are enzymes that transfer oligosaccharides from lipids to proteins.

In particular, the modified strain may be genetically modified to express an orthogonal or heterologous gene in a glycosylation system (e.g., an N-linked glycosylation system and/or an O-linked glycosylation system). The N-linked glycosylation system of *Campylobacter jejuni* has been transferred to *E. coli*. (See Wacker et al., "N-linked glycosylation in *Campylobacter jejuni* and its functional transfer into *E. coli*," Science 2002, Nov. 29; 298(5599):1790-3, the content of which is incorporated herein by reference in its entirety). In particular, the modified strain may be modified to express one or more genes of the pgl locus of *C. jejuni* or one or more genes of a homologous pgl locus. The genes of the pgl locus include pglG, pglF, pglE, wlaJ, pglD, pglC, pglA, pglB, pglJ, pglI, pglH, pglK, and gne, and are used to synthesize lipid-linked oligosaccharides (LLOs) and transfer the oligosaccharide moieties of the LLOs to a protein via an oligosaccharyltransferase.

Suitable orthogonal or heterologous oligosaccharyltransferases (OST) which may be expressed in the genetically modified strains may include *Campylobacter jejuni* oligosaccharyltransferase PglB. The gene for the *C. jejuni* OST is referred to as pglB, which sequence is provided as SEQ ID NO:5 and the amino acid sequence of *C. jejuni* PglB is provided as SEQ ID NO:6. PglB catalyzes transfer of an oligosaccharide to a D/E-Y-N-X-S/T motif (Y, X≠P) present on a protein.

Crude cell lysates may be prepared from the modified strains disclosed herein. The crude cell lysates may be prepared from different modified strains as disclosed herein and the crude cell lysates may be combined to prepare a mixed crude cell lysate. In some embodiments, one or more crude cell lysates may be prepared from one or more modified strains including a genomic modification (e.g., deletions of genes rendering the genes inoperable) that preferably result in lysates comprising sugar precursors for glycosylation at relatively high concentrations (e.g., in comparison to a strain not having the genomic modification). In some embodiments, one or more crude cell lysates may be prepared from one or more modified strains that have been modified to express one or more orthogonal or heterologous genes or gene clusters that are associated with glycoprotein synthesis. Preferably, the crude cell lysates or mixed crude cell lysates are enriched in glycosylation components, such as lipid-linked oligosaccharides (LLOs), glycosyltransferases (GTs), oligosaccharyltransferases (OSTs), or any combination thereof. More preferably, the crude cell lysates or mixed crude cell lysates are enriched in $Man_3GlcNAc_2$ LLOs representing the core eukaryotic glycan and/or $Man_3GlcNAc_4Gal_2Neu_5Ac_2$ LLOs representing the fully sialylated human glycan.

The disclosed crude cell lysates may be used in cell-free glycoprotein synthesis (CFGpS) systems to synthesize a variety of glycoproteins. The glycoproteins synthesized in the CFGpS systems may include prokaryotic glycoproteins and eukaryotic proteins, including human proteins. The CFGpS systems may be utilized in methods for synthesizing glycoproteins in vitro by performing the following steps using the crude cell lysates or mixtures of crude cell lysates disclosed herein: (a) performing cell-free transcription of a gene for a target glycoprotein; (b) performing cell-free translation; and (c) performing cell-free glycosylation. The methods may be performed in a single vessel or multiple vessels. Preferably, the steps of the synthesis method may be performed using a single reaction vessel. The disclosed methods may be used to synthesis a variety of glycoproteins, including prokaryotic glycoproteins and eukaryotic glycoproteins.

In some embodiments, the engineered modified organism may be engineered to express a detoxified from of lipid A and/or reduced amounts of lipid A. As such, the engineered modified organisms can be utilized to prepare lysates that are less toxic than the unmodified organisms (i.e. wild-type organisms). In some embodiments, the engineered modified organism may be engineered to include a deletion in the lpxM gene and/or may be engineered to express the LpxE gene product (e.g., the *F. tularensis* LpxE gene product). As such, the engineered modified organisms can be utilized as source strains to prepare lysates that are detoxified via deletion of lpxM and/or expression of the *F. tularensis* LpxE gene product in the source strains.

Bioconjugate Vaccine Production

While protein-glycan coupling technology (PGCT) represents a simplified and cost-effective strategy for bioconjugate vaccine production, it has three main limitations. First, process development timelines, glycosylation pathway design-build-test (DBT) cycles, and bioconjugate production are all limited by cellular growth. Second, it has not yet been shown whether FDA-approved carrier proteins, such as the toxins from *Clostridium tetani* and *Corynebacterium diptheriae*, are compatible with N-linked glycosylation in living *E. coli*. Third, select non-native glycans are known to be transferred with low efficiency by the *C. jejuni* oligosaccharyltransferase (OST), PglB.

A modular, in vitro platform for production of bioconjugates has the potential to address all of these limitations. Here, we demonstrate that bioconjugates against pathogenic strains of *Franciscella tualrensis* and *Escherichia coli* can be produced through coordinated in vitro transcription, translation, and N-glycosylation in cell-free glycoprotein synthesis (CFGpS) reactions lasting just 20 hours. This system has the potential to reduce process development and distribution timelines for novel antibacterial vaccines from weeks to days. Further, because of the modular nature of the CFGpS platform and the fact that cell-free systems have demonstrated advantages for production of membrane proteins compared to living cells, this method could be readily applied to produce bioconjugates using FDA-approved carrier proteins, such as the *Clostridium tetani* and *Corynebacterium diptheriae* toxins, which are membrane localized. This could be accomplished simply by supplying plasmid encoding these carrier proteins to CFGpS reactions. Additionally, because of the modular nature of CFGpS, the in vitro approach could be used to prototype other natural or engineered homologs of the archetypal *C. jejuni* OST to identify candidate OSTs with improved efficiency for transfer of O-antigen LLOs of interest. This can be accomplished by enriching lysates with OSTs of interest and mixing them with LLO lysates in mixed lysate CFGpS reactions, as we have described previously. (See WO 2017/117539, the content of which is incorporated herein by reference in its entirety). Additionally, the methods can be performed using lysates prepared from microorganism that have been genetically modified to produce reduced amounts of endotoxin or de-toxified endotoxin, as required by FDA safety guidelines for vaccine production.

For example, we demonstrate that cell-free bioconjugate synthesis lysates can be detoxified by genetically engineering a host strain such that the structure of lipid A produced by the host strain exhibits to reduced toxicity. In some embodiments, the disclosed lysates prepared from genetically engineered host strains have a concentration of endotoxin units (EU) that is less than about 200,000 EU/mL, 180,000 EU/mL, 160,000 EU/mL, 140, 000 EU/mL, 120, 000 EU/mL, 100,000 EU/mL, 80,000 EU/mL, 60,000 EU/mL, 40,000 EU/mL, 20,000 EU/mL, 10,000 EU/mL, 8,000 EU/mL, 6,000 EU/mL, 4,000 EU/mL, 2,000 EU/mL, 1,000 EU/mL, 800 EU/mL, 600 EU/mL, 400 EU/mL, 200 EU/mL, 100 EU/mL, 80 EU/mL, 60 EU/mL, 40 EU/mL, 20 EU/mL, 10 EU/mL, 8 EU/mL, 6 EU/mL, 4 EU/mL 2 EU/mL 1 EU/mL, 0.9 EU/mL, 0.8 EU/mL 0.7 EU/mL, 0.6 EU/mL, 0.5 EU/mL, 0.4 EU/mL, 0.3 EU/mL, 0.2 EU/mL, 0.1 EU/mL, 0.05 EU/mL, or within a concentration range bounded by any of these values (e.g., within a range of about 0.3-180,000 EU/mL). The disclosed advances make it possible, for the first time, to produce and glycosylate authentic FDA-approved carrier proteins in detoxified lysates. As such, the detoxified lysates can be used in cell-free reaction mixtures to produce N-glycosylated carrier proteins as disclosed herein and the cell-free reaction mixtures can be directly administered (e.g., via injection) into a subject in need thereof (e.g., in order to induce an immune response which optionally protects the subject from infection by a microorganism that expresses the polysaccharide of the N-glycosylated carrier proteins) without requiring that the N-glycosylated carrier proteins first be purified from the cell-free reaction mixtures prior to being administered to the subject (i.e., the cell-free reaction mixture comprising the N-glycosylated carrier proteins may be administered directly to the subject).

Finally, we demonstrate that cell-free bioconjugate synthesis reactions can be lyophilized and retain bioconjugate synthesis capability, demonstrating the potential of the CFGpS system for on-demand, portable, and low cost production or development efforts for novel vaccines. This novel method for in vitro bioconjugate vaccine production has demonstrated advantages for rapid, modular, and portable vaccine prototyping and production compared to existing methods. Our technology enables rapid production of bioconjugate vaccines directed against a user-specified bacterial target for therapeutic development or fundamental research.

The present inventors are not aware of any prokaryotic cell-free system with the capability to produce glycoproteins or bioconjugate vaccines. There are commercial eukaryotic cell lysate systems for cell-free glycoprotein production, but these systems do not involve overexpression of orthogonal glycosylation machinery and do not enable modular, user-specified glycosylation in the way our system can. Additionally, these systems contain wild-type lipid A structures that would have to be removed from the vaccine-producing reaction to meet FDA regulations regarding endotoxin content in vaccine preparations. For these reasons, the disclosed technology is advantageous over technology in the prior art.

Finally, the cell-free platform disclosed here uniquely enables production of FDA-approved vaccine carriers at high soluble yields. Typically, production of the inventors' knowledge, this is the first report of recombinant production of tetanus toxin, which is commercially harvested from the pathogen *Clostridium tetani*. For these reasons, the disclosed technology has unique advantages for the production and conjugation of FDA-approved conjugate vaccines and thus has significant commercial promise.

The presently disclosed method for in vitro bioconjugate vaccine production has demonstrated advantages for rapid, modular, and portable vaccine prototyping and production compared to existing methods. The disclosed methods address limitations of existing production approaches, making the disclosed methods an attractive alternative or complementary strategy for antibacterial vaccine production. In light of the growing healthcare concerns caused by antibiotic-resistant bacterial infections, the disclosed methods have the potential to be extremely valuable for development, production, and distribution of novel vaccines against diverse pathogenic bacterial strains. Advantages of the disclosed methods include: on demand expression of bioconjugate vaccines; prototyping novel bioconjugate vaccine candidates; prototyping novel bioconjugate vaccine production pathways; distribution of bioconjugate vaccines to resource-poor settings.

In summary, we disclose the first prokaryotic cell-free system capable of coordinated, cell-free transcription, translation, and glycosylation of glycoprotein vaccines. The disclosed system enables production of bioconjugate vaccines in a short period of time (e.g., less than 24, 20, 16, 12, 8, 6, 4, or 2 hours). The modularity of the system enables rapid prototyping of novel glycosylation pathways and vaccine candidates with various carrier proteins. Suitable carriers may include but are not limited to *Haemophilus influenzae* protein D (PD) (SEQ ID NO: 7), *Neisseria meningitidis* porin protein (PorA) (SEQ ID NO: 8), *Corynebacterium diphtherias* toxin (CRM197) (SEQ ID NO: 9), *Clostridium tetani* toxin (TT) (SEQ ID NO: 10), and *Escherichia coli* maltose binding protein, or variants thereof. The components and products of the system maybe lyophilized, which enables the potential for broad and rapid distribution of vaccine production technology. The disclosed system reduces the time required to produce bioconjugates in a prokaryotic cell lysate from weeks to days, which could provide competitive advantage in commercialization of the technology.

Vaccine Formulations

The N-glycosylated carrier proteins disclosed herein may be formulated as antigenic compositions and/or vaccine composition for administration to a subject in need thereof. Such compositions can be formulated and/or administered in dosages and by techniques well known to those skilled in the medical arts taking into consideration such factors as the age, sex, weight, and condition of the particular patient, and the route of administration. The compositions may include pharmaceutical carriers, diluents, or excipients as known in the art. Further, the compositions may include preservatives (e.g., anti-microbial or anti-bacterial agents such as benzalkonium chloride) or adjuvants.

The compositions disclosed herein may be delivered via a variety of routes. Typical delivery routes include parenteral administration (e.g., intradermal, intramuscular or subcutaneous delivery). Other routes include oral administration, intranasal, intravaginal, intrarectal routes. The compositions may be formulated for intranasal or pulmonary delivery. Formulations of the pharmaceutical compositions may include liquid formulations (e.g., for oral, nasal, anal, vaginal, etc administration, including suspensions, syrups or elixirs) and preparations for parenteral, subcutaneous, intradermal, intramuscular or intravenous administration (e.g., injectable administration) such as sterile suspensions or emulsions.

The disclosed antigenic compositions and vaccine compositions optionally may include additional agents for inducing and/or potentiating an immune response such as adjuvants and/or may be administered with an adjuvant. The term "adjuvant" refers to a compound or mixture that enhances an immune response. An adjuvant can serve as a tissue depot that slowly releases the antigen and also as a lymphoid system activator that non-specifically enhances the immune response. Examples of adjuvants which may be utilized in the disclosed compositions include but are not limited to, co-polymer adjuvants (e.g., Pluronic L121® brand poloxamer 401, CRL1005, or a low molecular weight co-polymer adjuvant such as Polygen® adjuvant), poly (I:C), R-848 (a Th1-like adjuvant), resiquimod, imiquimod, PAM3CYS, aluminum phosphates (e.g., $AlPO_4$), loxoribine, potentially useful human adjuvants such as BCG (Bacille Calmette-Guerin) and *Corynebacterium parvum*, CpG oligodeoxynucleotides (ODN), cholera toxin derived antigens (e.g., CTA1-DD), lipopolysaccharide adjuvants, complete Freund's adjuvant, incomplete Freund's adjuvant, saponin (e.g., Quil-A), mineral gels such as aluminum hydroxide, surface active substances such as lysolecithin, pluronic polyols, polyanions, peptides, oil or hydrocarbon emulsions in water (e.g., MF59 available from Novartis Vaccines or Montanide ISA 720), keyhole limpet hemocyanins, and dinitrophenol.

The disclosed antigenic compositions and vaccine compositions may be administered under a prime-boost vaccination regimen. As used herein, a "prime-boost vaccination regimen" refers to a regimen in which a subject is administered a first composition one or more times (e.g., two or three times with about 2, 3, or 4 weeks between administrations) and then after a determined period of time (e.g., about 2 weeks, about 4 weeks, about 2 months, about 3 months, about 4 months, about 5 months, about 6 months, or longer), the subject is administered a second composition. The second composition may also be administered more than once, with at least 2, 3, or 4 weeks between administrations. The first and second compositions may be the same or different.

Illustrative Embodiments

The following embodiments are illustrative and are not intended to limit the scope of the claimed subject matter.

Embodiment 1. A method for synthesizing a N-glycosylated recombinant protein carrier which optionally may be utilized for preparing a bioconjugate vaccine, the method comprising performing coordinated transcription, translation, and N-glycosylation of the recombinant protein carrier in a cell-free reaction mixture thereby providing the N-glycosylated recombinant protein carrier which may be utilized as the bioconjugate vaccine, wherein the N-glycosylated recombinant protein carrier comprises: (i) a consensus sequence (which optionally is inserted in the protein carrier), N-X-S/T, wherein X may be any natural or unnatural amino acid except proline; and (ii) at least one antigenic polysaccharide from at least one bacterium N-linked to the recombinant protein carrier, wherein the at least one antigenic polysaccharide optionally is at least one bacterial O-antigen, optionally from one or more strains of $E.$ $coli$ or $Franciscella$ $tularensis$; and the bioconjugate vaccine optionally may include an adjuvant, optionally wherein the cell-free reaction mixture comprises a lysate prepared from an engineered bacterial strain that expresses a detoxified form of lipid A or lower amounts of lipid A relative to a wild-type strain.

Embodiment 2. The method of embodiment 1, wherein the carrier protein is an engineered variant of $E.$ $coli$ maltose binding protein (MBP).

Embodiment 3. The method of embodiment 1, wherein the carrier protein is selected from a detoxified variant of the toxin from $Clostridium$ $tetani$ and a detoxified variant of the toxin from $Corynebacterium$ $diptheriae$ Embodiment 4. The method of embodiment 1, wherein the carrier protein is selected from $Haemophilus$ $influenzae$ protein D (PD) and $Neisseria$ $meningitidis$ porin protein (PorA), and variants thereof.

Embodiment 5. The method of any of the foregoing embodiments, wherein the method utilizes an oligosaccharyltransferase (OST) which is a naturally occurring bacterial homolog of $C.$ $jejuni$ PglB.

Embodiment 6. The method of any of embodiments 1-4, wherein the method utilizes an OST that is an engineered variant of $C.$ $jejuni$ PglB.

Embodiment 7. The method of any of embodiments 1-4, wherein the method utilizes an OST that is a naturally occurring archaeal OST.

Embodiment 8. The method of any of embodiments 1-4, wherein the method utilizes an OST which is a naturally occurring single-subunit eukaryotic OST, such as those found in $Trypanosoma$ $bruceii.$ Embodiment 9. The method of any of the foregoing embodiments, which utilizes a lysate prepared from a detoxified strain of $E.$ $coli$, for example, a strain of $E.$ $coli$ which is deficient in lpxM (i.e., ΔlpxM) and/or a strain of $E.$ $coli$ that has been engineered to express the LpxE gene product (e.g., the $F.$ $tularensis$ LpxE gene product). (See, e.g., Needham et al., PNAS, 110(4), 1464-1469 (2013); and Brito and Singh, J. Pharma. Sci., 100(1), 34-37 (2011); the contents of which are incorporated herein by reference in their entireties).

Embodiment 9. A method for crude cell lysate preparation in which orthogonal genes or gene clusters are expressed in a source strain for the crude cell lysate, which results in lysates enriched with glycosylation components (lipid-linked oligosaccharides (LLOs), oligosaccharyltransferases (OSTs), and/or both LLOs and OSTs), and optionally which results in a separate lysate enriched with LLOs (e.g., LLOs associated with O-antigen) and a separate lysate enriched with OSTs (e.g., for which the LLOs are a substrate), and optionally combining the separate lysates to perform cell-free protein synthesis of a carrier protein which is glycosylated with the glycan component of the LLOs via the OST's enzyme activity, and further optionally purifying the glycosylated carrier protein and optionally administering the glycosylated carrier protein as an immunogen.

Embodiment 10. The method of embodiment 9, in which the source strain overexpresses a gene encoding an oligosaccharyltransferase (OST).

Embodiment 11. The method of embodiment 9 or 10, in which the source strain overexpresses a synthetic glycosyltransferase pathway, resulting in the production of O-antigens, optionally O-antigens from $F.$ $tularensis$ Schu S4 lipid-linked oligosaccharides (FtLLOs).

Embodiment 12. The method of embodiment 9 or 10, in which the source strain overexpresses a synthetic glycosyltransferase pathway, resulting in the production of O-antigens, optionally O-antigens from enterotoxigenic $E.$ $coli$ O78 lipid-linked oligosaccharides (EcO78LLOs)

Embodiment 13. The method of any of embodiments 9-12, in which the source strain overexpresses a glycosyltransferase pathway and an OST, resulting in the production of LLOs and OST.

Embodiment 14. The method of embodiment 9 or 10, in which the source strain overexpresses an O-antigen glycosyltransferase pathway from a pathogenic bacterial strain, resulting in the production of O-antigen lipid-linked oligosaccharides (LLOs).

Embodiment 15. A method for cell-free production of a bioconjugate vaccine that involves mixing crude cell lysates (e.g., any of the crude cell lysates of embodiments 9-14).

Embodiment 16. The method of embodiment 15, in which the bioconjugate vaccine comprises an immunogenic carrier that is a protein or a peptide.

Embodiment 17. The method of embodiment 15, in which the bioconjugate vaccine comprises an immunogenic carrier that is a protein or peptide comprising a protein or peptide thereof selected form $Haemophilus$ $influenzae$ protein D (PD), $Neisseria$ $meningitidis$ porin protein (PorA), $Corynebacterium$ $diphtherias$ toxin (CRM197), $Clostridium$ $tetani$ toxin (TT), and $Escherichia$ $coli$ maltose binding protein, and variants thereof.

Embodiment 18. The method of any of embodiments 1-17 in which the components of the method may be lyophilized and retain bioconjugate synthesis capability when rehydrated.

Embodiment 19. The method of any of embodiments 15-18 where the goal is on-demand vaccine production.

Embodiment 20. The method of any of embodiments 15-19 where the goal is vaccine production in resource-limited settings.

Embodiment 21. A kit for synthesizing a N-glycosylated carrier protein in vitro, the kit comprising one or more of the following components: (i) a first component comprising a cell lysate that comprises an orthogonal oligosaccharyltransferase (OST); (ii) a second component comprising a cell lysate that comprises an O-antigen (e.g., lipid-linked oligosaccharides (LLOs) comprising O-antigen; (iii) a third component comprising a transcription template and optionally a polymerase for synthesizing an mRNA from the transcription template encoding a carrier protein, the carrier protein comprising an inserted and/or a naturally occurring consensus sequence, N-X-S/T, wherein X may be any natural or unnatural amino acid except proline.

Embodiment 22. The kit of embodiment 21, wherein one or more of the first component, the second component, and the third component are lyophilized and retain biological activity when rehydrated.

Embodiment 23. The kit of embodiment 21 or 22, wherein the first component cell lysate is produced from a source strain (e.g., *E. coli*) that overexpresses a gene encoding the orthogonal OST (e.g. *C. jejuni* Pg1B).

Embodiment 24. The kit of any of embodiments 21-23, wherein the second component cell lysate is produced from a source strain that overexpresses a synthetic glycosyltransferase pathway (e.g., the biosynthetic machinery to produce the *Franciscella tularensis* Schu S4 O-antigen (FtLLOs lysate) or the biosynthetic machinery to produce the enterotoxigenic *E. coli* O78 lipid-linked oligosaccharides (EcO78LLOs lysate).

Embodiment 25. A method for cell-free production of a glycoprotein which optionally may be a bioconjugate suitable for use as a vaccine, the method comprising: (a) mixing a first cell lysate comprising an orthogonal oligosaccharyltransferase (OST) and a second cell lysate that comprises an O-antigen (e.g., as lipid-linked oligosaccharides (LLOs)) to prepare a cell-free protein synthesis reaction; (b) transcribing and translating a carrier protein in the cell-free protein synthesis reaction (e.g., optionally by adding a transcription template for the carrier protein and/or a polymerase to the cell-free protein synthesis reaction), the carrier protein comprising an inserted and/or naturally occurring consensus sequence, N-X-S/T, wherein X may be any natural or unnatural amino acid except proline; and (c) glycosylating the carrier protein in the cell-free protein synthesis reaction with the bacterial O-antigen.

Embodiment 25. The method of embodiment 24, wherein the second cell lysate comprises the O-antigen as part of lipid-linked oligosaccharides (LLOs).

Embodiment 26. The method of embodiment 24 or 25, further comprising formulating the glycoprotein as a vaccine composition optionally including an adjuvant.

Embodiment 27. A vaccine prepared by any of the foregoing methods and/or kits and/or a vaccine comprising a component present in or prepared by any of the foregoing methods and/or kits.

Embodiment 28. A vaccination method comprising administering the vaccine of embodiment 27 to a subject in need thereof.

EXAMPLES

The following Examples are illustrative and are not intended to limit the scope of the claimed subject matter.

Example 1

On-Demand, Cell-Free Biomanufacturing of Conjugate Vaccine at the Point-of Care Abstract Conjugate vaccines are highly effective against bacterial pathogens with extremely rare instances of resistance, representing a powerful tool to respond to the emerging threat of drug resistant bacteria. However, current technology for making conjugate vaccines is technically complex and relies on living cells, which necessitates highly centralized manufacturing, specialized equipment, lengthy development timelines, and cold-chain distribution. Here, we describe a modular technology for portable, on-demand in vitro bioconjugate vaccine expression (iVAX), which combines cell-free protein synthesis of licensed vaccine carrier proteins with N-linked glycosylation of bacterial polysaccharide antigens in freeze-dried lysates from detoxified, nonpathogenic *Escherichia coli*. Upon rehydration, iVAX technology can synthesize single doses of bioconjugate vaccines against diverse bacterial pathogens in one hour, including *Francisella tularensis* subsp. *tularensis* (type A) strain Schu S4 and pathogenic *E. coli* strains O78 and O7 Immunization of BALB/c mice with cell-free synthesized vaccines elicited pathogen-specific antibodies at significantly higher levels compared to the same vaccine molecules produced using glycoengineered bacteria. The iVAX platform promises to enable rapid development of new bioconjugate vaccines with increased access through refrigeration-independent distribution and on-demand, decentralized production.

Introduction

For decades, vaccines have been an important pillar in preventative medicine, providing protection against a wide array of disease-causing pathogens by induction of humoral and/or cellular immunity. Conjugate vaccines are among the safest and most effective methods for preventing life-threatening bacterial infections [1] and have been shown to reduce the rate of emergence of drug resistant strains [2]. Conjugate vaccines are composed of an immunogenic (CD4+ T-cell dependent antigen) protein carrier chemically conjugated to a polysaccharide antigen from the surface of the target bacterium, typically capsular polysaccharide (CPS)- or lipopolysaccharide (LPS)-derived antigens. These protein-polysaccharide conjugates induce immune responses directed against the bacterial polysaccharide antigen characterized by polysaccharide-specific IgM-to-IgG class switching, memory B cell development, and long-lived T-cell memory [3-7]. As a result, conjugate vaccines have proven to be a highly efficacious and safe strategy for protecting against virulent bacterial pathogens, including *Haemophilus influenzae, Neisseria meningitidis*, and *Streptococcus pneumoniae* [7-9], resulting in several marketed products and many others in clinical development [3, 8].

Despite their effectiveness, conjugate vaccines are particularly challenging to develop and distribute for several reasons. First, the conventional process to produce conjugate vaccines involves biosynthesis, purification, and chemical conjugation of the polysaccharide and protein components, which is complex, costly, and low yielding [10]. Moreover, in some cases, chemical conjugation can significantly alter the structure of polysaccharide, resulting in the loss of the protective epitope [11]. Second, biosynthesis of the polysaccharide component typically requires large-scale cultivation of pathogenic bacteria, which is accompanied by biosafety regulations and limits the development of new conjugate vaccines to bacterial targets that are amenable to large-scale fermentation under normal laboratory conditions. Third, as a result of process complexity and associated biosafety concerns, conjugate vaccine manufacturing takes place in centralized production facilities from which vaccines are distributed via a refrigerated supply chain, which is critical to avoid precipitation and significant loss of the pathogen-specific carbohydrate component upon both heating and freezing [10, 12, 13]. Accidental heating and freezing in the cold chain result in significant vaccine spoilage [14] and, more broadly, the need to establish and maintain cold chain refrigeration creates economic and logistical challenges that limit the reach of vaccination campaigns, especially in the developing world [12, 15].

As an alternative to chemical conjugation, it was recently demonstrated that polysaccharide-protein conjugates can be made in *Escherichia coli* via protein-glycan coupling technology (PGCT) [16]. In this approach, engineered *E. coli* cells covalently attach heterologously expressed CPS or O-PS antigens to specific residues on carrier proteins in the *E. coli* periplasm via an asparagine-linked (N-linked) glycosylation reaction catalyzed by the *Campylobacter jejuni* oligosaccharyltransferase PglB (CjPglB). To date, this technology has yielded a handful of vaccine candidates, termed "bioconjugates" to highlight the in vivo production process, including those directed against important human pathogens including *Burkholderia pseudomallei* [17], *E. coli* O121 [18], *E. coli* O157:H7 [19], *Francisella tularensis* [20, 21], and *Staphylococcus aureus* [22]. In all cases tested, the vaccines either stimulated serum bactericidal antibodies [19] or provided protection against pathogen challenge [17, 20-22]. While PGCT can avoid some challenges associated with conventional conjugation vaccine manufacturing (e.g., biosafety concerns associated with growing pathogenic bacteria), bioconjugate vaccine production still relies on living bacterial cells. Thus, as with conventional conjugation approaches, bioconjugate vaccine production remains subject to lengthy in vivo process development timelines and is dependent upon skilled operators and specialized equipment, which altogether necessitate centralized production facilities.

Cell-free protein synthesis (CFPS) is an emerging technology that uses cell lysates, rather than living cells, to synthesize proteins in vitro [23]. CFPS has recently been used to enable rapid, low-cost, and decentralized production of protein subunit vaccines [24, 25], protein therapeutics [25], and diagnostics [26, 27]. Importantly, CFPS technology (i) allows for shortened protein synthesis timelines, as relevant yields of protein can be synthesized in vitro in just a few hours, (ii) can be freeze-dried for transportation and storage at ambient temperature and reconstituted by just adding water [24, 25], and (iii) circumvents biosafety concerns associated with the use of living cells outside of a controlled laboratory setting. However, until recently, cell-free systems have been limited in their ability to synthesize glycosylated proteins at relevant titers and in terms of the relatively small number of glycan structures that can be installed on proteins [28], preventing the synthesis of bioconjugate vaccines in cell-free systems. We recently described a cell-free glycoprotein synthesis (CFGpS) technology that enables one-pot, cell-free production of glycosylated proteins [29]. CFGpS is a modular platform in which acceptor protein, polysaccharide, and oligosaccharyltransferase components can be rapidly interchanged to yield cell-free production of structurally diverse glycoproteins, including human glycoproteins and eukaryotic glycans [29]. However, it remains to be shown whether a similar cell-free approach can be used for in vitro synthesis of bioconjugate vaccines.

To address this gap, here we describe a cell-free platform for portable, on-demand in vitro bioconjugate vaccine expression (iVAX). iVAX enables rapid, inexpensive, and portable production of safe and effective antibacterial vaccine candidates via complete cell-free biosynthesis and glycosylation of licensed carrier proteins with bacterial polysaccharide antigens (FIG. 1). iVAX was designed to have the following features. First, iVAX is fast. It can produce FDA-approved carrier proteins at levels sufficient for individual doses in 1-2 h. Second, iVAX is robust, operating under a range of temperature conditions. Third, iVAX is modular, being capable of efficient antigen conjugation of diverse O-antigen polysaccharides (O-PS), including the highly virulent *Franciscella tularensis* subsp. *tularensis* (type A) strain Schu S4, enterotoxigenic (ETEC) *E. coli* O78, and uropathogenic (UPEC) *E. coli* O7. Fourth, iVAX is shelf-stable, derived from freeze-dried cell-free reactions that operate in a just-add-water strategy. Fifth, iVAX is safe, leveraging lipid A remodeling that effectively avoids the high levels of endotoxin that are present in non-engineered *E. coli* manufacturing platforms. We demonstrate that that anti-*F. tularensis* bioconjugates derived from freeze-dried, low-endotoxin iVAX reactions elicit pathogen-specific antibody responses in mice and outperform a bioconjugate produced using the established PGCT approach in living cells. Overall, this work represents an alternative approach to centralized conjugate vaccine biomanufacturing which could be readily adapted for developing vaccine candidates against many other bacterial pathogens and offers a fundamentally new way to deliver the protective benefits of existing vaccine technologies to both the developed and developing world.

Results

In vitro synthesis of licensed vaccine carrier proteins. To demonstrate proof-of-principle for point-of-care conjugate vaccine production, we first set out to express a set of carrier proteins that are currently used in FDA-approved conjugate vaccines. Producing these carrier proteins in soluble conformations in vitro represented an important benchmark because their expression in living *E. coli* has proven challenging, often requiring purification and refolding of insoluble product from inclusion bodies [30, 31], fusion of expression partners such as maltose binding protein (MBP) to increase soluble expression [31, 32], or expression of protein fragments in favor of the full-length protein [32]. In contrast, cell-free protein synthesis approaches have recently shown promise for difficult-to-express proteins [33, 34]. The carrier proteins that we focused on here included nonacylated *H. influenzae* protein D (PD), the *N. meningitidis* porin protein (PorA), and genetically detoxified variants of the *Corynebacterium diphtheriae* toxin (CRM197) and the *Clostridium tetani* toxin (TT). We also tested expression of *E. coli* MBP, and the fragment C (TTc) and light chain (TTlight) domains of TT. MBP is not a licensed carrier, but MBP glycoconjugates has been shown to elicit polysaccharide-specific humoral and Th1-biased cellular responses in mice [19]. Similarly, the TT domains, TTlight and TTc, have not been used in licensed vaccines, but are sufficient for protection against *C. tetani* challenge in mice [32]. To enable glycosylation, all carriers were modified at their C-termini with an optimal bacterial glycosylation motif, DQNAT (SEQ ID NO: 11) [35], that was tandemly repeated four times (denoted as 4×DQNAT (SEQ ID NO: 12)). A C-terminal 6×His tag was also included to enable purification and detection via Western blot analysis. A variant of superfolder green fluorescent protein that contained an internal DQNAT (SEQ ID NO: 11) glycosylation site (sfGFP$^{217\text{-}DQNAT}$) was used as a model protein to facilitate system development.

Figure 2:
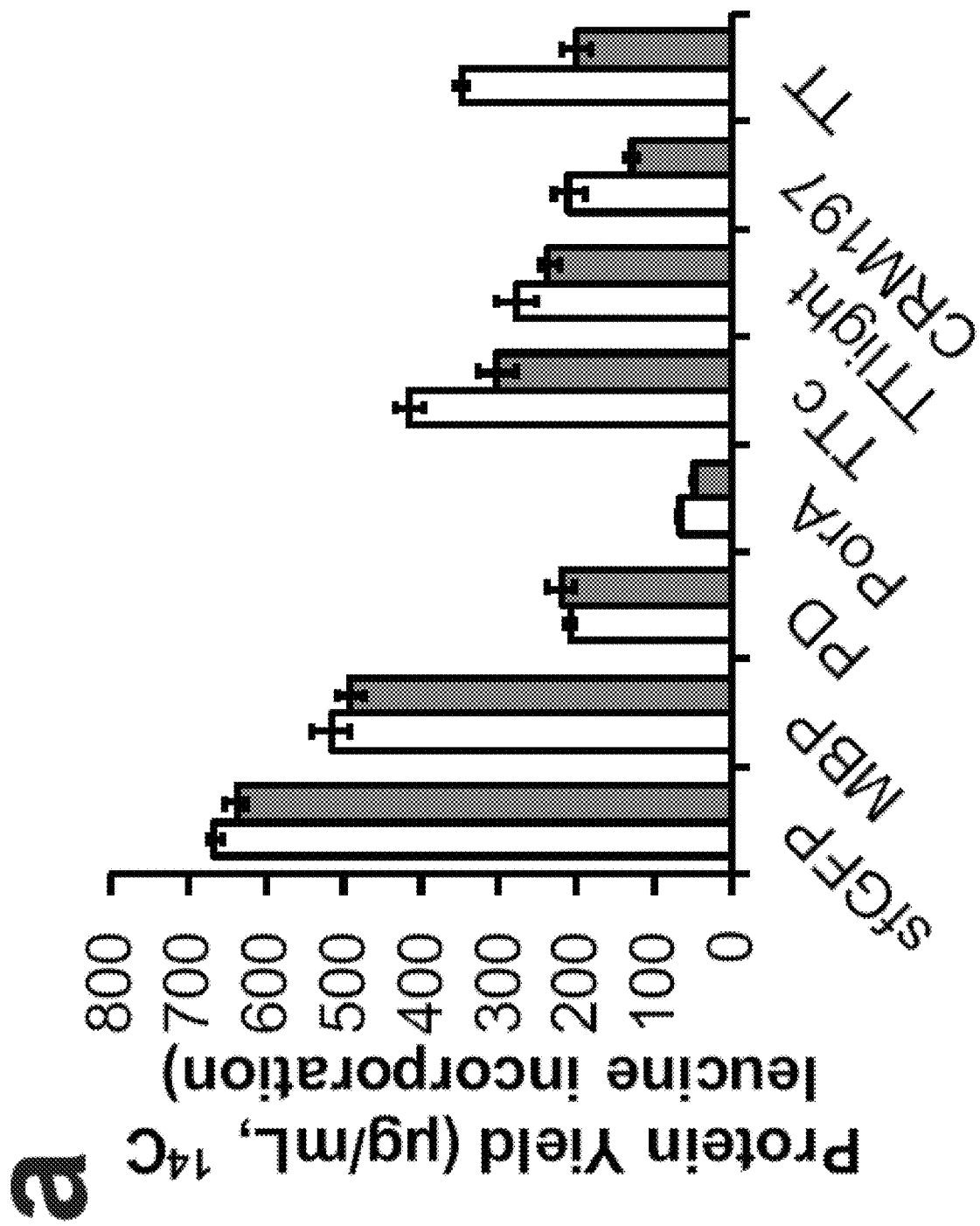
FIG. 2. In vitro synthesis of FDA-approved carrier proteins. (a) All four FDA-approved conjugate vaccine carrier proteins were synthesized solubly in vitro, as measured via $^{14}$C-leucine incorporation. These include *H. influenzae* protein D (PD), the *N. meningitidis* porin protein (PorA), and genetically detoxified variants of the *C. diphtherias* toxin (CRM197) and the *C. tetani* toxin (TT). Promising carriers that are not yet FDA-approved were also synthesized solubly, including *E. coli* maltose binding protein (MBP) and the fragment C (TTc) and light chain (TTlight) domains of TT. Values represent means and error bars represent standard deviations of biological replicates (n=3). (b) Full length product was observed for all proteins tested via Western blot. Different exposures are indicated with solid lines.
Figure 2:
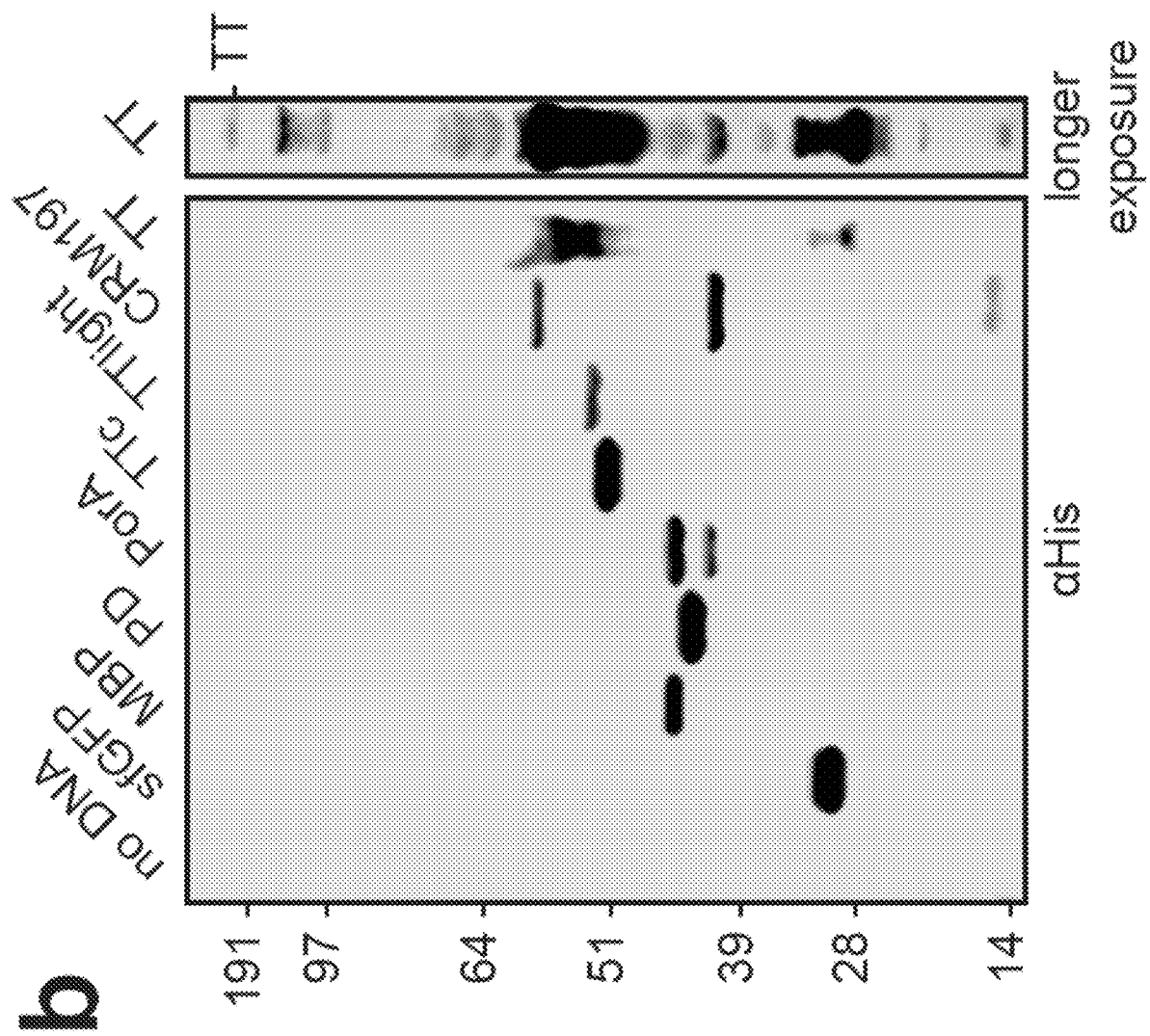

All eight carriers were synthesized in vitro with soluble yields of ~50-650 μg mL$^{-1}$ as determined by $^{14}$C-leucine incorporation (FIG. 2a). In particular, the MBP$^{4\times DQNAT}$ and PD$^{4\times DQNAT}$ variants were nearly ~100% soluble, with yields of 500 μg mL$^{-1}$ and 200 μg mL$^{-1}$, respectively, and accumulated as exclusively full-length products according to Western blot analysis (FIG. 2b), making these attractive iVAX candidates moving forward. Notably, similar soluble yields were reached for all carriers at 25° C., 30° C., and 37° C., with the exception of CRM197$^{4\times DQNAT}$ (FIG. 6a), which is known to be heat sensitive [13]. This suggests that our cell-free method for making these carriers is robust over a 13° C.-range in biosynthesis temperature and could find use in settings where precise temperature control is not feasible.

Figure 7:
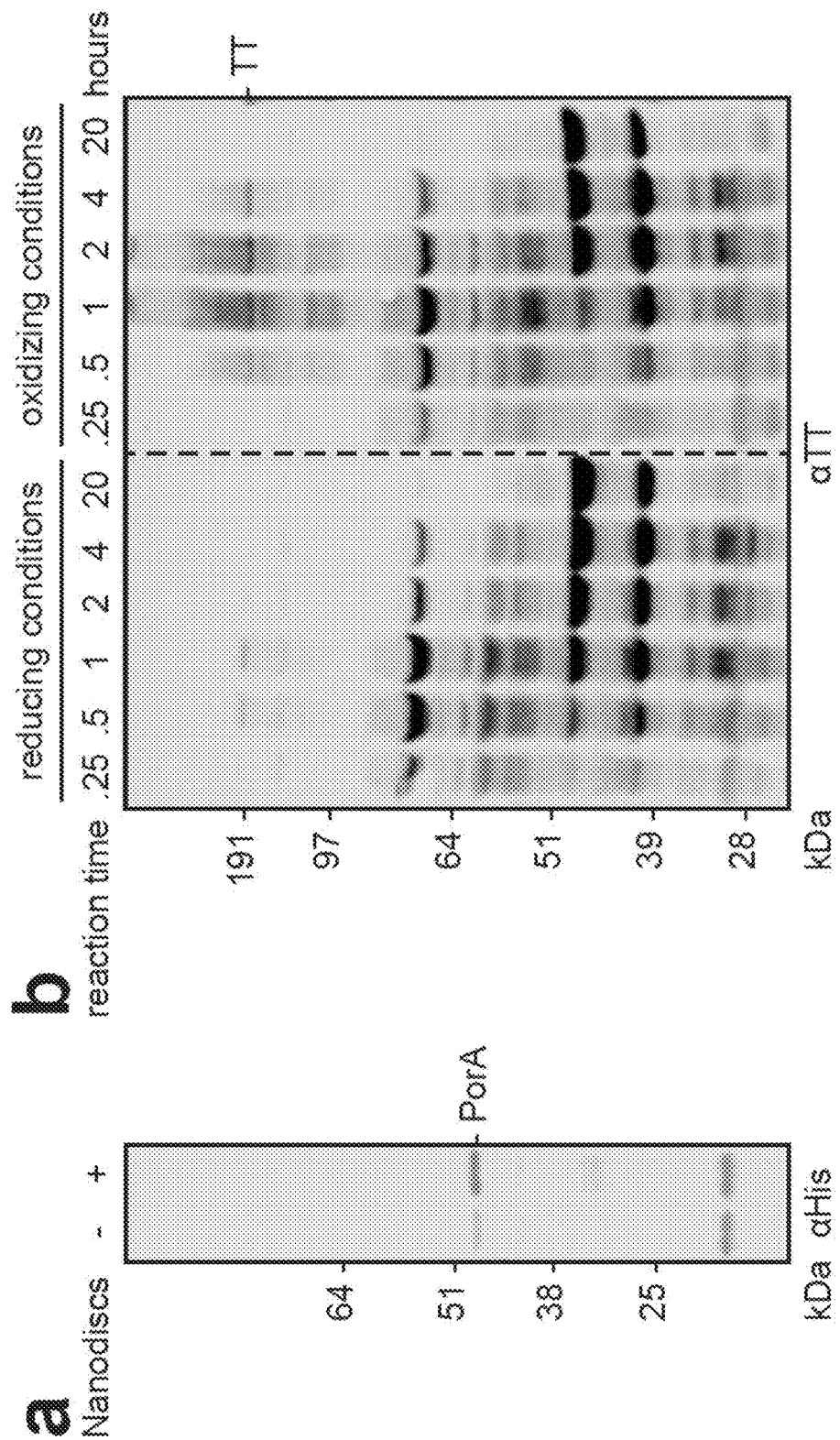
FIG. 7. Optimization of PorA and tetanus toxin expression in vitro. Blots show soluble fractions of reactions producing PorA$^{4\times DQNAT}$ or TT$^{4\times DQNAT}$. (a) Soluble expression of PorA was improved through the addition of lipid nanodiscs to the reaction. (b) Expression of full-length TT was enhanced by (i) performing in vitro protein synthesis in oxidizing conditions to improve assembly of the disulfide-bonded heavy and light chains into full-length TT and (ii) allowing reactions to run for only 2 h to minimize protease degradation. Images are representative of at least three biological replicates. Dashed line indicates samples are from the same blot with the same exposure.
Figure 8:
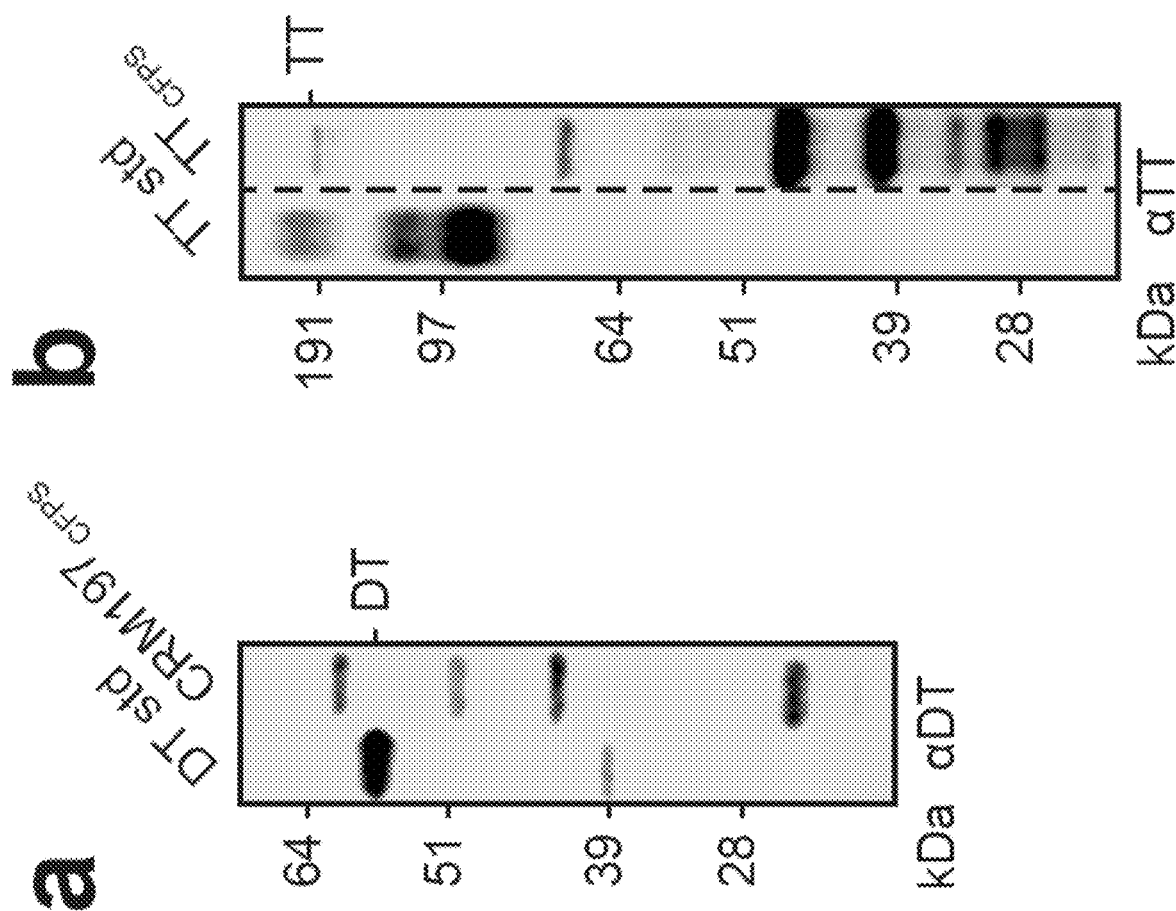
FIG. 8. In vitro synthesis of CRM197 and TT compared to commercial standards. In vitro synthesized (a) CRM197 and (b) TT are detected with α-DT and α-TT antibodies, respectively, and are comparable in size to commercially available purified DT and TT protein standards (50 ng standard loaded). Images are representative of at least three biological replicates. Dashed lines indicate samples are from the same blot with the same exposure. Solid lines indicate different exposures.

The open reaction environment of our cell-free reactions enabled facile manipulation of the chemical and reaction environment to improve production of more complex carriers. In the case of the membrane protein PorA$^{4\times DQNAT}$, lipid nanodiscs were added to increase soluble expression (FIG. 7a). Nanodiscs provide a cellular membrane mimic to co-translationally stabilize hydrophobic regions of membrane proteins [36]. For expression of TT, which contains an intermolecular disulfide bond, expression was carried out for 2 hours in oxidizing conditions [37], which improved assembly of the heavy and light chains into full-length product and minimized protease degradation of full-length TT (FIG. 7b). In vitro synthesized CRM197$^{4\times DQNAT}$ and TT$^{4\times DQNAT}$ were comparable in size to commercially available purified diphtheria toxin (DT) and TT protein standards and were reactive with α-DT and α-TT antibodies, respectively (FIG. 8), indicating that both were synthesized with immunologically relevant conformations. This is notable as CRM197 and TT are FDA-approved vaccine antigens for diphtheria and tetanus, respectively, when they are administered without conjugated polysaccharides. Together, our results highlight the ability of CFPS to express licensed conjugate vaccine carrier proteins, including the diphtheria and tetanus vaccine antigens, in soluble conformations over a range of permissible temperatures.

On-demand synthesis of bioconjugate vaccines. We next sought to synthesize conjugated versions of these carrier proteins by merging their in vitro expression with one-pot, cell-free glycosylation. For the vaccine target, we focused on the highly virulent *Francisella tularensis* subsp. *tularensis* (type A) strain Schu S4, a gram-negative, facultative coccobacillus and the causative agent of tularemia. This bacterium is categorized as a class A bioterrorism agent due to its high fatality rate, low dose of infection, and ability to be aerosolized [38]. Although there is currently no licensed anti-*F. tularensis* vaccine available, several studies have independently confirmed the important role of antibodies directed against *F. tularensis* LPS, specifically the O-PS repeat unit, in providing protection against the highly virulent Schu S4 strain [39-41]. More recently, a purified recombinant vaccine comprising the *F. tularensis* Schu S4 O-PS conjugated to the *Pseudomonas aeruginosa* exotoxin A (EPA) carrier protein was produced using PGCT in living *E. coli* [20, 21]. A first-generation version of this bioconjugate boosted levels of IgG specific to *F. tularensis* LPS and significantly increased the time to death upon subsequent pathogen challenge [20]. Further optimization of this vaccine to enhance decoration of EPA with FtO-PS yielded a next-generation bioconjugate that was protective against challenge with the high-virulence SchuS4 strain in a rat inhalation model of tularemia [21]. In light of these earlier findings, we investigated the ability of the iVAX platform to produce anti-tularemia bioconjugate vaccine candidates on-demand via conjugation of the *F. tularensis* Schu S4 O-PS (FtO-PS) structure to diverse carrier proteins in vitro.

Figure 3:
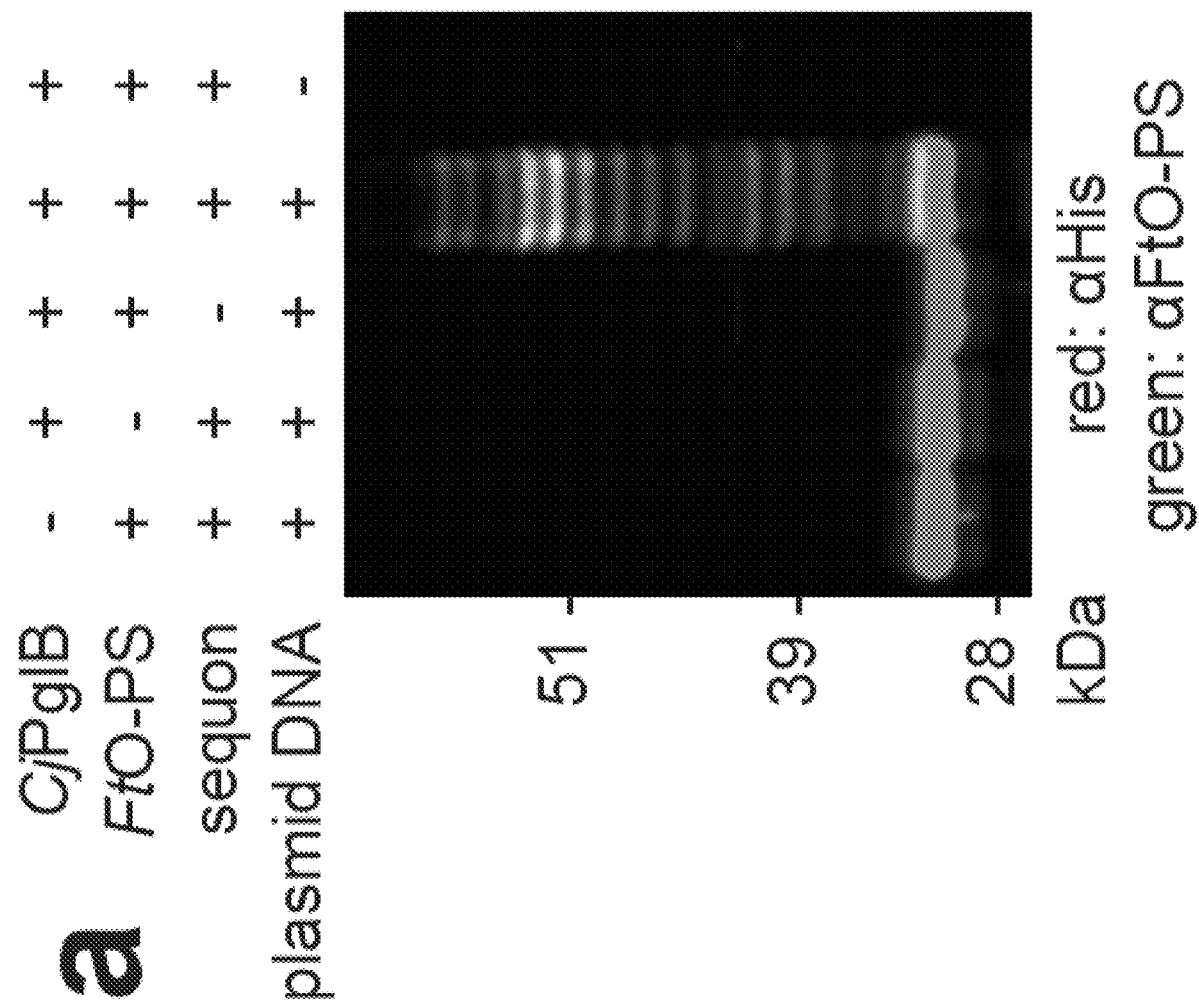
FIG. 3. On-demand and reproducible production of bioconjugates against *F. tularensis* using iVAX. iVAX lysates were prepared from cells expressing CjPglB and a biosynthetic pathway encoding FtO-PS. (a) Glycosylation of sfGFP$^{217\text{-}DQNAT}$ with FtO-PS was only observed when CjPglB, FtO-PS, and the preferred sequon were present in the reaction (lane 3). When plasmid DNA is omitted, sfGFP$^{217\text{-}DQNAT}$ synthesis was not observed. (b) Biological replicates of iVAX reactions producing sfGFP$^{217\text{-}DQNAT}$ using the same lot (left) or different lots (right) of iVAX lysates demonstrated reproducibility of reactions and lysate preparation. (c) On-demand synthesis of bioconjugate vaccines with immunogenic carriers including authentic FDA-approved carriers. Bioconjugates were purified using Ni-NTA agarose from 1 mL iVAX reactions lasting ~1 h at 30° C. Unless replicates are explicitly shown, images are representative of at least three biological replicates. Dashed lines indicate samples are from the same blot with the same exposure.
Figure 3:
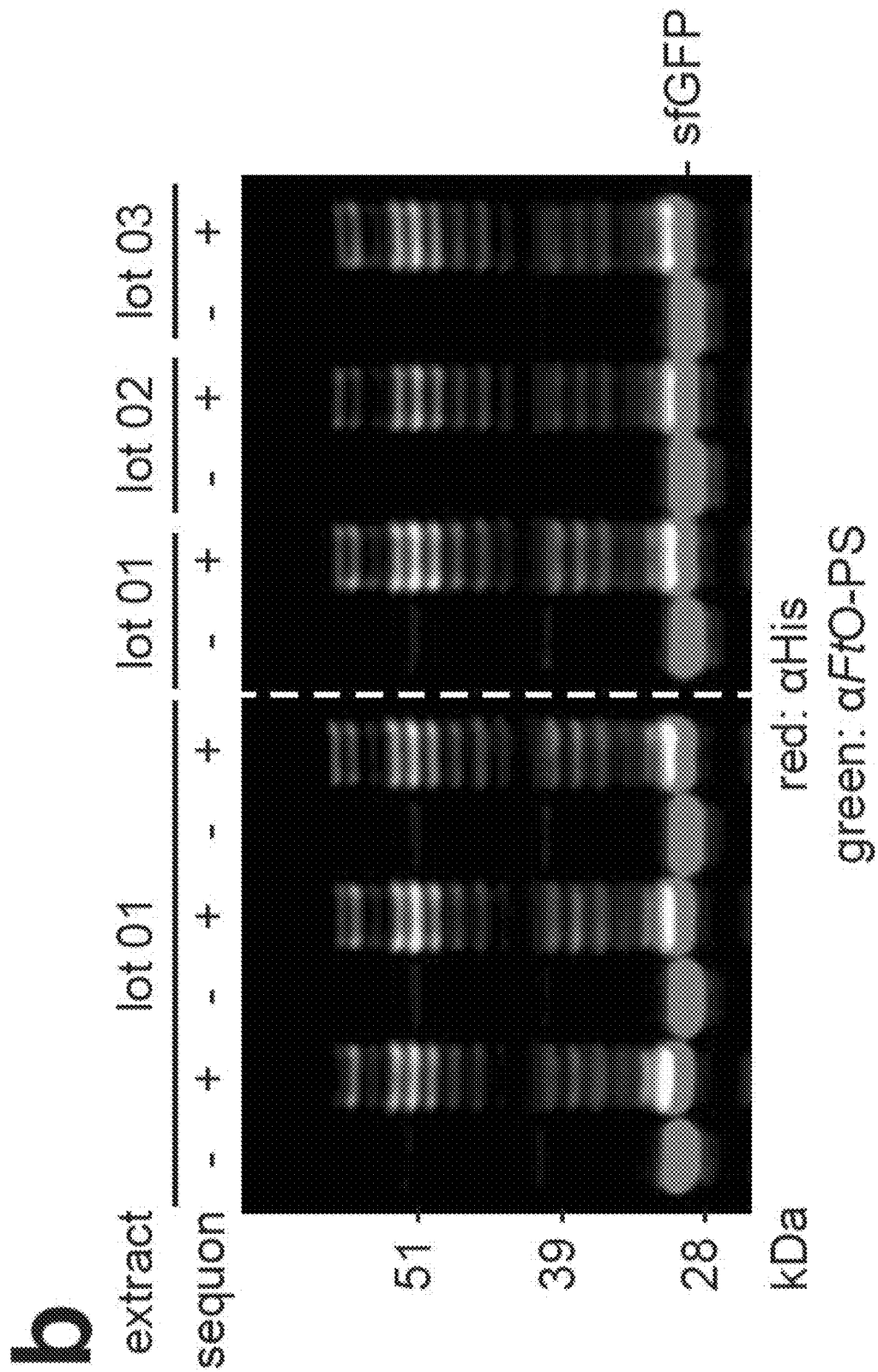
Figure 3:
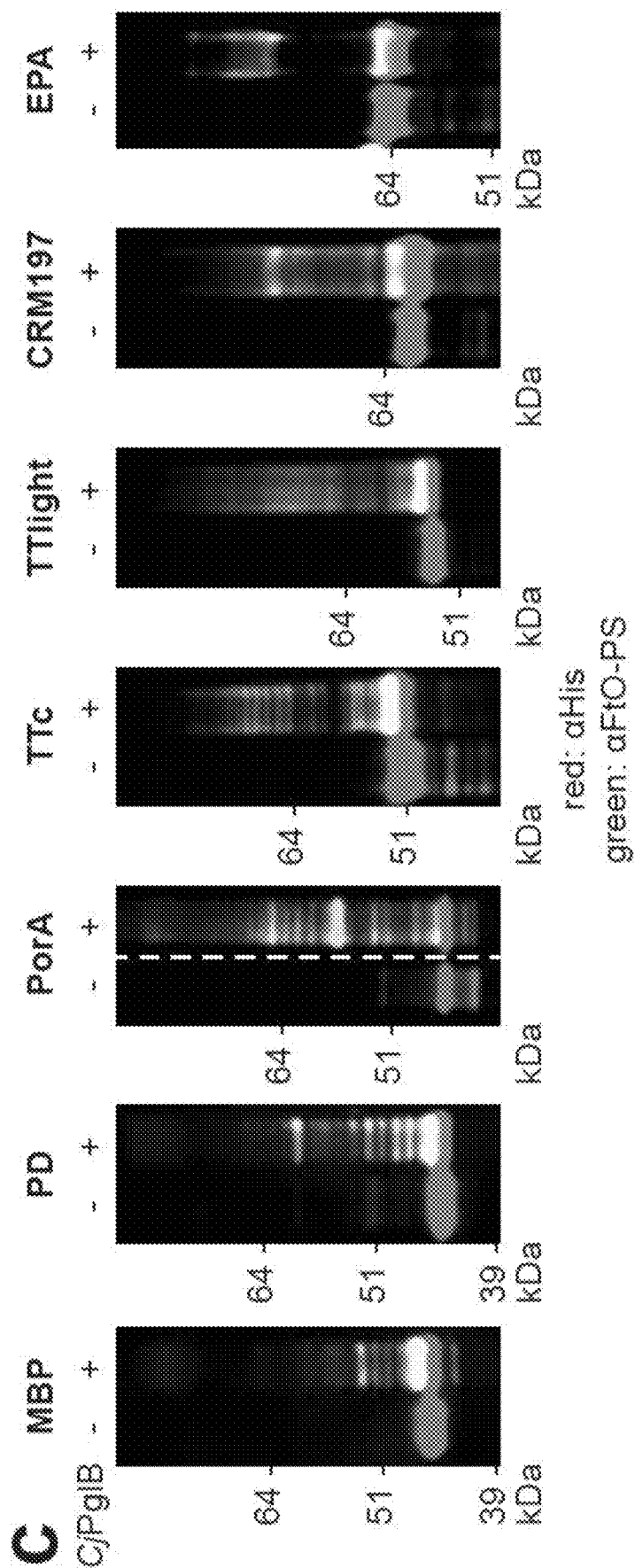
Figure 6:
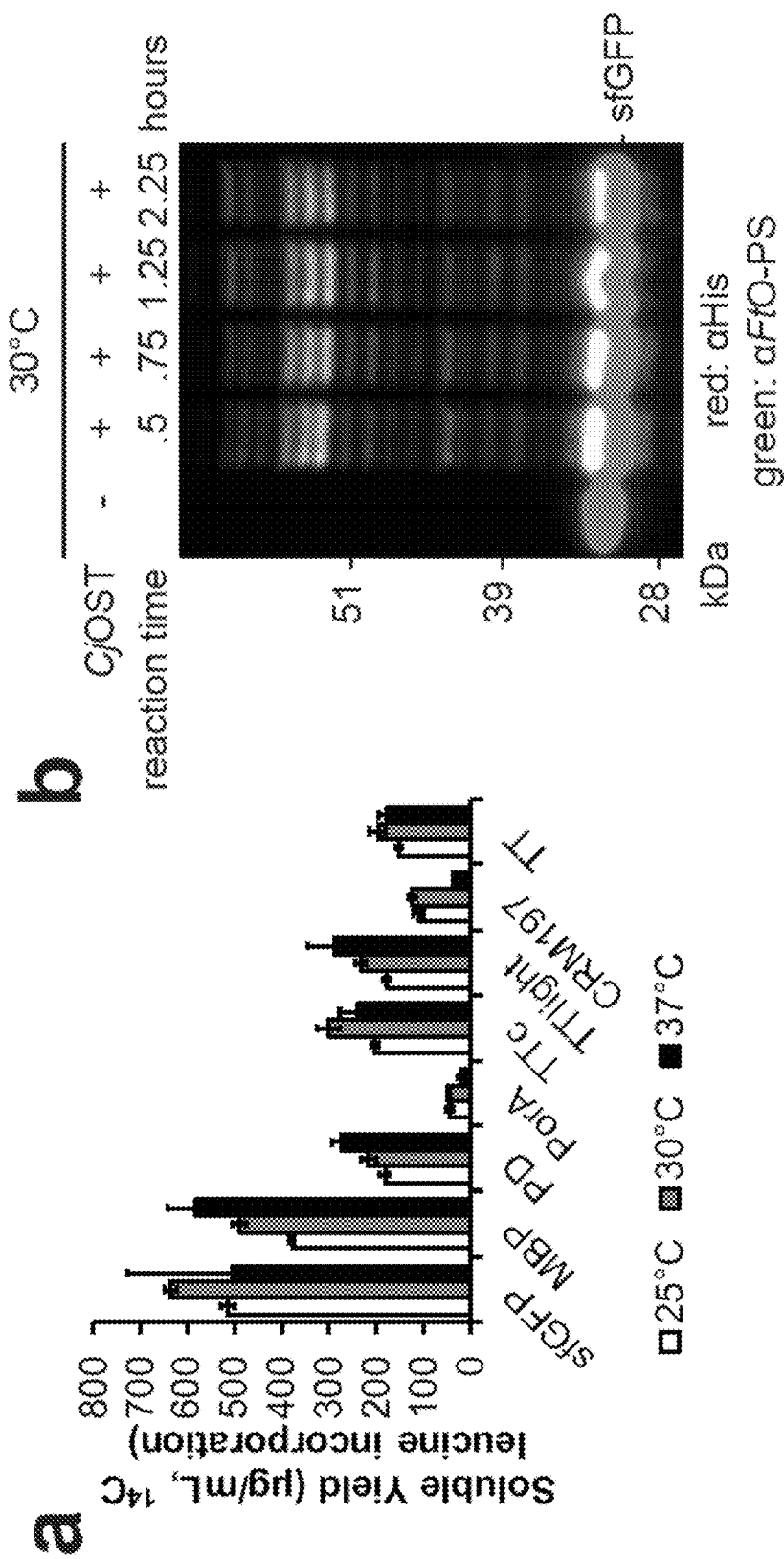
FIG. 6. Protein synthesis and glycosylation in iVAX reactions occurs in 1 h and is robust at a range of temperatures. (a) With the exception of CRM197, all carriers were expressed with similar soluble yields at 25° C., 30° C., and 37° C., as measured via $^{14}$C-leucine incorporation. Kinetics of O-PS glycosylation in iVAX reactions at (b) 30° C. and (c) 37° C., 25° C., and room temperature (~21° C.) are comparable and showed that protein synthesis and glycosylation occurred in the first hour of the iVAX reaction. Together, these results demonstrate that strict temperature control is not required for bioconjugate vaccine synthesis in the iVAX platform, which is critical for a decentralized production platform in settings where precise temperature control is not always feasible.
Figure 6:
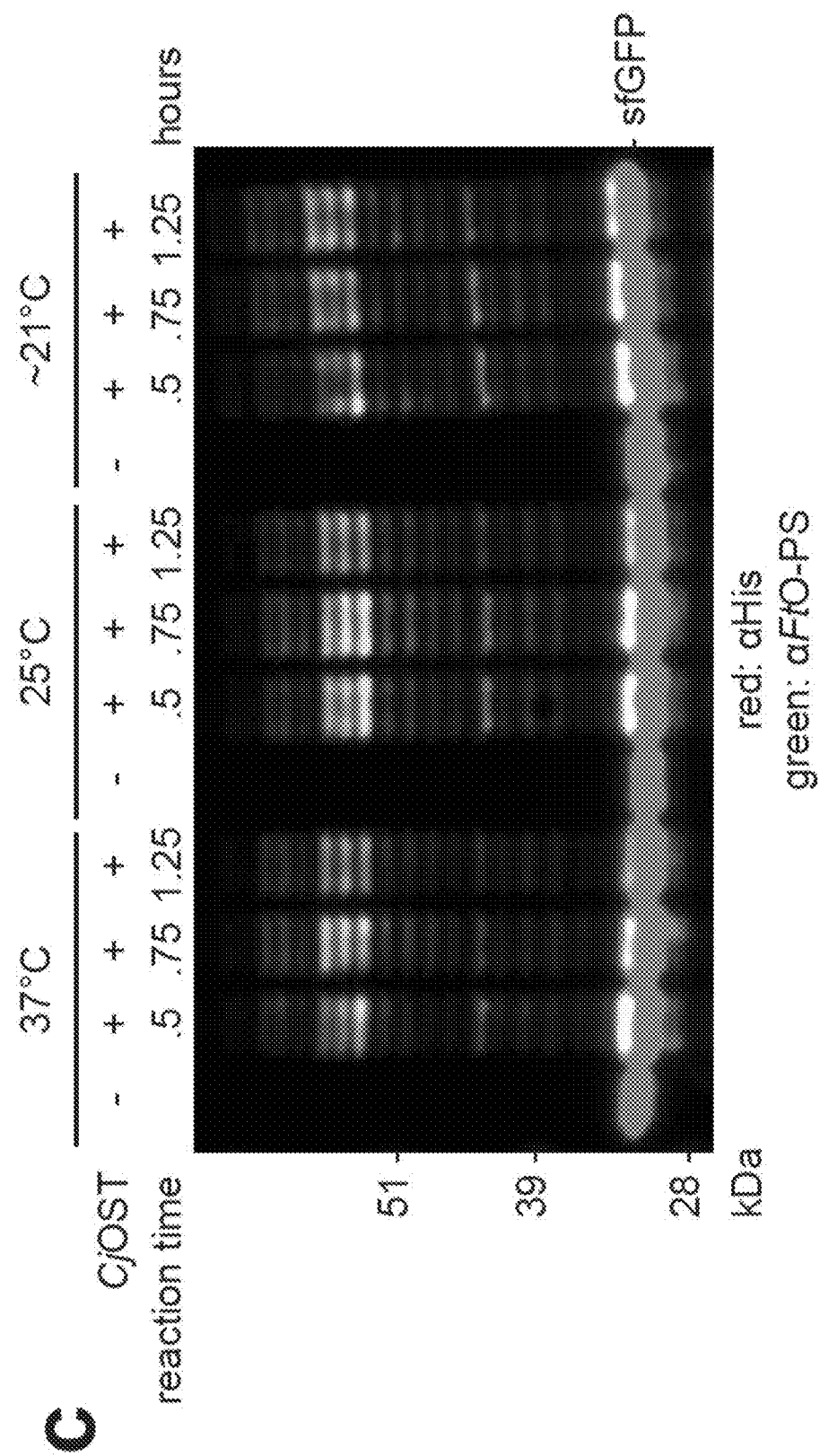
Figure 9:
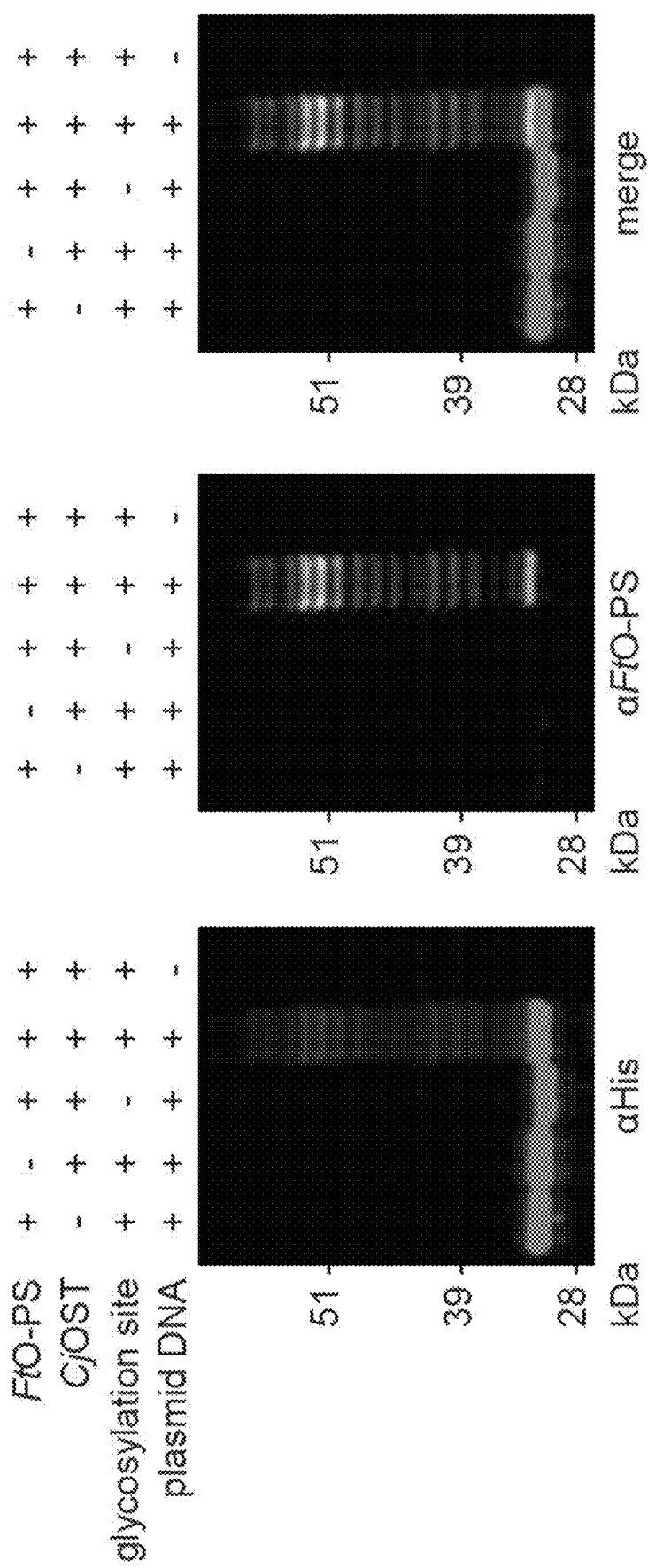
FIG. 9. Detailed Western blot information for FIG. 3a. The anti-His and anti-FtO-PS signals are shown separately as a representative glycosylation Western blot. Images are representative of at least three biological replicates.

The *F. tularensis* Schu S4 O-PS (FtO-PS) is composed of the 826 Da repeating unit Qui4NFm-(GalNAcAN)2-QuiNAc (Qui4NFm: 4,6-dideoxy-4-formamido-D-glucose; GalNAcAN: 2-acetamido-2-deoxy-D-galacturonamide; QuiNAc: 2-acetamido-2,6-dideoxy-D-glucose) [20, 41]. To glycosylate proteins with FtO-PS, we produced an all-in-one iVAX lysate from glycoengineered *E. coli* cells expressing the FtO-PS biosynthetic pathway and the oligosaccharyltransferase enzyme CjPglB. This lysate, which contained lipid-linked FtO-PS and catalytically active CjPlB, was used to catalyze iVAX reactions primed with plasmid DNA encoding sfGFP$^{217\text{-}DQNAT}$. Control reactions in which attachment of the FtO-PS was not expected were performed with lysates from cells that lacked either the FtO-PS pathway or the CjPg1B enzyme. We also tested reactions lacking plasmid encoding the target protein sfGFP$^{217\text{-}DQNAT}$ primed with plasmid encoding sfGFP$^{217\text{-}DQNAT}$, which contained a mutated glycosylation site (AQNAT) that is not modified by CjPg1B [42]. In reactions containing the all-in-one lysate and primed with plasmid encoding sfGFP$^{217\text{-}DQNAT}$, immunoblotting with anti-His antibody or a commercial monoclonal antibody specific to FtO-PS revealed a ladder-like banding pattern (FIG. 3a, FIG. 9). This ladder is characteristic of FtO-PS attachment, resulting from O-PS chain length variability through the action of the Wzy polymerase [16, 20]. Glycosylation of sfGFP$^{217\text{-}DQNAT}$ was observed only in reactions containing a complete glycosylation pathway and the preferred DQNAT (SEQ ID NO: 11) glycosylation sequence (FIG. 3a). This glycosylation profile was reproducible across biological replicates from the same lot of lysate (FIG. 3b, left) and using different lots of lysate (FIG. 3b, right). In vitro protein synthesis and glycosylation was observed after 1 hour, with the amount of conjugated polysaccharide reaching a maximum between 0.75 and 1.25 hours and then decreasing, likely due to the documented instability of O antigen polysaccharide structures upon heating [10, 12] (FIG. 6b). Similar glycosylation reaction kinetics are observed at 37° C., 30° C., 25° C., and room temperature (~21° C.), indicating that iVAX reactions are robust over a range of temperatures (FIG. 6c).

Figure 10:
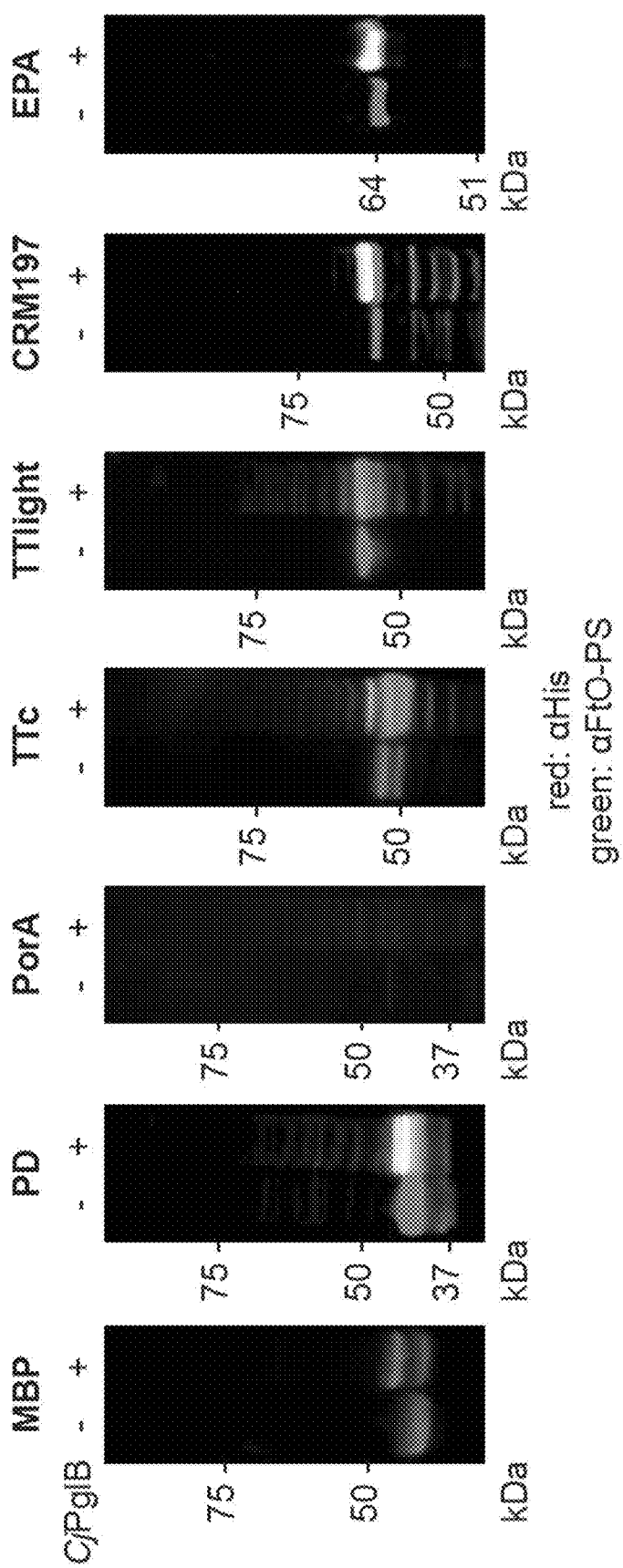
FIG. 10. Production of bioconjugates against *F. tularensis* using PGCT in living *E. coli*. Bioconjugates were produced via PGCT in CLM24 cells expressing CjPglB, the biosynthetic pathway for FtO-PS, and a panel of immunogenic carriers including authentic FDA-approved carriers. We observed low expression of PorA, a membrane protein, and limited glycosylation and laddering of conjugated FtO-PS in all carriers using this method. Images are representative of at least three biological replicates.

Next, we asked whether FDA-approved carriers could be similarly conjugated with FtO-PS in iVAX reactions. We also investigated conjugation of EPA$^{DNNNS\text{-}DQNRT}$, which has been shown to be a safe and effective vaccine component of PGCT-derived vaccines in phase 1 clinical trials [43-45]. Following addition of plasmid DNA encoding MBP$^{4\times DQNAT}$, PD$^{4\times DQNAT}$, PorA$^{4\times DQNAT}$, TTc$^{4\times DQNAT}$, TTlight$^{4\times DQNAT}$, CRM197$^{4\times DQNAT}$, and EPA$^{DNNNS\text{-}DQNRT}$, glycosylation of each with FtO-PS was observed for iVAX reactions enriched with lipid-linked FtO-PS and CjPg1B but not control reactions lacking CjPg1B (FIG. 3c). We observed conjugation of high molecular weight FtO-PS species (on the order of ~10-20 kDa) to all protein carriers tested, which is important as glycan chain length has been shown to play roles in the efficacy of conjugate vaccines [46, 47]. Notably, our attempts to synthesize the same panel of bioconjugates using the established PGCT approach in living *E. coli* yielded less promising results. Specifically, we observed limited expression of the PorA membrane protein in vivo in addition to low levels of FtO-PS conjugation and reduced high molecular weight FtO-PS species in PGCT-derived conjugates compared to their iVAX-derived counterparts (FIG. 10). This indicates that iVAX could provide advantages over PGCT for production of bioconjugate vaccine candidates composed of diverse and potentially membrane-bound carrier proteins with minimal required optimization.

Figure 11:
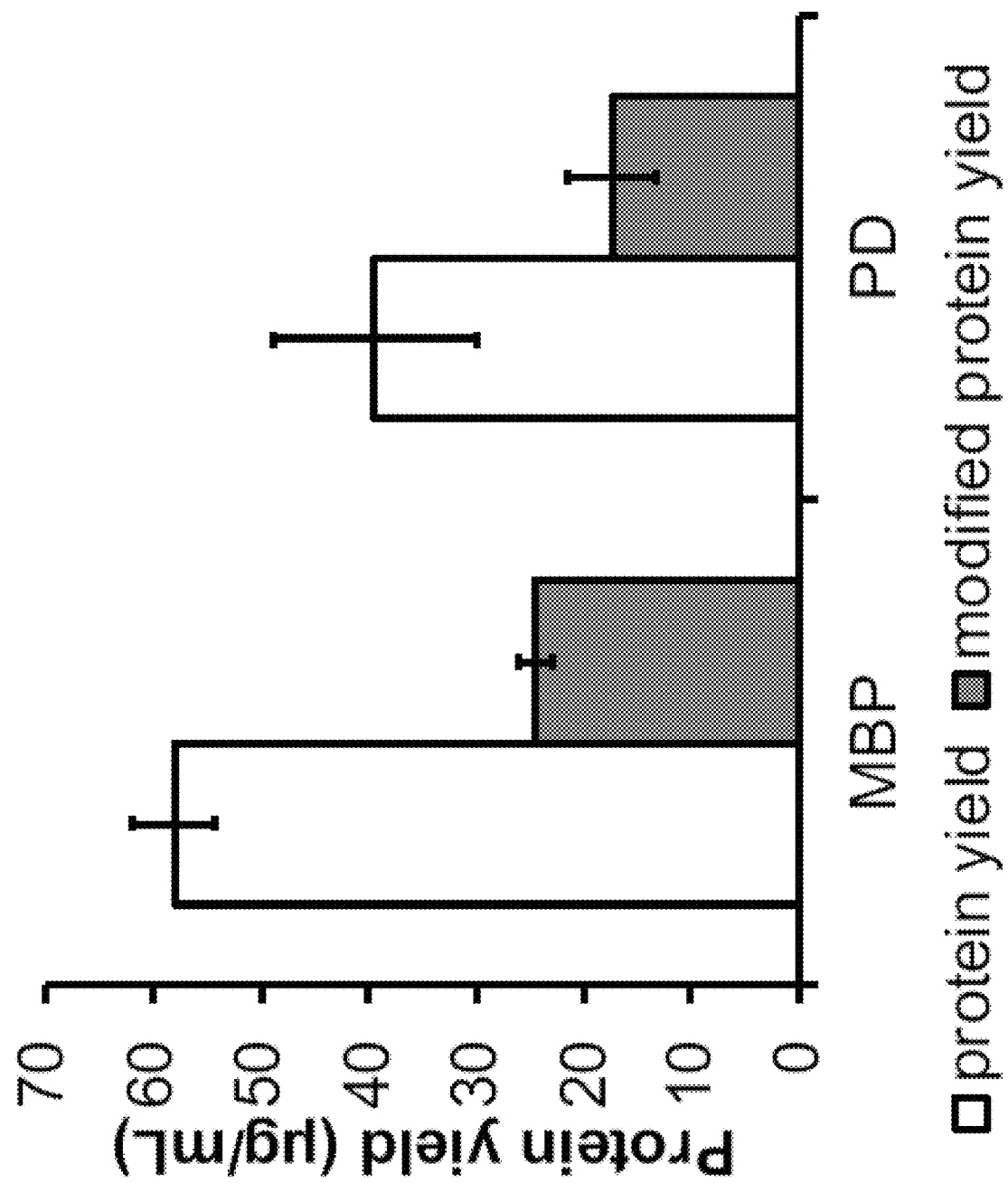
FIG. 11. WAX reactions produce clinically relevant amounts of bioconjugates in 1 h. Protein synthesis and modification with FtO-PS were measured in reactions producing MBP$^{4\times DQNAT}$ and PD$^{4\times DQNAT}$. After ~1 h, reactions produced ~40 µg mL$^{-1}$ protein, as measured via $^{14}$C-leucine incorporation, of which ~20 µg mL$^{-1}$ was modified with the FtO-PS, as determined by densitometry. Values represent means and error bars represent standard errors of biological replicates (n=2).

We found that reactions lasting ~1 hour produced ~20 μg $mL^{-1}$ of glycosylated $MBP^{4\times DQNAT}$ and $PD^{4\times DQNAT}$ as determined by $^{14}C$-leucine incorporation and densitometry analysis (FIG. 11). At these titers, our iVAX reactions can produce up to 20 doses per nit per hour based on recent phase 1 clinical trials demonstrating that 1-10 μg doses of bioconjugate vaccine candidates are well-tolerated and effective in stimulating the production of antibacterial IgGs [43-45]. Hence, clinically relevant doses can be synthesized in just 1 h, making the iVAX platform an attractive option for point-of-care production or prototyping of bioconjugate vaccines.

Figure 12:
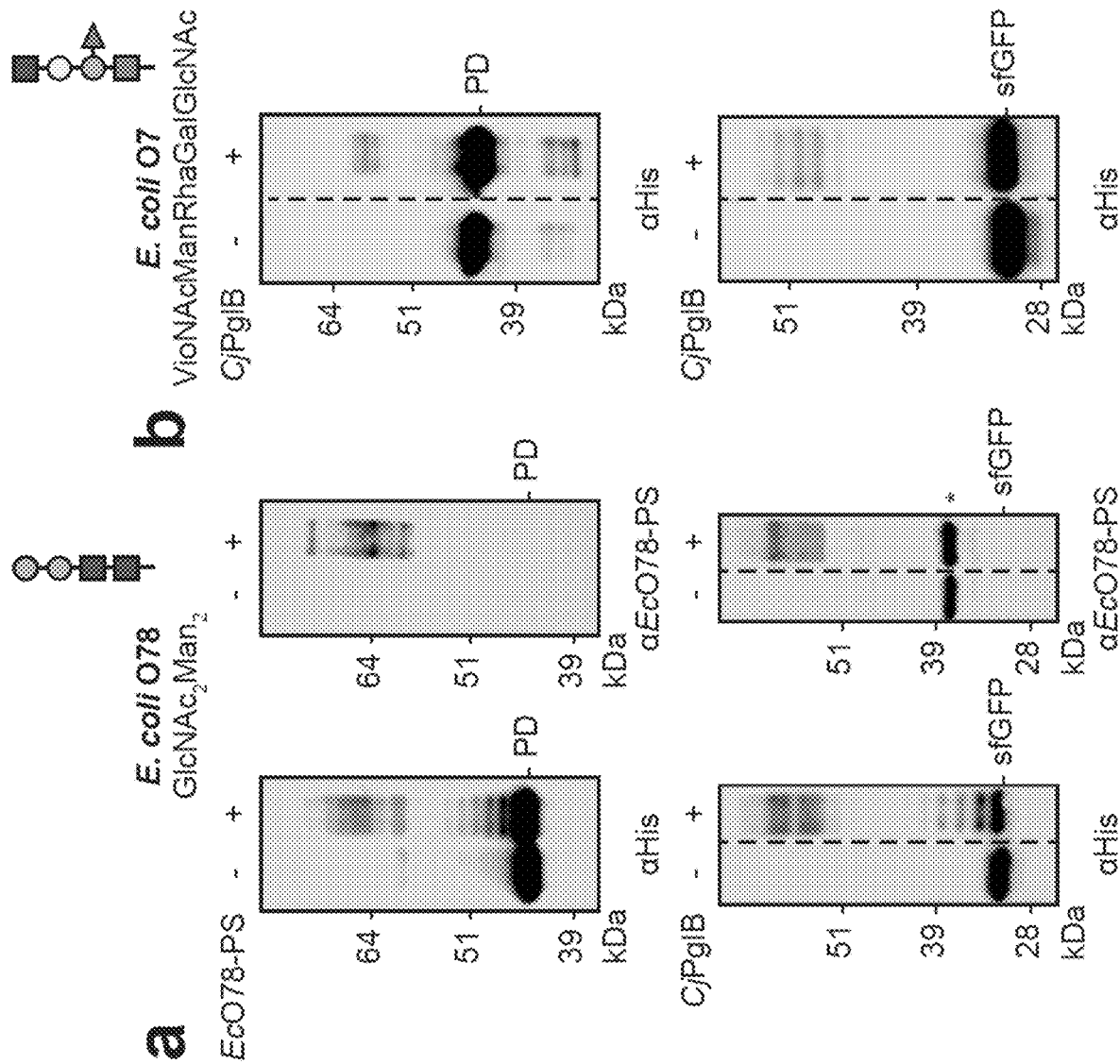
FIG. 12. The iVAX platform is modular and can be used to synthesize diverse bioconjugates. iVAX lysates were prepared from cells expressing CjPglB and biosynthetic pathways for either (a) the *E. coli* O78 antigen or (b) the *E. coli* O7 antigen and used to synthesize PD$^{4\times DQNAT}$ (top) or sfGFP$^{217\text{-}DQNAT}$ (bottom) bioconjugates. The structure and composition of the repeating monomer unit for each antigen is shown. Both polysaccharide antigens are compositionally and, in the case of the O7 antigen, structurally distinct compared to the *F. tularensis* O antigen. If a commercial anti-O-PS serum or antibody was available, it was used to confirm the identity of the conjugated O antigen (α-EcO78 blots, panel a). Asterisk denotes bands resulting from non-specific serum antibody binding. Images are representative of at least three biological replicates. Dashed lines indicate samples are from the same blot with the same exposure.
Figure 13:
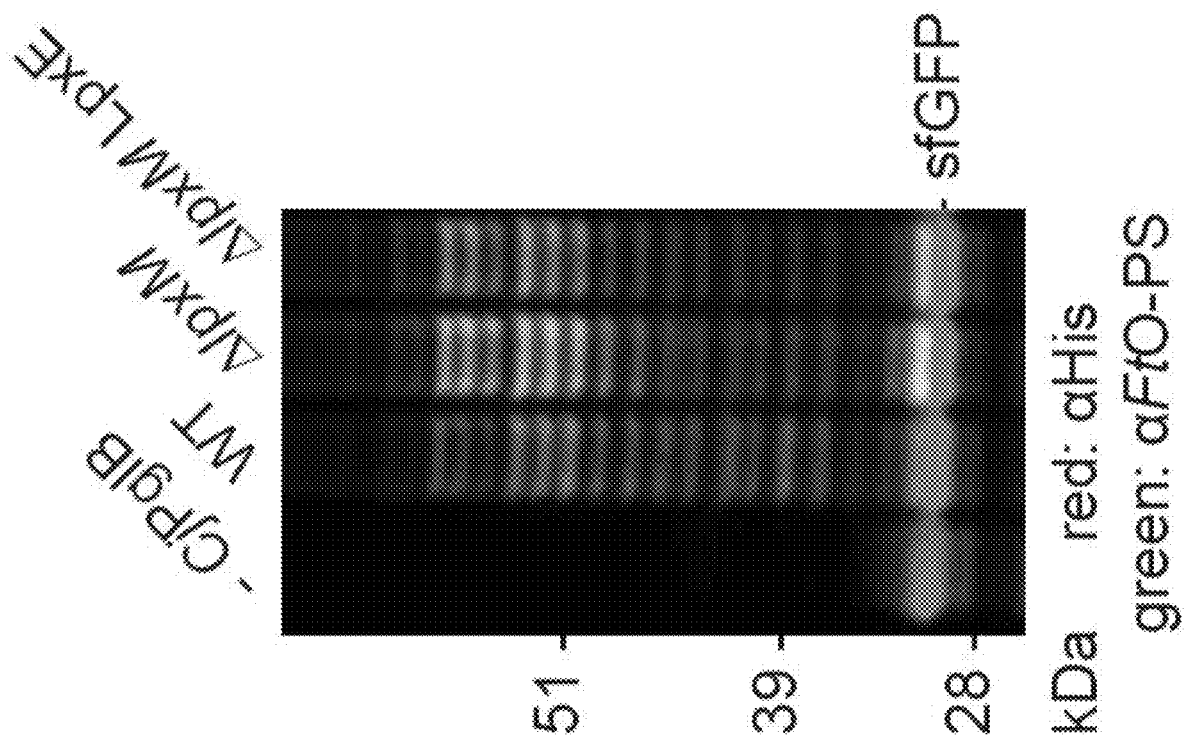
FIG. 13. Lipid A remodeling does not affect glycosylation activity in iVAX reactions. iVAX lysates were prepared from either wild-type CLM24, CLM24 ΔlpxM, or CLM24 ΔlpxM expressing FtLpxE cells also expressing CjPglB and FtO-PS. These all-in-one lysates synthesizing versions of the lipid A molecule with varying structures and toxicities (FIG. 4a) were used in iVAX reactions primed with plasmid encoding sfGFP$^{217\text{-}DQNAT}$. No significant difference in glycosylation activity was observed. Images are representative of at least three biological replicates.
Figure 14:
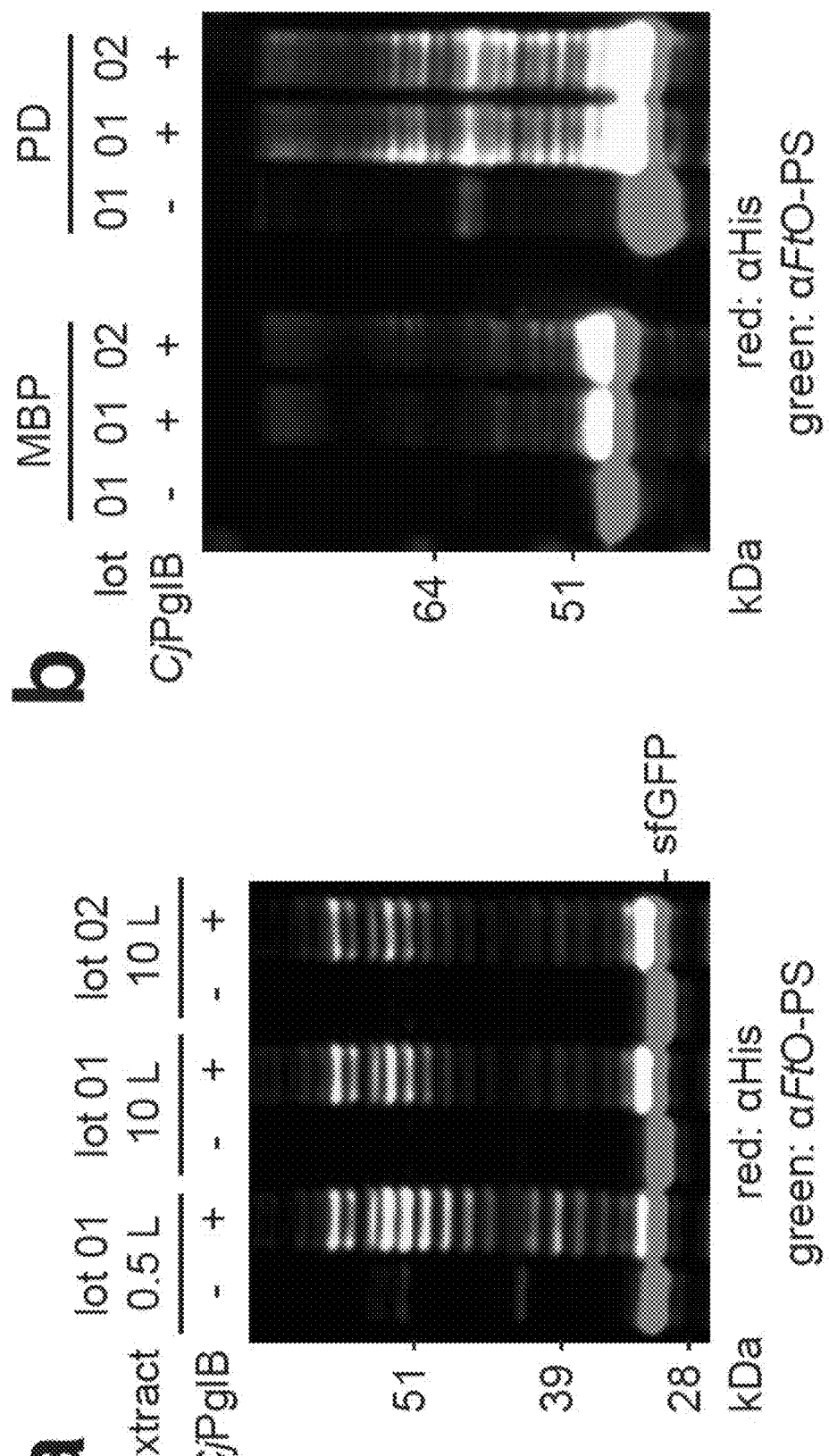
FIG. 14. Scaling of detoxified iVAX lysate production and freeze-dried reactions is reproducible. (a) To generate material for immunizations, fermentations to produce detoxified iVAX lysates were scaled from 0.5 L to 10 L. iVAX reactions were prepared using lysates produced at small or large scale and primed with plasmid encoding sfGFP$^{217\text{-}DQNAT}$. We observed similar levels of glycosylation from lysates derived from 0.5 L and 10 L cultures, and across different batches of lysate produced from 10 L fermentations. (b) For immunizations, we prepared two lots of FtO-PS-conjugated MBP$^{4\times DQNAT}$ and PD$^{4\times DQNAT}$ from 5 mL freeze-dried iVAX reactions. We observed similar levels of purified protein (~200 μg) and FtO-PS modification (>50%, measured by densitometry) across both carriers and lots of material.
Figure 15:
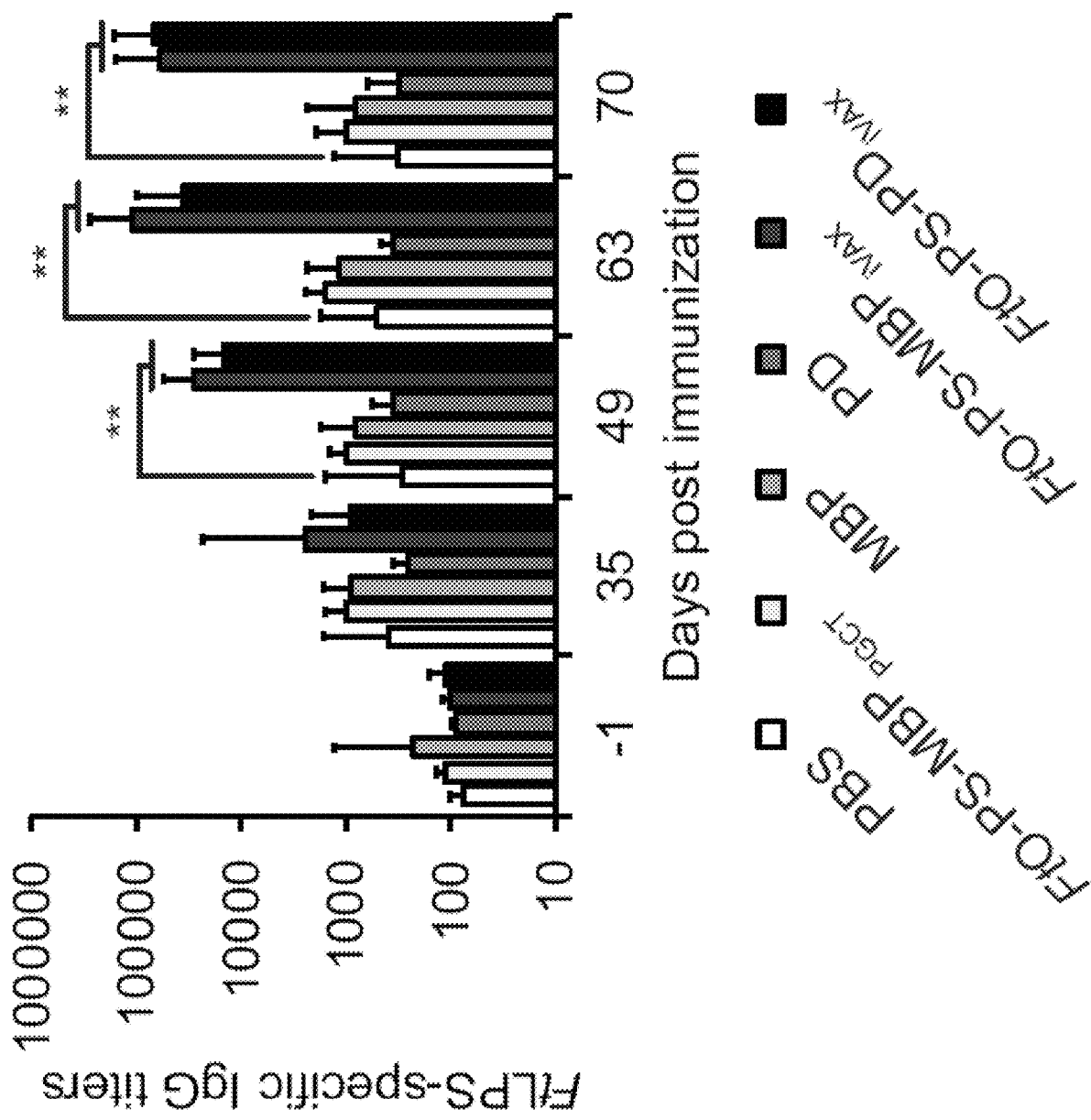
FIG. 15. FtLPS-specific antibody titers in vaccinated mice over time. Six groups of BALB/c mice were immunized subcutaneously with PBS or 7.5 μg of purified, cell-free synthesized aglycosylated MBP$^{4\times DQNAT}$, FtO-PS-conjugated MBP$^{4\times DQNAT}$, aglycosylated PD$^{4\times DQNAT}$, or FtO-PS-conjugated PD$^{4\times DQNAT}$. FtO-PS-conjugated MBP$^{4\times DQNAT}$ prepared in living E. coli cells using PCGT was used as a positive control. Each group was composed of six mice except for the PBS control group, which was composed of five mice. Mice were boosted on days 21 and 42 with identical doses of antigen. FtLPS-specific IgG titers were measured by ELISA in serum collected on day −1, 35, 49, 63, and 70 following initial immunization. iVAX-derived bioconjugates elicited significantly higher levels of FtLPS-specific IgG compared to compared to the PBS control group in serum collected on day 35, 49, and 70 of the study (**p<0.01, Tukey-Kramer HSD). Values represent means and error bars represent standard errors of FtLPS-specific IgGs detected by ELISA.
Figure 16:
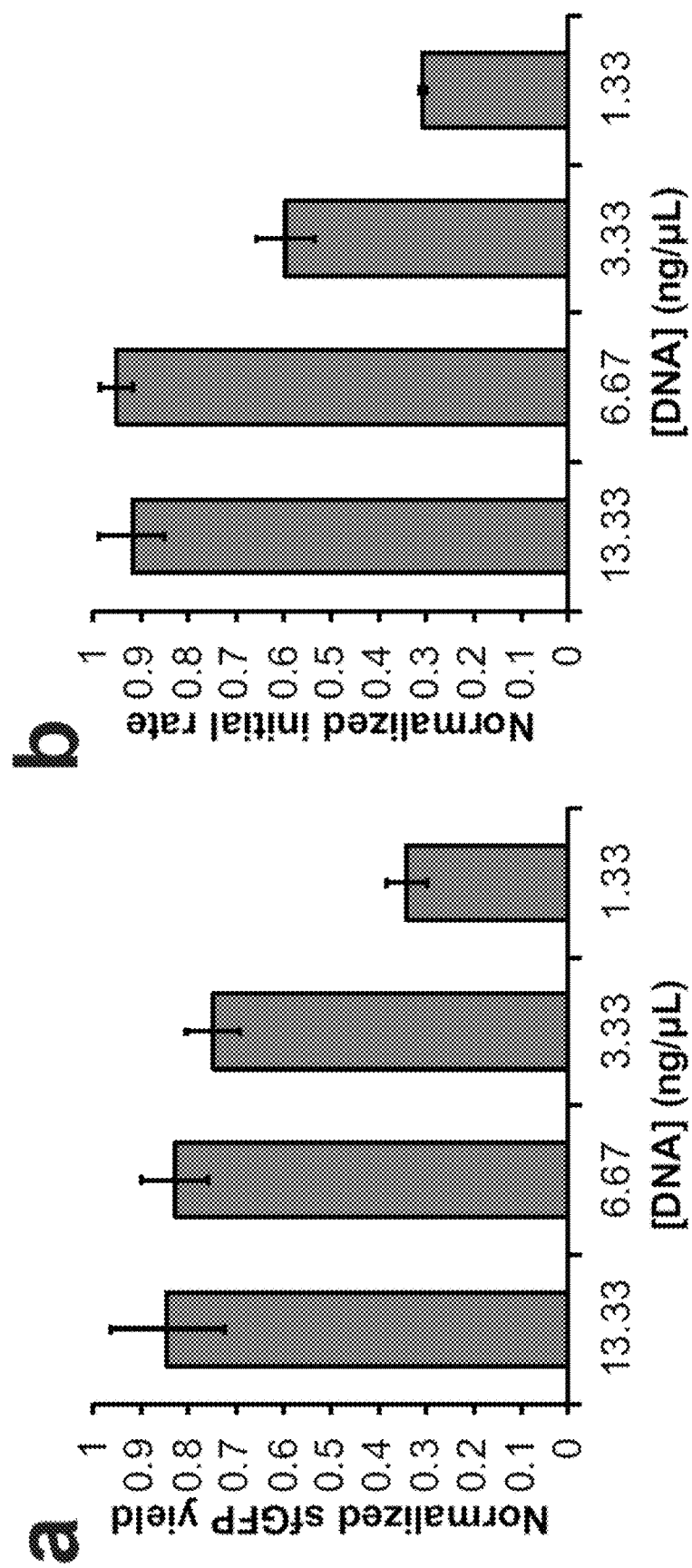
FIG. 16. DNA concentration in iVAX reactions can be reduced without impacting protein synthesis yields or kinetics. iVAX reactions were prepared containing 13.33, 6.67, 3.33, or 1.33 ng/μL plasmid DNA template encoding sfGFP. We observed that both (a) protein synthesis yields after 20 h and (b) initial rates of protein synthesis were conserved with 13.33 or 6.67 ng/μL DNA template. At lower DNA concentrations, DNA template appeared to be limiting as lower protein synthesis yields and initial rates were observed.

To demonstrate the modularity of the iVAX approach for bioconjugate production, we sought to produce bioconjugates bearing O-PS antigens from ETEC *E. coli* strain O78 and UPEC *E. coli* strain O7. *E. coli* O78 is a major cause of diarrheal disease in developing countries, especially among children, and a leading cause of traveler's diarrhea [48], while the O7 strain is a common cause of urinary tract infections [49]. Like the FtO-PS, the biosynthetic pathways for EcO78-PS and EcO7-PS have been described previously and confirmed to produce O-PS antigens with the repeating units $GlcNAc_2Man_2$ [50] and VioNAcManRhaGalGlcNAc (GlcNAc: N-acetylglucosamine; Man: mannose; VioNAc: N-acetylviosamine; Rha: rhamnose; Gal: galactose) [51], respectively. Using all-in-one iVAX lysates from cells expressing CjPg1B and either the EcO78-PS and EcO7-PS pathways in reactions primed with $PD^{4\times DQNAT}$ or $sfGFP^{217\text{-}DQNAT}$ plasmids, we observed carrier glycosylation when both lipid-linked O-PS and CjPg1B were present in the reactions (FIG. 12). Collectively, our results demonstrate the production of bioconjugates against multiple bacterial pathogens enabled by coordinated in vitro carrier protein synthesis and O-PS glycosylation of licensed vaccine carrier proteins.

Portable, freeze-dried iVAX reactions containing endotoxin-edited lysates. For the iVAX technology to be an effective portable vaccine production platform, iVAX-derived bioconjugates must be demonstrated as safe, and iVAX reactions must be amenable to storage and distribution under ambient conditions. A key challenge inherent in using any *E. coli*-based system for biopharmaceutical production is the presence of lipid A, or endotoxin, which is known to contaminate protein products Immune recognition of lipid A by toll-like receptor 4 (TLR4) results in production of proinflammatory cytokines such as tumor necrosis factor alpha and interleukin-1 beta [52] that are needed to fight infection, but can cause lethal septic shock at high levels [53]. As a result, the amount of endotoxin in formulated biopharmaceuticals is regulated by the United States Pharmacopeia (USP), US Food and Drug Administration (FDA), and the European Medicines Agency (EMEA) [54]. Because our iVAX reactions rely on lipid-associated components, such as CjPg1B and FtO-PS, standard detoxification approaches involving the removal of lipid A [55] could compromise the activity or concentration of our glycosylation components. Such removal strategies also increase cost and processing complexities, which could limit the economic accessibility and utility of iVAX reactions in resource-limited settings.

Figure 4:
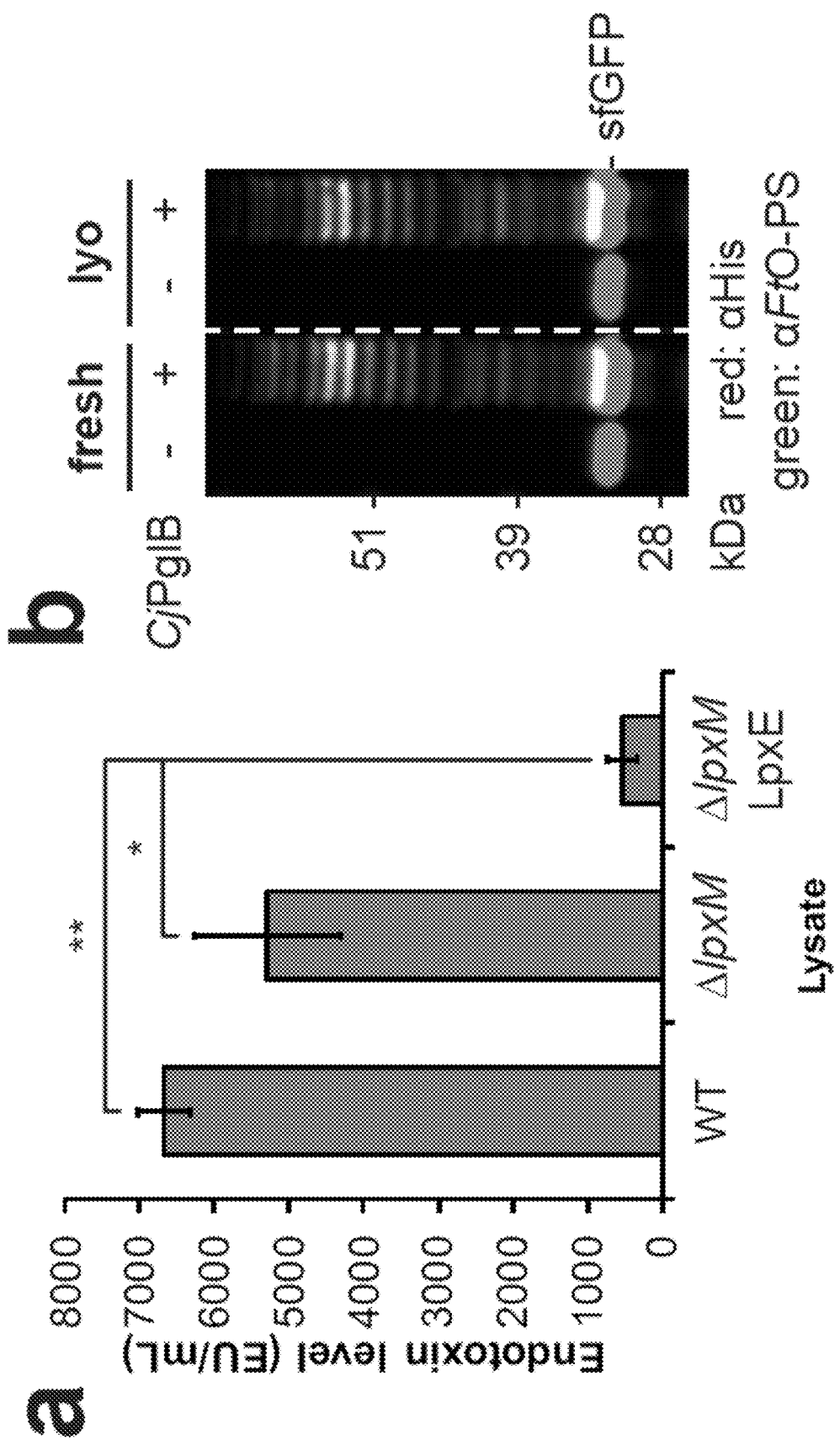
FIG. 4. Detoxified, lyophilized iVAX reactions produce bioconjugates that are comparable to those made using state-of-the-art technologies. (a) iVAX lysates were detoxified via deletion of lpxM and expression of *F. tularensis* LpxE in the source strain for lysate production. This strain engineering resulted in production of a pentaacylated, monophosporylated lipid A molecule with reduced endotoxin activity. *p=0.019 and **p=0.003, as determined by two-tailed t-test. (b) Identical iVAX reactions producing sfGFP$^{217\text{-}DQNAT}$ were run immediately or following lyophilization and rehydration. Glycosylation activity was preserved following lyophilization, demonstrating the potential of iVAX reactions for portable biosynthesis of bioconjugate vaccines.

To address this issue, we sought to modify the structure of lipid A to reduce its toxicity but maintain its adjuvanticity. For example, monophosphoryl lipid A (MPL) from *Salmonella minnesota*R595 is an approved adjuvant composed of a mixture of monophosphorylated lipids, with the primary component being pentaacylated, monophosphorylated lipid A [56]. Several groups have recently reported the ability to detoxify the lipid A molecule through strain engineering [57, 58]. In particular, the deletion of the acyltransferase gene lpxM and the overexpression of the *F. tularensis* phosphatase LpxE in *E. coli* has been shown to result in the production of nearly homogenous pentaacylated, monophosphorylated lipid A with significantly reduced toxicity [57]. Similarly, when we produced lysates from the CLM24 ΔlpxM strain expressing FtLpxE and the FtO-PS glycosylation pathway, we observed significantly decreased levels of toxicity compared to wild type CLM24 lysates expressing CjPg1B and FtO-PS (FIG. 4*a*) as measured by human TLR4 activation in HEK-Blue hTLR4 reporter cells [58]. It should be noted that the structural editing of lipid A did not affect the activity of the membrane-bound CjPg1B and FtO-PS components in iVAX reactions (FIG. 13). By engineering the chassis strain for lysate production, we produced iVAX lysates with endotoxin levels <1,000 EU/mL, which is within the range of reported values for commercial protein-based vaccine products (0.288-180,000 EU/mL) [54].

A major limitation of traditional conjugate vaccines is that they must be refrigerated [12, 13], making it difficult to distribute these vaccines to remote or resource-limited settings. The ability to freeze-dry detoxified iVAX reactions for ambient temperature storage and distribution could alleviate the logistical challenges associated with refrigerated supply chains that are required for existing vaccines. To investigate this possibility, identical iVAX reactions producing $sfGFP^{217\text{-}DQNAT}$ were run immediately or following lyophilization and rehydration. In both cases, FtO-PS is attached to the target protein when CjPg1B was present in the reaction (FIG. 4*b*). Detoxified, freeze-dried iVAX reactions can be scaled to 5 mL for reproducible FtO-PS-conjugated $MBP^{4\times DQNAT}$ and $PD^{4\times DQNAT}$ with modification efficacies similar to those observed without freeze-drying (FIG. 14). The ability to lyophilize iVAX reactions without compromising bioconjugate synthesis levels highlights the potential for portable, on-demand vaccine production.

In vitro synthesized bioconjugates elicit bactericidal pathogen-specific antibodies in mice. To validate the efficacy of bioconjugates produced using the iVAX platform, we next evaluated the ability of iVAX-derived bioconjugates to elicit anti-FtLPS antibodies in mice. Importantly, we found that BALB/c mice receiving iVAX-derived FtO-PS-conjugated $MBP^{4\times DQNAT}$ and $PD^{4\times DQNAT}$ produced high titers of FtLPS-specific IgG antibodies, which were significantly elevated compared to the titers measured in the sera of control mice receiving PBS or aglycosylated $MBP^{4\times DQNAT}$ and $PD^{4\times DQNAT}$ carrier proteins (FIG. 5*a*, FIG. 15). Interestingly, the IgG titers measured in sera from mice receiving glycosylated $MBP^{4\times DQNAT}$ derived from PGCT were similar to the titers observed in the control groups (FIG. 5*a*, FIG. 15), in line with the weaker glycosylation of this candidate relative to its iVAX-derived counterpart (FIG. 10). Notably, both MBP and PD bioconjugates produced using iVAX elicited similar levels of IgG production and neither resulted in any observable adverse events in mice, confirming the modularity and safety of the technology for producing bioconjugate vaccine candidates.

We further characterized IgG titers by analysis of IgG1 and IgG2a subtypes and found that iVAX-derived FtO-PS-conjugated MBP$^{4\times DQNAT}$ and PD$^{4\times DQNAT}$ boosted production of IgG1 antibodies by >2 orders of magnitude relative to all control groups and to glycosylated MBP$^{4\times DQNAT}$ derived from PGCT (FIG. 5b). This analysis also revealed that our iVAX-derived bioconjugates elicited a strongly Th2-biased (IgG1>>IgG2a) response, which is characteristic of most conjugate vaccines [59]. Taken together, these results provide clear evidence that the iVAX platform supplies vaccine candidates that are capable of eliciting strong, pathogen-specific humoral immune responses and recapitulate the Th2 bias that is characteristic of licensed conjugate vaccines.

To determine if the IgG antibodies elicited by the iVAX-derived bioconjugates were functional, we next screened mouse sera for *F. tularensis* killing activity using a serum bactericidal assay (SBA). Mice immunized with iVAX-derived bioconjugates clearly had opsonically active antibodies that mediated killing of *F. tularensis* LVS Iowa, whereas mice receiving empty OMVs or PBS had significantly less killing activity.

Discussion

In this work we have established iVAX, a cell-free platform for portable, on-demand production of bioconjugate vaccines. We show that iVAX reactions can be detoxified to ensure the safety of bioconjugate vaccine products, freeze-dried for cold chain-independent distribution, and re-activated by simply adding water. As a model vaccine candidate, we show that anti-*F. tularensis* bioconjugates derived from freeze-dried, endotoxin-edited iVAX reactions elicited pathogen-specific IgG antibodies in mice as part of a Th2-biased immune response characteristic of licensed conjugate vaccines.

The iVAX platform has several exciting features. First, iVAX is modular, which we have demonstrated through the interchangeability of (i) carrier proteins, including those used in licensed conjugate vaccines, and (ii) bacterial O-PS antigens from *F. tularensis* subsp. *tularensis* (type A) Schu S4, ETEC *E. coli* O78, and UPEC *E. coli* O7. Further expansion of the O-PS pathways used in iVAX should be relatively straightforward given the commonly observed clustering of polysaccharide biosynthetic genes in the genomes of pathogenic bacteria [60]. This feature should make iVAX an attractive option for rapid, de novo development of bioconjugate vaccine candidates in response to a disease outbreak or against emerging drug resistant bacteria.

Second, iVAX reactions are inexpensive, costing ~$11.75 mL$^{-1}$ (data not shown) with the ability to synthesize ~20 μg bioconjugate mL$^{-1}$ (FIG. 11). Assuming a dose size of 10 μg, our iVAX reactions can produce a vaccine dose for S5.88. For comparison, the CDC cost per dose for conjugate vaccines ranges from $9.23 for the TT conjugate ActHIB® to $73.83 and $131.77 for the CRM197 conjugates Menveo® and Prevnar 13® [61]. We anticipate that the low cost of the iVAX platform will encourage its adoption.

Figure 5:
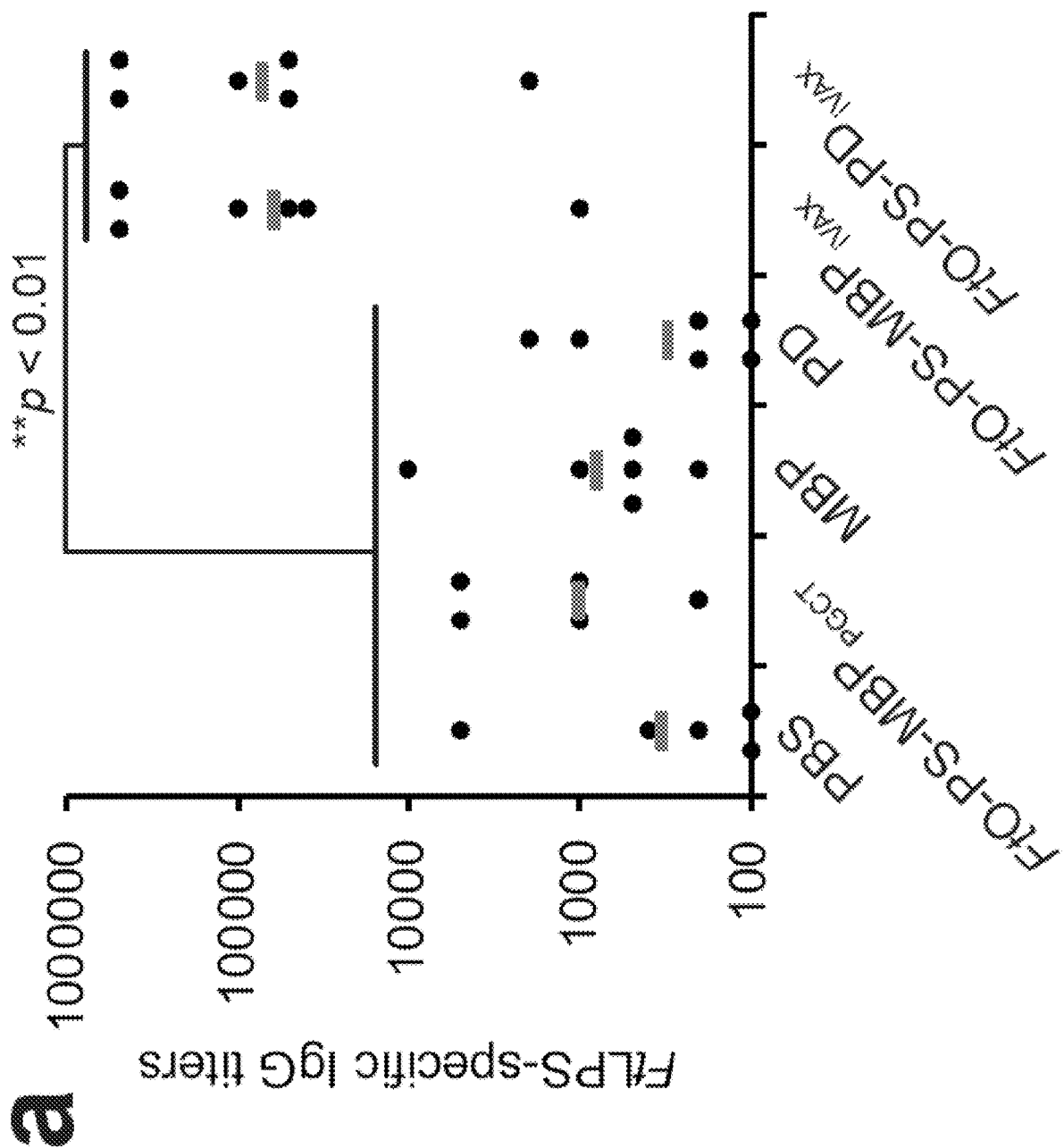
FIG. 5. iVAX-derived bioconjugates elicit bactericidal antibodies specific to FtLPS in mice. (a) FtLPS-specific IgG titers were measured by ELISA in endpoint (day 70) serum of individual mice (black dots) and mean titers of each group (red lines). Six groups of BALB/c mice were immunized subcutaneously with PBS or 7.5 µg of purified, cell-free synthesized aglycosylated MBP$^{4\times DQNAT}$, FtO-PS-conjugated MBP$^{4\times DQNAT}$, aglycosylated PD$^{4\times DQNAT}$, or FtO-PS-conjugated PD$^{4\times DQNAT}$. FtO-PS-conjugated MBP$^{4\times DQNAT}$ prepared in living *E. coli* cells using PCGT was used as a positive control. Each group was composed of six mice except for the PBS control group, which was composed of five mice. Mice were boosted on days 21 and 42 with identical doses of antigen. iVAX-derived bioconjugates elicited significantly higher levels of FtLPS-specific IgG compared to all other groups (p<0.01, Tukey-Kramer HSD). (b) IgG1 and IgG2a subtype titers measured by ELISA from endpoint serum revealed that iVAX-derived bioconjugates boosted production of FtO-PS-specific IgG1 compared to all other groups tested (p<0.01, Tukey-Kramer HSD). This indicates that iVAX bioconjugates elicited a Th2-biased immune response typical of most conjugate vaccines. Values represent means and error bars represent standard errors of FtLPS-specific IgGs detected by ELISA. (c) FtLPS-specific IgGs are bactericidal against the *F. tularensis* LVS. Values represent averages and error bars represent standard deviations of bactericidal activity from individual mice in each immunization group.
Figure 5:
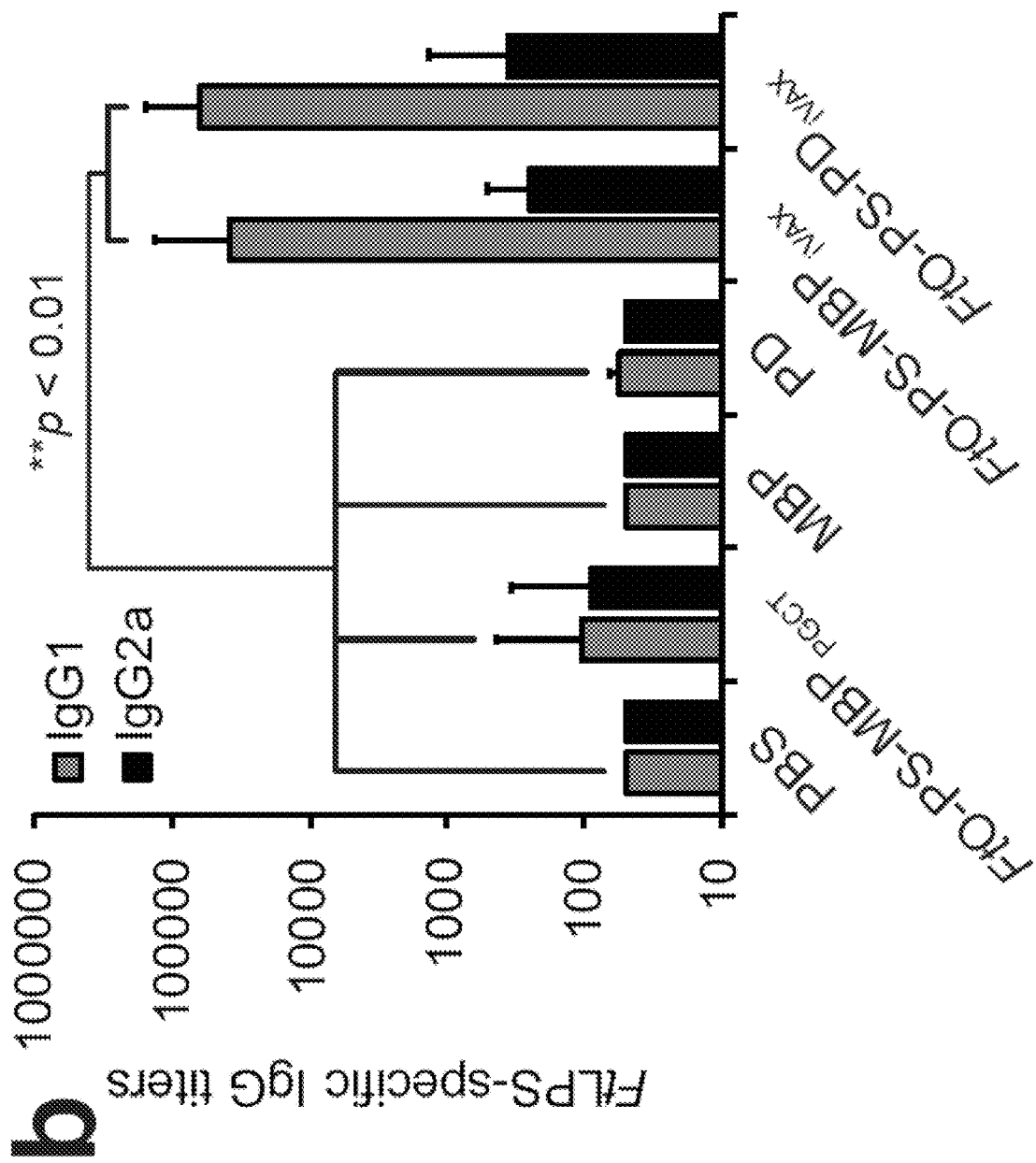

Third, and rather interestingly, we observed that iVAX-derived bioconjugates were significantly more effective at eliciting FtLPS-specific IgGs than a bioconjugate derived from living *E. coli* cells using PGCT (FIG. 5). One possible explanation for this increased effectiveness is the more extensive glycosylation that we observed for the in vitro expressed carriers, with greater carbohydrate loading per protein and decoration with a broader range of higher molecular weight FtO-PS species compared to their PGCT-derived counterparts. This is consistent with previous reports of PGCT-derived anti-*F. tularensis* bioconjugates which show that increasing the ratio of glycan to protein in bioconjugates result in enhanced protection against *F. tularensis* in a rat inhalation model of tularemia [21]. A number of studies have demonstrated that the degree of epitope density and glycan chain length are critical factors influencing the magnitude of the ensuing epitope-specific immune response [46, 47, 62-64]. These results as well as our own point to the fact that a deeper understanding of important immunogen design features, which could be readily controlled and varied using the iVAX platform, will be crucial to producing better defined, more effective conjugate vaccine candidates in the future.

In summary, iVAX provides an exciting new approach for portable, on-demand biomanufacturing of conjugate vaccines. A key feature of iVAX is that seamlessly integrates CFPS and glycosylation with bacterial polysaccharide antigens in one-pot reactions that can be freeze-dried for refrigeration-free storage and transportation, and can be re-activated for point-of-use vaccine synthesis simply by adding water. This not only alleviates cold chain requirements, which is important for delivering medicines on demand in regions with limited infrastructure and could minimize vaccine losses due to spoilage, but also provides a unique means for rapidly responding to pathogen outbreaks and emergent threats. As a result, we believe that the iVAX technology platform, along with an emerging set of collective efforts in making biomedicines on-demand [24, 25, 65-67], have the potential for promoting better access to costly drugs through decentralized production.

Methods

Bacterial strains and plasmids. NEB 5-alpha was used for plasmid cloning and purification. The CLM24 or CLM24 ΔlpxM strains were used as the source strain for preparing lysates with and without selectively enriched glycosylation components. CLM24 was used as the cassis for expressing bioconjugates in vivo using PGCT. CLM24 is a glyco-optimized derivative of W3110 that carries a deletion in the gene encoding the WaaL ligase, thus facilitating the accumulation of preassembled glycans on Und-PP [16]. CLM24 ΔlpxM has an endogenous acyltransferase deletion and serves as the chassis strain for production of detoxified lysates.

The CLM24 ΔlpxM strain was generated using the Datsenko-Wanner gene knockout method [68]. Briefly, CLM24 cells were transformed with the pKD46 plasmid encoding the λ red system. Transformants were grown to an OD$_{600}$ of 0.5-0.7 in 25 mL LB-Lennox media (10 g L$^{-1}$ tryptone, 5 g L$^{-1}$ yeast extract and 5 g L$^{-1}$ NaCl) with 50 μg mL$^{-1}$ carbenicillin at 30° C. harvested and washed three times with 25 mL ice-cold 10% glycerol to make them electrocompetent, and resuspended in a final volume of 100 μL 10% glycerol. In parallel, a lpxM knockout cassette was generated by PCR amplifying the kanamycin resistance cassette from pKD4 with forward and reverse primers with homology to lpxM. Electrocompetent cells were transformed with 400 ng of the lpxM knockout cassette and plated on LB agar with 30 μg mL$^{-1}$ kanamycin for selection of resistant colonies. Plates were grown at 37° C. to cure cells of the pKD46 plasmid. Colonies that grew on kanamycin were confirmed to have acquired the knockout cassette via colony PCR and DNA sequencing. These confirmed colonies were then transformed with pCP20 to remove the kanamycin resistance gene via Flp-FRT recombination. Transformants were plated on LB agar with 50 μg mL$^{-1}$ carbenicillin. Following selection, colonies were grown in liquid culture at 42° C. to cure cells of the pCP20 plasmid. Colonies were confirmed to have lost both lpxM and the knockout cassette via colony PCR and DNA sequencing and confirmed to have lost both kanamycin and carbenicillin resistance via replica plating on LB agar plates with carbenicillin and kanamycin. To enable overexpression of *F. tualrensis* LpxE, the lpxE gene was inserted into the pSF-CjPglB vector downstream of pglB via Gibson assembly. Lysate detoxification resulting from deletion of lpxM and overexpression of LpxE was confirmed using the TLR4 activation assay described below.

Plasmids pJL1-MBP$^{4\times DQNAT}$, pJL1-PD$^{4\times DQNAT}$, pJL1-PorA$^{4\times DQNAT}$, pJL1-TTc$^{4\times DQNAT}$, pJL1-TTlight$^{4\times DQNAT}$, pJL1-CRM197$^{4\times DQNAT}$, pJL1-TT$^{4\times DQNAT}$ and generated via PCR amplification and subsequent Gibson Assembly of a codon optimized gene construct purchased from IDT with a C-terminal 4×DQNAT (SEQ ID NO: 12)-6×His tag between the NdeI and SalI restriction sites in the pJL1 vector. Plasmid pJL1-EPA$^{DNNNS\text{-}DQNRT}$ was constructed using the same approach, but without the addition of a C-terminal 4×DQNAT (SEQ ID NO: 12)-6×His tag. Plasmids pTrc99s-ssDsbA-MBP$^{4\times DQNAT}$, pTrc99s-ssDsbA-PD$^{4\times DQNAT}$, pTrc99s-ssDsbA-PorA$^{4\times DQNAT}$, pTrc99s-ssDsbATTc$^{4\times DQNAT}$, pTrc99s-ssDsbA-TTlight$^{4\times DQNAT}$, and pTrc99s-ssDsbA-EPA$^{4\times DQNAT}$ were then created via PCR amplification of each carrier protein gene and insertion into the pTrc99s vector between the Ncol and HindIII restriction sites via Gibson Assembly. Plasmid pSF-CjPg1B-LpxE was constructed using a similar approach, but via insertion of the lpxE gene from pE [58] between the NdeI and NsiI restriction sites in the pSF vector. Inserts were amplified via PCR using Phusion® High-Fidelity DNA polymerase (NEB) with forward and reverse primers designed with the NEBuilder® Assembly Tool (nebuilder.neb.com) and purchased from IDT. The pJL1 vector (Addgene 69496) was digested using restriction enzymes NdeI and SalI-HF® (NEB). The pSF vector was digested using restriction enzymes NdeI and NotI (NEB). PCR products were gel extracted using an EZNA Gel Extraction Kit (Omega Bio-Tek), mixed with Gibson assembly reagents and incubated at 50° C. for 1 hour. Plasmid DNA from the Gibson assembly reactions were transformed into *E. coli* NEB 5alpha cells and circularized constructs were selected using kanamycin at 50 μg ml$^{-1}$ (Sigma). Sequence-verified clones were purified using an EZNA Plasmid Midi Kit (Omega Bio-Tek) for use in FD-CF reactions.

S30 lysate preparation. *E. coli* CLM24 source strains were grown in 2×YTP media (10 g/L yeast extract, 16 g/L tryptone, 5 g/L NaCl, 7 g/L $K_2HPO_4$, 3 g/L $KH_2PO_4$, pH 7.2) in shake flasks (1 L scale) or a Sartorius Stedim BIOSTAT Cplus bioreactor (10 L scale) at 37° C. Protein synthesis yields and glycosylation activity were reproducible across different batches of lysate at both small (FIG. 3*b*) and large scale (FIG. 14*a*). To generate CjPg1B-enriched lysate, CLM24 cells carrying plasmid pSF-CjPg1B [69] was used as the source strain. To generate FtO-PS-enriched lysates, CLM24 carrying plasmid pGAB2 [20] was used as the source strain. To generate one-pot lysates containing both CjPg1B and the FtO-PS, EcO78-PS, or EcO7-PS, CLM24 carrying pSF-CjPg1B and one of the following bacterial O-PS biosynthetic pathways was used as the source strain: pGAB2 (FtO-PS), pMW07-O78 (EcO78-PS), and pJHCV32 (EcO7-PS). CjPg1B expression was induced at an $OD_{600}$ of 0.8-1.0 with 0.02% (w/v) L-arabinose and cultures were moved to 30° C. Cells were grown to a final $OD_{600}$ of 3.0, at which point cells were pelleted by centrifugation at 5,000×g for 15 mM at 4° C. Cell pellets were then washed three times with cold S30 buffer (10 mM Tris-acetate pH 8.2, 14 mM magnesium acetate, 60 mM potassium acetate) and pelleted at 5000×g for 10 mM at 4° C. After the final wash, cells were pelleted at 7000×g for 10 mM at 4° C., weighed, flash frozen in liquid nitrogen, and stored at −80° C. To make cell lysate, cell pellets were resuspended to homogeneity in 1 mL of S30 buffer per 1 g of wet cell mass. Cells were disrupted via a single passage through an Avestin EmulsiFlex-B15 (1 L scale) or EmulsiFlex-C3 (10 L scale) high-pressure homogenizer at 20,000-25,000 psi. The lysate was then centrifuged twice at 30,000×g for 30 mM to remove cell debris. Supernatant was transferred to clean microcentrifuge tubes and incubated at 37° C. with shaking at 250 rpm for 60 min Following centrifugation (15,000×g) for 15 mM at 4° C., supernatant was collected, aliquoted, flash-frozen in liquid nitrogen, and stored at −80° C. S30 lysate was active for about 3 freeze-thaw cycles and contained ~40 g/L total protein as measured by Bradford assay.

Cell-free protein synthesis. CFPS reactions were carried out in 1.5 mL microcentrifuge tubes (15 μL scale), 15 mL conical tubes (1 mL scale), or 50 mL conical tubes (5 mL scale) with a modified PANOx-SP system [70]. The CFPS reaction mixture consists of the following components: 1.2 mM ATP; 0.85 mM each of GTP, UTP, and CTP; 34.0 μg mL$^{-1}$ L-5-formyl-5, 6, 7, 8-tetrahydrofolic acid (folinic acid); 170.0 mg mL$^{--1}$ of *E. coli* tRNA mixture; 130 mM potassium glutamate; 10 mM ammonium glutamate; 12 mM magnesium glutamate; 2 mM each of 2.0 amino acids; 0.4 mM nicotinamide adenine dinucleotide (NAD); 0.27 mM coenzyme-A (CoA); 1.5 mM spermidine; 1 mM putrescine; 4 mM sodium oxalate; 33 mM phosphoenolpyruvate (PEP); 57 mM HEPES; 13.3 μg mL plasmid; and 27% v/v of cell lysate. For reaction volumes mL, plasmid was added at 6.67 μg mL$^{-1}$, as this lower plasmid concentration conserved reagents with no effect on protein synthesis yields or kinetics (FIG. 16). For expression of PorA, reactions were supplemented with Nanodiscs at 1 μg mL$^{-1}$, which were prepared as previously described [33] or purchased (Cube Biotech). For expression of CRM197$^{4\times DQNAT}$, CFPS was carried out at 25° C. for 20 hours, unless otherwise noted. For all other carrier proteins, CFPS was run at 30° C. for 20 hours, unless otherwise noted.

For expression of TT$^{4\times DQNAT}$, which contains intermolecular disulfide bonds, CFPS was carried out under oxidizing conditions. For oxidizing conditions, lysate was preconditioned with 750 μM iodoacetamide at room temperature for 30 min to covalently bind free sulfhydryls (—SH) and the reaction mix was supplemented with 200 mM glutathione at a 4:1 ratio of oxidized and reduced forms and 60.5 μM recombinant *E. coli* DsbC [37].

In vitro bioconjugate vaccine expression (iVAX). For in vitro expression and glycosylation of acceptor proteins in crude lysates, a two-phase scheme was implemented. In the first phase, CFPS was carried out for 15 mM at 25-30° C. as described above. In the second phase, protein glycosylation was initiated by the addition of $MnCl_2$ and DDM at a final concentration of 25 mM and 0.1% (w/v), respectively, and allowed to proceed at 30° C. for a total reaction time of 1-2 hours. Protein synthesis yields and glycosylation activity were reproducible across biological replicates of iVAX reactions at both small (FIG. 3*b*) and large scale (FIG. 14*b*). Reactions were then centrifuged at 20,000×g for 10 min to remove insoluble or aggregated protein products and the supernatant was analyzed by SDS-PAGE and Western blotting.

Purification of aglycosylated and glycosylated carriers from iVAX reactions was carried out using Ni-NTA agarose (Qiagen) according to manufacturer's protocols. Briefly, 0.5 mL Ni-NTA agarose per 1 mL cell-free reaction mixture was equilibrated in Buffer 1 (300 mM NaCl 50 mM NaH$_2$PO$_4$) with 10 mM imidazole. Soluble fractions from iVAX reactions were loaded on Ni-NTA agarose and incubated at 4° C. for 2-4 hours to bind 6×His-tagged protein. Following incubation, the cell-free reaction/agarose mixture was loaded onto a polypropylene column (BioRad) and washed twice with 6 column volumes of Buffer 1 with 20 mM imidazole. Protein was eluted in 4 fractions, each with 0.3 mL Buffer 1 with 300 mM imidazole per mL of cell-free reaction mixture. All buffers were used and stored at 4° C. Protein was stored at a final concentration of 1-2 mg/mL in sterile 1×PBS (137 mM NaCl, 2.7 mM KCl, 10 mM Na$_2$HPO$_4$, 1.8 mM KH$_2$PO$_4$, pH 7.4) at 4° C.

Expression of bioconjugates in vivo using protein glycan coupling technology (PGCT). Plasmids encoding glycoconjugate carrier gene preceded by the DsbA leader sequence for translocation to the periplasm were transformed into CLM24 cells carrying pGAB2 and pSF-CjPglB. CLM24 carrying only pGAB2 was used as a negative control. Transformed cells were grown in 5 mL LB media (10 g L$^{-1}$ yeast extract, 5 g L$^{-1}$ tryptone, 5 g L$^{-1}$ NaCl) overnight at 37° C. The next day, cells were subcultured into 100 mL LB and allowed to grow at 37° C. for 6 hours after which the culture was supplemented with 0.2% arabinose and 0.5 mM IPTG to induce expression of CjPglB and the bioconjugate carrier protein, respectively. Protein expression was then carried out for 16 h at 30° C., at which point cells were harvested. Cell pellets were resuspended in 1 mL sterile 1×PBS (137 mM NaCl, 2.7 mM KCl, 10 mM Na$_2$HPO$_4$, 1.8 mM KH$_2$PO$_4$, pH 7.4) and lysed using a Q125 Sonicator (Qsonica, Newtown, Conn.) at 40% amplitude in cycles of 10 s on/10 s off for a total of 5 mM Soluble fractions were isolated following centrifugation at 15,000 rpm for 30 mM at 4° C. Protein was purified from soluble fraction using Ni-NTA spin column (Qiagen) following manufacturer's protocol.

Quantification of cell-free protein synthesis yields. To quantify the amount of protein synthesized in iVAX reactions, two approaches were used. Fluorescence units of sfGFP were converted to concentrations using a previously reported standard curve [71]. Yields of all other proteins were assessed via the addition of 10 µM L-$^{14}$C-leucine (11.1 GBq mmol$^{-1}$, PerkinElmer) to the CFPS mixture to yield trichloroacetic acid-precipitable radioactivity that was measured using a liquid scintillation counter as described previously [72]. These reactions were also run on a Coomassie-stained SDS-PAGE gel and exposed by autoradiography. Autoradiographs were imaged with a Typhoon 7000 (GE Healthcare Life Sciences).

Western blot analysis. Samples were run on 4-12% Bis-Tris SDS-PAGE gels (Invitrogen). Following electrophoretic separation, proteins were transferred from gels onto Immobilon-P polyvinylidene difluoride (PVDF) membranes (0.45 µm) according to the manufacturer's protocol. Membranes were washed with PBS (80 g L$^{-1}$ NaCl, 0.2 g L$^{-1}$ KCl, 1.44 g L$^{-1}$ Na$_2$HPO$_4$, 0.24 g L$^{-1}$ KH$_2$PO$_4$, pH 7.4) followed by incubation for 1 h in Odyssey® Blocking Buffer (LiCor). After blocking, membranes were washed 6 times with PBST (80 g L$^{-1}$ NaCl, 0.2 g L$^{-1}$ KCl, 1.44 g L$^{-1}$ Na$_2$HPO$_4$, 0.24 g L$^{-1}$ KH$_2$PO$_4$, 1 mL L$^{-1}$ Tween-20, pH 7.4) with a 5 mM incubation between each wash. For iVAX samples, membranes were probed with both an anti-6×His tag antibody and an anti-O-PS antibody or antisera specific to the O antigen of interest, if commercially available. Probing of membranes was performed for at least 1 hour with shaking at room temperature, after which membranes were washed with PBST in the same manner as described above and probed with fluorescently labeled secondary antibodies. Membranes were imaged using an Odyssey® Fc imaging system (LiCor). CRM197 and TT production were compared to commercial DT and TT standards (Sigma) and orthogonally detected by an identical SDS-PAGE procedure followed by Western blot analysis with a polyclonal antibody that recognizes diphtheria or tetanus toxin, respectively.

TLR4 activation assay. HEK-Blue hTLR4 cell lines were purchased from Invivogen and maintained according to the manufacturer's specifications. Cells were maintained in DMEM media, high glucose/L-glutamine supplement with 10% FBS, 50 U mL$^{-1}$ penicillin, 50 mg mL$^{-1}$ streptomycin, and 100 µg Normacin™ at 37° C. in a humidified atmosphere containing 5% CO$_2$. After reaching ~50-80% confluency, cells were plated into 96-well plates at a density of 1.4×10$^5$ cells per mL in HEK-Blue detection media (Invivogen). Antigens were added at the following concentrations: 100 ng µL$^{-1}$ purified protein; and 100 ng µL$^{-1}$ total protein in lysate. Purified E. coli O55:B5 LPS (Sigma-Aldrich) and detoxified E. coli O55:B5 (Sigma-Aldrich) were added at 1.0 ng mL$^{-1}$ and served as positive and negative controls, respectively. Plates were incubated at 37° C., 5% CO$_2$ for 10-16 h, before being analyzed using a microplate reader at 620 nm. Statistical significance was determined using paired t-tests.

Mouse immunization. Nine groups of six-week old BALB/c mice (Harlan Sprague Dawley) were injected subcutaneously with 100 µL PBS (pH 7.4) alone or containing purified aglycosylated MBP, FtO-PS-conjugated MBP, aglycosylated PD, or FtO-PS-conjugated PD, as previously described [73]. Groups were composed of six mice except for the PBS control group, which was composed of five mice. The amount of antigen in each preparation was normalized to 7.5 µg to ensure that an equivalent amount of aglycosylated protein or bioconjugate was administered in each case. Purified protein groups formulated in PBS were mixed with an equal volume of incomplete Freund's Adjuvant (Sigma-Aldrich) before injection. Prior to immunization, material for each group (5 µL) was streaked on LB agar plates and grown overnight at 37° C. to confirm sterility and endotoxin activity was measured by TLR4 activation assay. Each group of mice was boosted with an identical dosage of antigen 21 d and 42 d after the initial immunization. Blood was obtained on d −1, 21, 35, 49, 63 via submandibular collection and at study termination on d 70 via cardiac puncture. Mice were observed 24 and 48 h after each injection for changes in behavior and physical health and no abnormal responses were observed. This study and all procedures were done in accordance with Protocol 2012-0132 approved by the Cornell University Institutional Animal Care and Use Committee.

Enzyme-linked immunosorbent assay. F. tularensis LPS-specific antibodies produced in immunized mice were measured via indirect ELISA using a modification of a previously described protocol [73]. Briefly, sera were isolated from the collected blood draws after centrifugation at 5,000×g for 10 min and stored at −20° C.; 96-well plates (Maxisorp; Nunc Nalgene) were coated with F. tularensis LPS (BEI resources) at a concentration of 5 µg mL$^{-1}$ in PBS and incubated overnight at 4° C. The next day, plates were washed three times with PBST (PBS, 0.05% Tween-20, 0.3% BSA) and blocked overnight at 4° C. with 5% nonfat dry milk (Carnation) in PBS. Samples were serially diluted by a factor of two in triplicate between 1:100 and 1:12,800, 000 in blocking buffer and added to the plate for 2 h at 37° C. Plates were washed three times with PBST and incubated for 1 h at 37° C. in the presence of one of the following HRP-conjugated antibodies (all from Abcam and used at 1:25,000 dilution): goat anti-mouse IgG, anti-mouse IgG1, and anti-mouse IgG2a. After three additional washes with PBST, 3,3'-5,5'-tetramethylbenzidine substrate (1-Step Ultra TMB-ELISA; Thermo-Fisher) was added, and the plate was incubated at room temperature in the dark for 30 min. The reaction was halted with 2 M $H_2SO_4$, and absorbance was quantified via microplate spectrophotometer (Tecan) at a wavelength of 450 nm. Serum antibody titers were determined by measuring the lowest dilution that resulted in signal 3 SDs above no serum background controls. Statistical significance was determined in RStudio 1.1.463 using one-way ANOVA and the Tukey-Kramer post hoc honest significant difference test.

Serum bactericidal assay. SBA was performed using a modified version of previously reported protocols [74, 75]. An overnight culture of *F. tularensis* LVS Iowa was used to make a suspension of $10^5$ cfu/mL in sterile PBS. Serum samples taken 10 weeks after immunization from unchallenged mice were heat inactivated via incubation at 56° C. for 30 min before use. Human mAb F598 (1 mg/mL=1:1 dilution of mAb) was used as a positive control for bactericidal activity. Serum samples and mAb F598 were diluted 1:2 in sterile PBS and then serially diluted threefold to a maximum dilution factor of 1:54 before being diluted 1:5 in the assay (final concentration range 1:10-1:270). Naïve baby rabbit complement (Cedarlane) or heat-inactivated complement (56° C. for 30 min) was used at a final concentration of 6% (vol/vol). Reactions were incubated at 37° C. for 30 min before 10 μL of each reaction was spotted on cysteine heart agar+9% sheep's blood and allowed to trail down one-half the length of the plate to facilitate colony counting. Plates were then incubated overnight at 37° C., and colonies were counted the next day. Percentage of bactericidal activity was calculated by comparing the number of cfu in a spot with the number of cfu in the spot of the "no complement" control.

Statistical analysis. Statistical parameters including the definitions and values of n, standard deviations, and standard errors are reported in the Figures and corresponding Figure Legends. Analytical techniques are described in the corresponding Methods section.

NON-PATENT REFERENCES

1. Rappuoli, R., Glycoconjugate vaccines: Principles and mechanisms. Sci Transl Med, 2018. 10(456).

2. Roush, S. W., L. McIntyre, and L. M. Baldy, Manual for the surveillance of vaccine-preventable diseases. Atlanta: Centers for Disease Control and Prevention, 2008: p. 4.

3. Astronomo, R. D. and D. R. Burton, Carbohydrate vaccines: Developing sweet solutions to sticky situations? Nat. Rev. Drug Discov., 2010. 9(4): p. 308-24.

4. Avci, F. Y. and D. L. Kasper, How bacterial carbohydrates influence the adaptive immune system. Annu. Rev. Immunol., 2010. 28: p. 107-30.

5. Lockhart, S., Conjugate vaccines. Expert Rev. Vaccines, 2003. 2(5): p. 633-48.

6. Mitchison, N., T-cell-B-cell cooperation. Nat. Rev. Immunol., 2004. 4(4): p. 308.

7. Weintraub, A., Immunology of bacterial polysaccharide antigens. Carbohydr. Res., 2003. 338(23): p. 2539-2547.

8. Jones, C., Vaccines based on the cell surface carbohydrates of pathogenic bacteria. An. Acad. Bras. Cienc., 2005. 77(2): p. 293-324.

9. Trotter, C. L., et al., Optimising the use of conjugate vaccines to prevent disease caused by *Haemophilus influenzae* type b, *Neisseria meningitidis* and *Streptococcus pneumoniae*. Vaccine, 2008. 26(35): p. 4434-45.

10. Frasch, C. E., Preparation of bacterial polysaccharide-protein conjugates: analytical and manufacturing challenges. Vaccine, 2009. 27(46): p. 6468-70.

11. Bhushan, R., B. F. Anthony, and C. E. Frasch, Estimation of group B *Streptococcus* type III polysaccharide-specific antibody concentrations in human sera is antigen dependent. Infect. Immun., 1998. 66(12): p. 5848-53.

12. Kumru, O. S., et al., Vaccine instability in the cold chain: mechanisms, analysis and formulation strategies. Biologicals, 2014. 42(5): p. 237-59.

13. Organization, W. H. Temperature Sensitivity of Vaccines. 2014; Available from: www.who.int/immunization/programmes_systems/supply_chain/resources/VaccineStability_EN.pdf.

14. Matthias, D. M., et al., Freezing temperatures in the vaccine cold chain: a systematic literature review. Vaccine, 2007. 25(20): p. 3980-6.

15. Ashok, A., M. Brison, and Y. LeTallec, Improving cold chain systems: Challenges and solutions. Vaccine, 2017. 35(17): p. 2217-2223.

16. Feldman, M. F., et al., Engineering N-linked protein glycosylation with diverse O antigen lipopolysaccharide structures in *Escherichia coli*. Proc. Natl. Acad. Sci. U.S.A., 2005. 102(8): p. 3016-21.

17. Garcia-Quintanilla, F., et al., Production of a recombinant vaccine candidate against *Burkholderia pseudomallei* exploiting the bacterial N-glycosylation machinery. Front. Microbiol., 2014. 5: p. 381.

18. Wetter, M., et al., Engineering, conjugation, and immunogenicity assessment of *Escherichia coli* O121 O antigen for its potential use as a typhoid vaccine component. Glycoconj. J., 2013. 30(5): p. 511-22.

19. Ma, Z., et al., Glycoconjugate vaccine containing *Escherichia coli* O157:H7 O-antigen linked with maltose-binding protein elicits humoral and cellular responses. PLoS One, 2014. 9(8): p. e105215.

20. Cuccui, J., et al., Exploitation of bacterial N-linked glycosylation to develop a novel recombinant glycoconjugate vaccine against *Francisella tularensis*. Open Biol., 2013. 3(5): p. 130002.

21. Marshall, L. E., et al., An O-antigen glycoconjugate vaccine produced using protein glycan coupling technology is protective in an inhalational rat model of tularemia. J. Immunol. Res., 2018. 2018: p. 8087916.

22. Wacker, M., et al., Prevention of *Staphylococcus aureus* infections by glycoprotein vaccines synthesized in *Escherichia coli*. J. Infect. Dis., 2014. 209(10): p. 1551-61.

23. Carlson, E. D., et al., Cell-free protein synthesis: Applications come of age. Biotechnol. Adv., 2012. 30(5): p. 1185-94.

24. Pardee, K., et al., Portable, on-demand biomolecular manufacturing. Cell, 2016. 167(1): p. 248-259.e12.

25. Adiga, R., et al., Point-of-care production of therapeutic proteins of good-manufacturing-practice quality. Nat. Biomed. Eng., 2018.

26. Pardee, K., et al., Paper-based synthetic gene networks. Cell, 2014. 159(4): p. 940-54.

27. Pardee, K., et al., Rapid, low-cost detection of Zika virus using programmable biomolecular components. Cell, 2016. 165(5): p. 1255-66.

28. Perez, J. G., J. C. Stark, and M. C. Jewett, Cell-free synthetic biology: Engineering beyond the cell. Cold Spring Harb. Perspect. Biol., 2016.

29. Jaroentomeechai, T., et al., Single-pot glycoprotein biosynthesis using a cell-free transcription-translation system enriched with glycosylation machinery. Nat. Commun., 2018. 9(1): p. 2686.

30. Haghi, F., et al., Cloning, expression and purification of outer membrane protein PorA of *Neisseria meningitidis* serogroup B. J Infect Dev Ctries, 2011. 5(12): p. 856-62.

31. Stefan, A., et al., Overexpression and purification of the recombinant diphtheria toxin variant CRM197 in *Escherichia coli*. J Biotechnol, 2011. 156(4): p. 245-52.

32. Figueiredo, D., et al., Characterization of recombinant tetanus toxin derivatives suitable for vaccine development. Infect. Immun., 1995. 63(8): p. 3218-21.

33. Schoborg, J. A., et al., A cell-free platform for rapid synthesis and testing of active oligosaccharyltransferases. Biotechnol. Bioeng., 2017.

34. Yin, G., et al., Aglycosylated antibodies and antibody fragments produced in a scalable in vitro transcription-translation system. MAbs, 2012. 4(2): p. 217-25.

35. Chen, M. M., K. J. Glover, and B. Imperiali, From peptide to protein: comparative analysis of the substrate specificity of N-linked glycosylation in *C. jejuni*. Biochemistry, 2007. 46(18): p. 5579-85.

36. Bayburt, T. H. and S. G. Sligar, Membrane protein assembly into Nanodiscs. FEBS Lett., 2010. 584(9): p. 1721-7.

37. Knapp, K. G., A. R. Goerke, and J. R. Swartz, Cell-free synthesis of proteins that require disulfide bonds using glucose as an energy source. Biotechnol. Bioeng., 2007. 97(4): p. 901-8.

38. Oyston, P. C., A. Sjostedt, and R. W. Titball, Tularaemia: bioterrorism defence renews interest in *Francisella tularensis*. Nat. Rev. Microbiol., 2004. 2(12): p. 967-78.

39. Fulop, M., et al., Role of antibody to lipopolysaccharide in protection against low- and high-virulence strains of *Francisella tularensis*. Vaccine, 2001. 19(31): p. 4465-72.

40. Lu, Z., et al., Protective B-cell epitopes of *Francisella tularensis* O-polysaccharide in a mouse model of respiratory tularaemia. Immunology, 2012. 136(3): p. 352-60.

41. Prior, J. L., et al., Characterization of the O antigen gene cluster and structural analysis of the O antigen of *Francisella tularensis* subsp. *tularensis*. J. Med. Microbiol., 2003. 52(Pt 10): p. 845-51.

42. Kowarik, M., et al., Definition of the bacterial N-glycosylation site consensus sequence. EMBO J., 2006. 25(9): p. 1957-66.

43. Hatz, C. F., et al., Safety and immunogenicity of a candidate bioconjugate vaccine against *Shigella dysenteriae* type 1 administered to healthy adults: A single blind, partially randomized Phase I study. Vaccine, 2015. 33(36): p. 4594-601.

44. Huttner, A., et al., Safety, immunogenicity, and preliminary clinical efficacy of a vaccine against extraintestinal pathogenic *Escherichia coli* in women with a history of recurrent urinary tract infection: a randomised, single-blind, placebo-controlled phase 1b trial. Lancet. Infect. Dis., 2017.

45. Riddle, M. S., et al., Safety and immunogenicity of a candidate bioconjugate vaccine against *Shigella flexneri* 2a administered to healthy adults: a single blind, randomized phase I study. Clin. Vaccine Immunol., 2016.

46. Laferriere, C. A., et al., *Streptococcus pneumoniae* type 14 polysaccharide-conjugate vaccines: length stabilization of opsonophagocytic conformational polysaccharide epitopes. Infect. Immun., 1998. 66(6): p. 2441-6.

47. Paoletti, L. C., et al., Effects of chain length on the immunogenicity in rabbits of group B *Streptococcus* type III oligosaccharide-tetanus toxoid conjugates. J. Clin. Invest., 1992. 89(1): p. 203-9.

48. Qadri, F., et al., Enterotoxigenic *Escherichia coli* in developing countries: epidemiology, microbiology, clinical features, treatment, and prevention. Clin. Microbiol. Rev., 2005. 18(3): p. 465-83.

49. Johnson, J. R., Virulence factors in *Escherichia coli* urinary tract infection. Clin. Microbiol. Rev., 1991. 4(1): p. 80-128.

50. Jansson, P. E., et al., Structural studies of the *Escherichia coli* O78 O-antigen polysaccharide. Carbohydr. Res., 1987. 165(1): p. 87-92.

51. Valvano, M. A. and J. H. Crosa, Molecular cloning and expression in *Escherichia coli* K-12 of chromosomal genes determining the O7 lipopolysaccharide antigen of a human invasive strain of *E. coli* O7:K1. Infect. Immun., 1989. 57(3): p. 937-43.

52. Rietschel, E. T., et al., Bacterial endotoxin: molecular relationships of structure to activity and function. FASEB J., 1994. 8(2): p. 217-25.

53. Russell, J. A., Management of sepsis. N. Engl. J. Med., 2006. 355(16): p. 1699-1713.

54. Brito, L. A. and M. Singh, Acceptable levels of endotoxin in vaccine formulations during preclinical research. J. Pharm. Sci., 2011. 100(1): p. 34-7.

55. Petsch, D. and F. B. Anspach, Endotoxin removal from protein solutions. J. Biotechnol., 2000. 76(2-3): p. 97-119.

56. Casella, C. R. and T. C. Mitchell, Putting endotoxin to work for us: monophosphoryl lipid A as a safe and effective vaccine adjuvant. Cell. Mol. Life Sci., 2008. 65(20): p. 3231-40.

57. Chen, L., et al., Outer membrane vesicles displaying engineered glycotopes elicit protective antibodies. Proc. Natl. Acad. Sci. U.S.A., 2016.

58. Needham, B. D., et al., Modulating the innate immune response by combinatorial engineering of endotoxin. Proc. Natl. Acad. Sci. U.S.A., 2013. 110(4): p. 1464-9.

59. Bogaert, D., et al., Pneumococcal vaccines: an update on current strategies. Vaccine, 2004. 22(17-18): p. 2209-20.

60. Raetz, C. R. and C. Whitfield, Lipopolysaccharide endotoxins. Annu. Rev. Biochem., 2002. 71: p. 635-700.

61. CDC, CDC Vaccine Price List. 2018.

62. Bachmann, M. F., et al., The influence of antigen organization on B cell responsiveness. Science, 1993. 262 (5138): p. 1448-51.

63. Desaymard, C. and J. G. Howard, Role of epitope density in the induction of immunity and tolerance with thymus-independent antigens. II. Studies with 2,4-dinitrophenyl conjugates in vivo. Eur. J. Immunol., 1975. 5(8): p. 541-5.

64. Li, Q., et al., Effects of hapten density on the induced antibody repertoire. Chembiochem, 2010. 11(12): p. 1686-91.

65. Perez-Pinera, P., et al., Synthetic biology and microbioreactor platforms for programmable production of biologics at the point-of-care. Nat Commun, 2016. 7: p. 12211.

66. Crowell, L. E., et al., On-demand manufacturing of clinical-quality biopharmaceuticals. Nat Biotechnol, 2018.

67. Salehi, A. S., et al., Cell-free protein synthesis of a cytotoxic cancer therapeutic: Onconase production and a just-add-water cell-free system. Biotechnol. J., 2016. 11(2): p. 274-81.

68. Datsenko, K. A. and B. L. Wanner, One-step inactivation of chromosomal genes in *Escherichia coli* K-12 using PCR products. Proc. Natl. Acad. Sci. USA, 2000. 97(12): p. 6640-5.

69. Ollis, A. A., et al., Substitute sweeteners: Diverse bacterial oligosaccharyltransferases with unique N-glycosylation site preferences. Sci. Rep., 2015. 5: p. 15237.

70. Jewett, M. C. and J. R. Swartz, Mimicking the *Escherichia coli* cytoplasmic environment activates long-lived and efficient cell-free protein synthesis. Biotechnol. Bioeng., 2004. 86(1): p. 19-26.

71. Hong, S. H., et al., Cell-free protein synthesis from a release factor 1 deficient *Escherichia coli* activates efficient and multiple site-specific nonstandard amino acid incorporation. ACS Synth. Biol., 2014. 3(6): p. 398-409.

72. Kim, D. M. and J. R. Swartz, Regeneration of adenosine triphosphate from glycolytic intermediates for cell-free protein synthesis. Biotechnol. Bioeng., 2001. 74(4): p. 309-16.

73. Chen, D. J., et al., Delivery of foreign antigens by engineered outer membrane vesicle vaccines. Proc. Natl. Acad. Sci. U.S.A., 2010. 107(7): p. 3099-104.

74. Cywes-Bentley, C., et al., Antibody to a conserved antigenic target is protective against diverse prokaryotic and eukaryotic pathogens. Proc. Natl. Acad. Sci. U.S.A., 2013. 110(24): p. E2209-18.

75. Sebastian, S., et al., A defined O-antigen polysaccharide mutant of *Francisella tularensis* live vaccine strain has attenuated virulence while retaining its protective capacity. Infect. Immun., 2007. 75(5): p. 2591-602.

76. Ollis, A. A., et al., Engineered oligosaccharyltransferases with greatly relaxed acceptor-site specificity. Nat. Chem. Biol., 2014. 10(10): p. 816-22.

77. Celik, E., et al., Glycoarrays with engineered phages displaying structurally diverse oligosaccharides enable high-throughput detection of glycan-protein interactions. Biotechnol. J., 2015. 10(1): p. 199-209.

PATENT REFERENCES

U.S. Pat. Nos. 4,496,538; 4,727,136; 5,478,730; 5,556,769; 5,623,057; 5,665,563; 5,679,352; 6,168,931; 6,248,334; 6,518,058; 6,783,957; 6,869,774; 6,994,986; 7,118,883; 7,189,528; 7,338,789; 7,387,884; 7,399,610; 8,703,471; and 8,999,668; U.S. Publication Nos. 2005/0170452; 2006/0211085; 2006/0234345; 2006/0252672; 2006/0257399; 2006/0286637; 2007/0026485; 2007/0178551; 2015/0259757; 2016/0060301; 2016/0362708; 2017/0349928; 20180016614; 2018/0044905; International Publication Nos. WO2003/056914A1; WO2004/013151A2; WO2004/035605A2; WO2006/102652A2; WO2006/119987A2; and WO2007/120932A2; the contents of which are incorporated herein by reference in their entireties.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references are made herein. The cited references are incorporated by reference herein in their entireties. In the event that there is an inconsistency between a definition of a term in the specification as compared to a definition of the term in a cited reference, the term should be interpreted based on the definition in the specification.

We claim:

1. A method for synthesizing an N-glycosylated carrier protein for a polysaccharide via coordinated transcription, translation, and N-glycosylation in vitro, in a single vessel, the method comprising:

transcribing and translating a carrier protein in a cell-free protein synthesis reaction, the carrier protein comprising an inserted consensus sequence, D/E-$X_1$-N-$X_2$-S/T or N-X-S/T, wherein X, $X_1$ and $X_2$ may be any natural or unnatural amino acid except proline;

(ii) glycosylating the carrier protein in the cell-free protein synthesis reaction with at least one polysaccharide, wherein the at least one polysaccharide is at least one bacterial O-antigen;

wherein the single vessel comprises a template encoding the carrier protein, an exogenous lipid-linked oligosaccharide (LLO) comprising the bacterial O-antigen, and one or more *Escherichia coli* (*E. coli*) cell lysates from engineered *E. coli* strains, wherein the engineered *E. coli* strains comprise:
(a) a nucleic acid encoding an orthogonal or heterologous oligosaccharyltransferase (OST) which is expressed in the engineered *E. coli* strains;
(b) one or both of:
  (1) a mutation of the endogenous lpxM gene wherein the mutation results in the reduced expression or and/or activity of the encoded myristoyltransferase;
  (2) a nucleic acid comprising an orthogonal or heterologous LpxE gene and encoding a lipidA 1-phosphatase which is expressed in the engineered *E. coli* strains;
(c) a mutation in the endogenous waaL gene, wherein the mutation results in the reduced expression and/or activity of the encoded O-antigen ligase;
(d) prokaryotic transcription and translation machinery.

2. The method of claim 1, wherein the bacterial O-antigen is from *E. coli*.

3. The method of claim 1, wherein the bacterial O-antigen is from *Franciscella tularensis*.

4. The method of claim 1, further comprising formulating the N-glycosylated carrier protein as an antigenic composition comprising the N-glycosylated carrier protein.

5. The method of claim 1, further comprising formulating the N-glycosylated carrier protein as a vaccine composition comprising the N-glycosylated carrier protein.

6. The method of claim 5, wherein the vaccine composition further comprises an adjuvant.

7. The method of claim 1, wherein the carrier protein is an engineered variant of *E. coli* maltose binding protein (MBP).

8. The method of claim 1, wherein the carrier protein is selected from a detoxified variant of the toxin from *Clostridium tetani*, a detoxified variant of the toxin from *Corynebacterium diptheriae*, *Haemophilus influenzae* protein D (PD) or a variant thereof, and *Neisseria meningitidis* porin protein (PorA) or a variant thereof.

9. The method of claim 1, wherein the glycosylating step utilizes an oligosaccharyltransferase (OST) which is a naturally occurring bacterial homolog of *C. jejuni* PglB, and wherein the consensus sequence comprises $D/E-X_1-N-X_2-S/T$.

10. The method of claim 1, wherein the glycosylating step utilizes an OST that is an engineered variant of *C. jejuni* PglB, and wherein the consensus sequence comprises $D/E-X_1-N-X_2-S/T$.

11. The method of claim 1, wherein the wherein the glycosylating step utilizes an OST that is a naturally occurring archaeal OST, and wherein the consensus sequence comprises N-X-S/T.

12. The method of claim 1, wherein the wherein the glycosylating step utilizes an OST which is a naturally occurring single-subunit eukaryotic OST, and wherein the consensus sequence comprises N-X-S/T.

13. The method of claim 1, wherein the heterologous LpxE gene is from *F. tularensis*.

14. The method of claim 1, wherein the one or more cell lysates have an endotoxin unit (EU) concentration of less than about 180,000 EU/ml.

15. A method of vaccinating a subject in need thereof against a bacterial O-antigen, the method comprising administering to the subject the vaccine composition of claim 5.

* * * * *